US011065330B2

(12) United States Patent
Bredehorst et al.

(10) Patent No.: US 11,065,330 B2
(45) Date of Patent: Jul. 20, 2021

(54) INDUCTION OF ANTIGEN-SPECIFIC TOLERANCE BY PERIPHERAL PHAGOCYTOSIS

(71) Applicants: PLS-Design GmbH, Hamburg (DE); Helmholtz-Zentrum Muenchen Forschungszentrum fuer Gesundheit und Umwelt GmbH, Neuherberg (DE)

(72) Inventors: Reinhard Bredehorst, Hamburg (DE); Thomas Grunwald, Hamburg (DE); Carsten Schmidt-Weber, Munich (DE)

(73) Assignee: PLS-Design GmbH, Hamburg (DE)

( * ) Notice: Subject to any disclaimer, the term of this patent is extended or adjusted under 35 U.S.C. 154(b) by 0 days.

(21) Appl. No.: 14/643,495

(22) Filed: Mar. 10, 2015

(65) Prior Publication Data
US 2015/0283231 A1 Oct. 8, 2015

(30) Foreign Application Priority Data
Mar. 10, 2014 (EP) .................... 14075015

(51) Int. Cl.
*A61K 39/35* (2006.01)
*A61K 39/00* (2006.01)
*A61K 9/127* (2006.01)
*A61K 9/00* (2006.01)
*A61K 39/04* (2006.01)
*A61K 9/19* (2006.01)
*A61K 9/06* (2006.01)

(52) U.S. Cl.
CPC ............ *A61K 39/35* (2013.01); *A61K 9/0024* (2013.01); *A61K 9/06* (2013.01); *A61K 9/127* (2013.01); *A61K 9/1271* (2013.01); *A61K 9/19* (2013.01); *A61K 39/00* (2013.01); *A61K 39/0005* (2013.01); *A61K 39/04* (2013.01); *A61K 2039/54* (2013.01); *A61K 2039/55505* (2013.01); *A61K 2039/55511* (2013.01); *A61K 2039/55555* (2013.01); *A61K 2039/577* (2013.01); *A61K 2039/58* (2013.01); *A61K 2039/6093* (2013.01)

(58) Field of Classification Search
CPC combination set(s) only.
See application file for complete search history.

(56) References Cited

U.S. PATENT DOCUMENTS

2012/0121539 A1* 5/2012 Sands .................... A61K 39/35
424/85.2
2012/0276158 A1* 11/2012 Fraser .................... A61K 39/00
424/400

FOREIGN PATENT DOCUMENTS

WO  WO 2006/059142  * 6/2006
WO  2009046198  4/2009

OTHER PUBLICATIONS

Zentner et al (J of Controlled Release, 2001,72:203-215).*
Xing et al (J Liposome Research, 2014, 24:10-16, online Aug. 8, 2013).*
Alinaghi et al (J Liposome Research, 2013, 23:235-243.*
Hoare et al (Polymer, 2008, 49:1993-2007).*
Bach (The Effects of Topical Calcipotriol treatment on immune responses to vaccination, Thesis, University of British Columbia, Jun. 2008).*
Willart et al (Allergology International, 2010, 59:95-103).*
Singh, S., et al., Int. J. Pharmaceutics 341: 68-77; 2007.
Sinha, V.R., et al., Int. J. Pharm. 278: 1-23; 2004.
Skyler, J.S., et al., Diabetes Care 28: 1068-1076; 2005.
Steed, P.M., et al., Science 301: 1895-1898; 2003.
Steinman, L., Zamvil, S.S., Ann. Neurol. 68: 567-569; 2010.
Strainic, M.G., et al., Immunity 28: 425-435; 2008.
Sun, Y.P., et al., J. Biol. Chem. 282: 9323-9334; 2007.
Suvannavejh, G.C., et al., Cell. Immunol. 205: 24-33; 2000.
Taher, Y.A., et al., J. Immunol. 180: 5211-5221; 2008.
Tan, L.J., et al., J. Immunol. 147: 1797-1802 ; 1991.
Taurog, J.D., et al., Methods Enzymol. 162: 339-355; 1988.
Thole, J.E.R., et al., Infect. Immun. 55:1466-1475; 1987.
Thommesen, L., Laegreid, A., J. Biochem. Mol. Biol. 38: 281-289; 2005.
Ting, E., et al., Br. J. Pharmacol. 153: 1043-1053; 2008.
Tirouvanziam R., et al., Proc. Natl. Acad. Sci. USA 103: 4628-4633; 2006.
Tony, H.P., et al., Eur. J. Biochem. 225: 659-665; 1994.
Torchilin, V.P., Nature Rev. 4 : 145-160 ; 2005.
Van der Aar, A.M.G., et al., J. Allergy Clin. Immunol. 127: 1532-1540; 2011.
Van der Zee, R., et al., Eur. J. Immunol. 19: 43-47; 1989.
Van Eden, W., et al., Nature 331: 171-173; 1988.
Van Hauwermeiren, F., et al., Cytokine Growth Factors Rev. 22: 311-319; 2011.
Voll, R.E., et al., Nature 390 : 350-351 ; 1997.
Wagner, E., Frank M.M., Nature Rev. 9: 43-56; 2010.
Warren, K.G., et al., Eur. J. Neurol. 13: 887-895; 2006.
Wei, X, et al., Pharm Res. 23: 1251-1264. doi: 10.1007/s11095-006-0082-3; 2006.
Wenzel, S., et al., Lancet 370: 1422-1431; 2007.
Wingerchuk D.M., et al., J. Neurol. Neurosurg. Psychiatry 76: 1294-1296; 2005.
Wittke, A., et al., J. Immunol. 173: 3432-3436; 2004.

(Continued)

*Primary Examiner* — Laura B Goddard
(74) *Attorney, Agent, or Firm* — Mayer & Williams, PC; Stuart H. Mayer

(57) ABSTRACT

The invention relates to a pharmaceutical composition for modulation of T cell and B cell responses by antigen- or allergen-specific immunotherapy in combination with peripheral tolerance-inducing phagocytosis, made of one or more preparations and comprising one or more matrices suitable for locally restricted sustained release of a physiologically effective dose of at least one antigen or allergen, liposomes tailored for effective phagocytosis, one or more immune modulators of phagocytosis, and one or more immune modulators suitable for enhancing the suppressive function of regulatory T cells at the site of antigen or allergen presentation.

6 Claims, 8 Drawing Sheets

Specification includes a Sequence Listing.

(56) References Cited

OTHER PUBLICATIONS

Woodruff, T.M., et al., Arthritis Rheum. 46: 2476-2485; 2002.
Woodruff, T.M., et al., J. Pharmacol. Exp. Ther. 314: 811-817; 2005.
Woodruff, T.M., et al., FASEB J. 20: 1407-1417; 2006.
Wu, Y., et al., Biomaterials 33: 2351-3260; 2012.
Xing, Y., et al., J. Liposome Res., early online 1-7 ; 2013.
Yalcindag, A., et al., J. Allergy Clin. Immunol. 117: 1455-1461; 2006.
Yang, X., et al., Clin. Exp. Immunol. 81: 189-194; 1990.
Zaharoff, D.A., et al., Vaccine 25: 2085-2094; 2007.
Zella, J.B., et al., Arch. Biochem. Biophys. 417: 77-80; 2003.
Zhang, J., et al., Biomacromolecules 7: 2492-2500; 2006.
Zhang, X, Kohl, J., Expert Rev. Clin. Immunol. 6: 269-277; 2010.
Abbott, D.J., et al., BMC Immunol. 12: 72; 2011.
Abramson, M.J., et al. Cochrane Database Syst. Rev. CD001186; 2003.
Alexopoulou, L., et al., Eur. J. Immunol. 36: 2768-2780; 2006.
Alhalaweh, A., et al., Eur. J. Pharm. Sci. 38: 206-214; 2009.
Ames, R.S., et al., J. Immunol. 166: 6341-6348; 2001.
Andjelkovic, Z., et al., Clin. Exp. Rheumatol. 17: 453-456; 1999.
Arnon, R., Immunol. Lett. 50: 1-125; 1996.
Arnon, R., Aharoni R., Proc. Natl. Acad. Sci. USA 101, suppl. 2: 14593-14598; 2004.
Arntz, O.J., et al., Arthritis Res. Therapy 12: R61; 2010.
Arumugam, T.V., et al., Kidney Int. 63:134-142; 2003.
Arumugam, T.V., et al., J. Hepatol. 40: 934-941; 2004.
Arur, S., et al., Develop. Cell 4 : 587-598 ; 2003.
Badawi, A.H., Siahaan T.J., Clin. Immunol. 144: 127-138; 2012.
Baelder, R., et al., J. Immunol. 174: 783-789; 2005.
Balasubramanian, K., Schroit, A.J., J. Biol. Chem. 273: 29272-29277; 1998.
Bao, L., et al., J. Immunol. 175: 1947-1955; 2005a.
Bao, L., et al., Eur. J. Immunol. 35: 2496-2506; 2005b.
Basomba, A., et al., J. Allergy Clin. Immunol. 109: 943-948; 2002.
Belogurov, Jr.,A.A., et al., FASEB J. 27: 222-231; 2013.
Bluestone, J.A., et al., Nature 464: 1293-1300; 2010.
Branisteanu, D.D., et al., J. Neuroimmunol. 61: 151-160; 1995.
Brunner, R., et al., Immunol. Lett. 128: 29-35; 2010.
Cailleret, M., et al., Circulation 109: 406-411; 2004.
Cantorna, M.T., et al., J. Nutr. 128: 68-72; 1998.
Chaurio, R.A., et al., Molecules 14 : 4892-4914 ; 2009.
Chemnitz, J.M., et al. J. Immunol. 173: 945-954 ; 2004.
Chen, X., Oppenheim J.J. In: TNF pathophysiology. Molecular and cellular mechanisms. Curr. Dir. Autoimmun., pp. 119-134, Karger, Basel; 2010.
Choi, S., et al., Pharmaceut. Res. 20: 2008-2010; 2003.
Cianferoni, A., et al., Blood 97: 1742-1749; 2001.
Cohen, I.R., et al., Arthritis Rheum. 8: 841-845; 1985.
Cohen, S., et al.., Biochim. Biophys. Acta 1063: 95-102; 1991.
Das, A., et al., J. Immunol. 192: 1120-1129; 2014.
Demedts, M., et al., N. Engl. J. Med. 353: 2229-2242; 2005.
Diamyd (2011) Diamyd US phase III trial: http://clinicaltrials.gov/ct2/show/NCT00751842.
Diamyd (2011) Diamyd European phase III trial: http://clinicaltrials.gov/ct2/show/NCT00723411.
Diamyd (2011) Diabetes prevention—immune tolerance (DIAPREV-IT) http://clinicaltrials.gov/ct2/show/NCT01122446 ?term=diamyd &rank=6.
Eagar, T.N., et al., Eur. J. Immunol. 32 : 972-981 ; 2002.
Elias, D., et al., Proc. Natl. Acad. Sci. USA 87: 1576-1580; 1990.
Elias, D., et al., Proc. Natl. Acad. Sci. USA 88: 3088-3091; 1991.
Elliott, M.R., et al., Nature 461 : 282-286 ; 2009.
Engel, A., et al., Pharmaceutical Res. 20 : 51-57 ; 2003.
Eylar, E., et al., Int. Immunol. 1:97-101; 1993.
Fadok, V.A., et al., J. Immunol. 148: 2207-2216 ; 1992.
Fadok, V.A., et al., J. Biol. Chem. 276: 1071-1077 ; 2001.
Faria, A.M., Weiner, H.L., Immunol. Rev. 206: 232-259; 2005.
Fife, B.T., et al., J. Exp. Med. 203 : 2737-2747 ; 2006.
Fletcher, J.M., et al., Recent Pat. Inflamm. Allergy Drug Discov. 6: 22-34; 2012.
Fukasawa, M., et al., FEBS Letters 441 : 353-366 ; 1998.
Furst, D.E., et al., J. Rheumatol. 14: 342-347; 1987.
Galvain, S., et al., Current Therap. Res. 60 : 278-294 ; 1999.
Kissmeyer, A.-M., Binderup, L., Biochem. Pharmacol.41: 1601-1606; 1991.
Köhl, J., Curr. Opin. Mol. Ther. 8: 529-538; 2006.
Kono, H., Rock, K.L., Nature Rev. Immunol. 8 : 279-289 ; 2008.
Kornbluth, R.S., Immunol. Lett.43 : 125-132 ; 1994.
Kragballe K, Pharmacol. Toxicol. 77: 241-246; 1995.
Kukoc-Modun, L., Radic, N., Internatl. J. Analyt. Chem. 2011: article ID 140756; 2011.
Landewe, R.B.M., et al., Ann. Rheum. Dis. 69: 1655-1659; 2010.
Leadbetter, E.A., et al., J. Immunol. 161: 504-512; 1998.
Lee, Y.C., et al., Biochemistry 15 : 3956-3963 ; 1976.
Leroux-Roels, G., Vaccine 285: C25-C36; 2010.
Lin, M., et al., Diabetes 59: 2247-2252; 2010.
Liu, J., et al., J. Immunol. 180: 5882-5889; 2008.
Ludvigsson, J., et al., N. Engl. J. Med. 359: 676-781; 2008.
Lutterotti, A., et al., Sci. Translat. Med. 5 : 1-19 ; 2013.
Macauley, M.S., et al., J. Clin. Invest. 123: 3074-3083; 2013.
Majak P., et al., J. Allergy Clin. Immunol. 127: 1294-1296 ; 2011.
Markiewski, M.M., et al., Nat. Immunol. 9 : 1225-1235 ; 2008.
Mathieu, C., et al., Diabetologica 37: 552-558; 1994.
Meechan, P., et al., Int. Arch. Allergy Immunol. 61 : 351-362 ; 2013.
Mizuochi, T., et al., J. Biol Chem. 264: 13834-13939 ; 1989.
Moller, C., et al., J. Allergy Clin. Immunol. 109: 251-256; 2002.
Monastra, G., Bruni, A., Lymphokine Cytokine Res. 11 : 39-43; 1992.
Monastra, G., et al., Neurology 43 : 153-163 ; 1993.
Monk, P.N., et al., Brit. J. Pharmacol. 152: 429-448; 2007.
Nicholls, E.F., et al., Ann. N.Y. Acad. Sci. 1213: 46-61; 2010.
Nie, S., et al., Internatl. J. Nanomed. 6: 151-166; 2011.
Nomura, T., et al., J. Control. Release 149: 8-14; 2011.
Ojwang, J.O., Rando R.F.. METHODS: A Companion to Methods in Enzymology 18: 244-251; 1999.
Ostergaard, J.A., et al., Diabetes 60: e7-e8; 2011.
Pai, S.S., et al., Am. Assoc. Pharmac. Sci. J. 11: 88-98; 2009.
Peng, K.-T., et al., Biomaterials 31: 5227-5236; 2010.
Pfrengle, F., et al., J. Immunol. 191 : 1724-1731 ; 2013.
Plum, L.A., DeLuca, H.F., Nat. Rev. Drug Discov. 9: 941-955; 2010.
Ponzin, D., et al., Immunopharmacol. 18 : 167-176 ; 1989.
Proctor, L.M., et al., Brit. J. Pharmacol. 142: 756-764; 2004.
Qiao, M. et al., Int. J. Pharm. 294: 103-112; 2005.
Qu, H., et al., Mol. Immunol. 47: 185-195; 2009.
Ravichandran, K.S.,J. Exp. Med. 207: 1807-1817 ; 2010.
Ravichandran, K.S., Immunity 35 : 445-455 ; 2011.
Ricklin, D., Lambris, J.D., Adv. Exp. Med. Biol. 632: 273-292; 2008.
Rolland, J.M., et al., Pharmacol. Ther. 121: 273-284; 2009.
Ross, P.C., et al., J. Liposome Res. 8: 499-520; 1998.
Ruel-Gariepy, E., Leroux, J-C., Eur. J. Pharmaceutics Biopharmaceutics 58: 409-426; 2004.
Sahu, A., et al., J. Immunol. 157: 884-891; 1996.
Sahu, A., et al., Mol. Immunol. 39: 557-566; 2003.
Schmidt-Weber, C., Blaser, K. Inflamm. Allergy Drug Targets 5: 15-21; 2006.
Shephard, R.M., DeLuca, H.F., Arch. Biochem. Biophys. 202: 43-53; 1980.
Shibata, H., et al., J. Biol. Chem. 283: 998-1007; 2008.
Shibata, H., et al., Biomaterials 30: 6638-6647; 2009.
Silasi-Mansat, R., et al., Blood 116: 1002-1010; 2010.
Gao, X., et al., Clin. Immunol. 140: 236-243; 2011.
Gardai, S.J., et al., Cell 123 : 321-334 ; 2005.
Garren, H., et al., Ann. Neurol. 63 : 611-620 ; 2008.
Gaskins, H.M., et al., J. Clin. Invest. 90 : 2220-2227;1992.
Geelen, T., et al., J. Nanobiotechnology 10 : 37-48 ; 2012.
Getts, D.R., et al., J. Immunol. 187 : 2405-2417 ; 2011.
Ghoreishi, M., et al., J. Immunol. 182: 6071-6078; 2009.
Gilbert, J.C., et al., J. Control. Release 5: 113-118; 1987.
Gilbreath, M.J., et al., J. Immunol. 134 : 3420-3425 ; 1985.

(56) References Cited

OTHER PUBLICATIONS

Giulietti, A., et al., Diabetologica 47: 451-462; 2004.
Gogishvili, T., et al., Int. Arch. Allergy Immunol. 142: 165-174; 2006.
Gong, C.Y., et al., Int. J. Pharm. 365: 89-99; 2009a.
Gong, C.Y., et al., BMC Biotechnol. 9: 8; 2009b.
Goulding, N.J., et al., Inflamm. Res. 3 : 5158-5165 ; 1998.
Grassetti, D.R., Murray, J.F., Arch. Biochem. Biophys. 119: 41-49; 1967.
Grunewald, S.M., et al., J. Immunl. 160: 404-4009; 1998.
Hagenaars, N., et al., J. Control. Release 144: 17-24; 2010.
Hanayama, R., et al., Nature 417 : 182-187 ; 2002.
Harel-Adar, T., et al., Proc. Natl. Acad. Sci. USA 108 : 1827-1832 ; 2011.
Harkin, D.W., et al., J. Vasc. Surg. 39: 196-205; 2004.
Harris, S.S., J. Nutr. 135: 323-325; 2005.
Hashimoto, M., et al., J. Exp. Med. 207: 1135-1143; 2010.
Higuchi, K., et al., J. Rheumatol. 27 : 1038-1044 ; 2000.
Hochreiter-Hufford, A., Ravichandran,K.S., Cold Spring Harb. Perspect. Biol. 5: a008748; 2013.
Hoffmann, P.R., et al., J. Immunol. 174: 1393-1404 ; 2005.
Hogervorst, E.J.M., et al., Internatl. Immunol 4: 719-727; 1992.
Holgate, St., Polosa, R., Nature Rev. Immunol 8: 218-230; 2008.
Huang, X.W., et al., Clin. Cancer Res. 12: 2849-2855; 2006.
Huber-Lang, M., et al., Am. J. Pathol. 161: 1849-1859; 2002.
Hyppönen, E., et al., Lancet 358: 1500-1503; 2001.
Hyun, H., et al., Biomacromolecules 8: 1093-1100; 2007.
Ichim, T.E., et al., Expert Opin. Biol. Ther. 8: 191-199; 2008.
Igarashi, M., et al., Clin. Exper. Immunol. 93 : 19-25 ; 1993.
Ikehara, Y., et al., Cancer Res. 66: 8740-8748; 2006.
Ishii, M., et al., Intern. Immunopharmacol.10: 1041-1046; 2010.
Iyer, R.P., et al., J. Org. Chem. 55: 4693-4699; 1990.
Jacobsen, L., et al., Allergy 62: 943-948; 2007.
Jeannin, P., et al., J. Exp. Med. 182: 1785-1792; 1995.
Jenkins, M.K., Schwartz, R.H., J. Exp. Med. 165 : 202-319; 1987.
Jeong, B., et al., Nature 388: 860-862, 1997.
Jurynczyk, M., et al., Ann. Neurol. 68 : 593-601 ; 2010.
Kamphuis, S., et al., Lancet 366 : 50-56 ; 2005.
Kang, Y.M., et al., Biomaterials 31: 2453-2460; 2010.
Kassiotis, G., Kollias, G., J. Exp. Med. 1993: 427-434; 2001.
Kawakami, S., et al., Biochim. Biophys. Acta 1524: 258-265; 2000.
Kawakita, A., et al., Allergy 67: 371-379; 2012.
Kelly, G.S Alt. Med. Rev. 3 : 114-127 ; 1998.
Kim, A., et al., Biomaterials 25: 305-313; 2004.
Kim, S.T., et al., J. Gene Med. 11: 26-37; 2009.
Kimball, S.M., et al., Am. J. Clin. Nutr. 86: 645-651; 2007.

\* cited by examiner

FIGURES
FIG. 1A
FIG. 1B
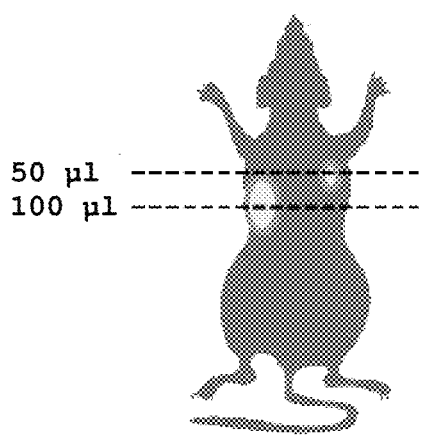
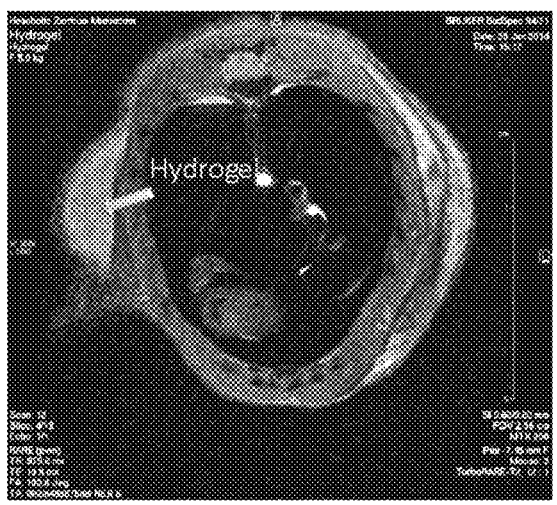
FIG. 2
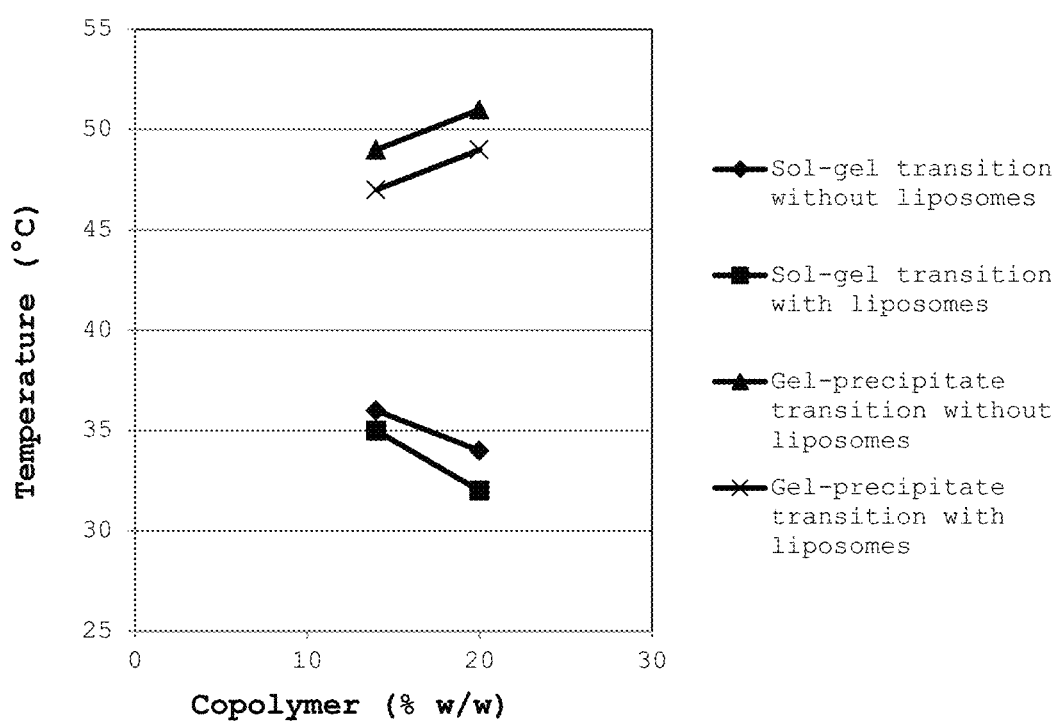

FIG. 11

Human TNF-alpha receptor 1 (TNFR1), DNA sequence

```
   1 ctcctccagc tcttcctgtc ccgctgttgc aacactgcct cactcttccc ctcccacctt
  61 ctctccctc ctctctgctt taattttctc agaattctct ggactgaggc tccagttctg
 121 gcctttgggg ttcaagatca ctgggaccag gccgtgatct ctatgcccga gtctcaaccc
 181 tcaactgtca ccccaaggca cttgggacgt cctggacaga ccgagtcccg ggaagcccca
 241 gcactgccgc tgccacactg ccctgagccc aaatggggga gtgagaggcc atagctgtct
 301 ggcatgggcc tctccaccgt gctgacctg ctgctgccac tggtgctcct ggagctgttg
 361 gtgggaatat accctcagg ggttattgga ctggtccctc acctagggga cagggagaag
 421 agagatagtg tgtgtcccca aggaaaatat atccaccctc aaaataattc gatttgctgt
 481 accaagtgcc acaaaggaac ctacttgtac aatgactgtc caggcccggg gcaggatacg
 541 gactgcaggg agtgtgagag cggctccttc accgcttcag aaaaccacct cagacactgc
 601 ctcagctgct ccaaatgccg aaaggaaatg ggtcaggtgg agatctcttc ttgcacagtg
 661 gaccgggaca ccgtgtgtgg ctgcaggaag aaccagtacc ggcattattg gagtgaaaac
 721 cttttccagt gcttcaattg cagcctctgc ctcaatggga ccgtgcacct ctcctgccag
 781 gagaaacaga acaccgtgtg cacctgccat gcaggtttct ttctaagaga aaacgagtgt
 841 gtctcctgta gtaactgtaa gaaaagcctg gagtgcacga agttgtgcct accccagatt
 901 gagaatgtta agggcactga ggactcaggc accacagtgc tgttgcccct ggtcattttc
 961 tttggtcttt gccttttatc cctcctcttc attggtttaa tgtatcgcta ccaacggtgg
1021 aagtccaagc tctactccat tgtttgtggg aaatcgacac ctgaaaaaga gggggagctt
1081 gaaggaacta ctactaagcc cctggcccca aacccaagct tcagtcccac tccaggcttc
1141 accccacccc tgggcttcag tcccgtgccc agttccacct tcacctccag ctccacctat
1201 accccggtg actgtcccaa ctttgcggct ccccgcagag aggtggcacc accctatcag
1261 ggggctgacc ccatccttgc gacagccctc gcctccgacc ccatcccaa ccccttcag
1321 aagtgggagg acagcgccca caagccacag agcctagaca ctgatgaccc cgcgacgctg
1381 tacgccgtgg tggagaacgt gccccgttg cgctggaagg aattcgtgcg gcgcctaggg
1441 ctgagcgacc acgagatcga tcggctggag ctgcagaacg ggcgctgcct gcgcgaggcg
1501 caatacagca tgctggcgac ctggaggcgg cgcacgccgc ggcgcgaggc cacgctggag
1561 ctgctgggac gcgtgctccg cgacatggac ctgctgggct gcctgaggga tcgaggag
1621 gcgctttgcg gccccgccgc cctccgccc gcgcccagtc ttctcagatg aggctgcgcc
1681 cctgcgggca gctctaagga ccgtcctgcg agatcgcctt ccaaccccac tttttctgg
1741 aaaggagggg tcctgcaggg gcaagcagga gctagcagcc gcctacttgg tgctaacccc
1801 tcgatgtaca tagctttttct cagctgcctg cgcgccgccg acagtcagcg ctgtgcgcgc
1861 ggagagaggt gcgccgtggg ctcaagagcc tgagtgggtg gtttgcgagg atgagggacg
1921 ctatgcctca tgcccgtttt gggtgtcctc accagcaagg ctgctcgggg gccctggtt
1981 cgtccctgag ccttttcac agtgcataag cagttttttt tgtttttgtt ttgttttgtt
2041 ttgtttttaa atcaatcatg ttacactaat agaaacttgg cactcctgtg ccctctgcct
2101 ggacaagcac atagcaagct gaactgtcct aaggcagggg cgagcacgga acaatgggc
2161 cttcagctgg agctgtggac ttttgtacat acactaaaat tctgaagtta aagctctgct
2221 cttggaaaaa aaaaaaaaa aaaaaaaaa aaaaaaa
```

FIG. 12A

Murine IL-4, native form, DNA sequence

```
  1 CATATCCACG GATGCGACAA AAATCACTTG AGAGAGATCA TCGGCATTTT GAACGAGGTC
 61 ACAGGAGAAG GGACGCCATG CACGGAGATG GATGTGCCAA ACGTCCTCAC AGCAACGAAG
121 AACACCACAG AGAGTGAGCT CGTCTGTAGG GCTTCCAAGG TGCTTCGCAT ATTTTATTTA
181 AAACATGGGA AAACTCCATG CTTGAAGAAG AACTCTAGTG TTCTCATGGA GCTGCAGAGA
241 CTCTTTCGGG CTTTTCGATG CCTGGATTCA TCGATAAGCT GCACCATGAA TGAGTCCAAG
301 TCCACATCAC TGAAAGACTT CCTGGAAAGC CTAAAGAGCA TCATGCAAAT GGATTACTCG
361 TAG
```

Murine IL-4, native form, translated protein sequence

```
  1 HIHGCDKNHL REIIGILNEV TGEGTPCTEM DVPNVLTATK NTTESELVCR ASKVLRIFYL
 61 KHGKTPCLKK NSSVLMELQR LFRAFRCLDS SISCTMNESK STSLKDFLES LKSIMQMDYS
121 *
```

FIG. 12B

Murine IL4, QY mutant construct, DNA sequence

```
  1 ATGGGTAGCA GCCATCATCA TCATCATCAC TCCAGCGGTC TGGTTCCTCG TGGTAGTCAT
 61 ATGCACATTC ACGGGTGTGA CAAAAATCAT CTGCGCGAGA TTATCGGTAT TCTGAACGAA
121 GTGACCGGAG AAGGCACTCC TTGTACGGAA ATGGATGTCC CGAACGTCCT GACAGCGACG
181 AAAACACAA CGGAATCGGA ACTGGTTTGC CGTGCCAGCA AAGTCCTGCG CATCTTCTAT
241 CTGAAACATG GTAAAACGCC GTGTCTGAAA AAAACAGCA GCGTTCTGAT GGAACTGCAA
301 CGCCTGTTTC GTGCTTTCCG CTGCCTGGAT AGCAGTATCA GCTGTACGAT GAACGAGTCC
361 AAATCAACCT CCCTGAAAGA CTTCCTGGAA TCACTGAAAT CGATCATGGA TATGGATGAC
421 AGCTGATAA
```

Murine IL4, QY mutant construct, translated protein sequence

```
  1 MGSSHHHHHH SSGLVPRGSH MHIHGCDKNH LREIIGILNE VTGEGTPCTE MDVPNVLTAT
 61 KNTTESELVC RASKVLRIFY LKHGKTPCLK KNSSVLMELQ RLFRAFRCLD SSISCTMNES
121 KSTSLKDFLE SLKSIMDMDD S*
```

INDUCTION OF ANTIGEN-SPECIFIC TOLERANCE BY PERIPHERAL PHAGOCYTOSIS

BACKGROUND OF THE INVENTION

For the treatment of allergy, asthma and autoimmune diseases including type I diabetes, rheumatoid arthritis, and multiple sclerosis, allergen- or antigen-specific immunotherapy has the potential of restoring lasting immunological tolerance, but adjuvant strategies are needed to increase the efficacy of this approach.

One promising adjuvant strategy is the use of apoptotic cells. For example, infusion of peptides cross-linked to the surface of apoptotic splenic leukocytes using ethylene carbodiimide has been demonstrated to be a highly efficient method for inducing antigen-specific T cell tolerance for treatment of autoimmune diseases (Jenkins and Schwartz, 1987; Getts et al., 2011). A single intravenous injection of syngeneic splenocytes coupled with encephalitogenic myelin peptides/proteins has been shown to induce antigen-specific tolerance in experimental autoimmune encephalomyelitis (e.g., Tan et al., 1991). Promising results were also obtained in a recent phase 1 clinical trial in multiple sclerosis patients using seven myelin peptides coupled with the chemical crosslinker EDC (1-ethyl-3-(3-dimethylaminopropyl)-carbodiimide) to autologous peripheral blood mononuclear cells (PBMCs) (Lutterotti et al., 2013).

The exact mechanism of tolerization with antigens coupled to the surface of cells with EDC is not fully understood, but there is evidence that several mechanisms are involved. On the one hand it has been shown that antigen-specific T cells encountering their cognate antigen/MHC complexes on EDC-treated cells are anergized as a result of failure to receive adequate CD28-mediated costimulation (Jenkins and Schwartz, 1987). On the other hand, a potentially more important mechanism is based on the fact that EDC efficiently induces apoptosis in treated cells. Experiments in animal models suggest that i.v. injected apoptotic EDC-treated cells are phagocytosed in the spleen within a few hours by antigen-presenting cells (monocytes/macrophages and/or immature dendritic cells) leading to the production of IL-10 and expression of PD-L1 (programmed cell death 1 ligand; CD274) on macrophages which appears to be regulated by IL-10 in possibly autocrine fashion (Getts et al., 2011). The production of IL-10 by macrophages upon phagocytosis of apoptotic cells is in agreement with results of a previous study which has shown that feeding of peripheral blood-derived macrophages with apoptotic cells triggers the production in IL-10 (Voll et al., 1997).

Both the production of IL-10 and the expression of PD-L1 on macrophages are important factors for the induction of tolerance. IL-10 plays an important immune regulatory role, preventing inflammatory immune responses and the development of autoimmunity. Importantly, neither IL-10-deficient mice nor mice treated with anti-IL-10 can be tolerized with ethylene carbodiimide-fixed splenocytes (Getts et al., 2011). PD-L1 mediates T cell-negative costimulation. The formation of PD-1 receptor/PD-L1 ligand complex transmits an inhibitory signal which reduces the proliferation of CD8+ T cells at lymph nodes. Furthermore, PD-1 is also able to control the accumulation of foreign antigen-specific T cells in lymph nodes through apoptosis (Chemnitz et al., 2004). PD-L1 upregulation on macrophages appears to be as important as the production of IL-10 since PD-L1 blockade at the time of injection of syngeneic splenocytes coupled with encephalitogenic myelin peptides/proteins abrogated tolerance induction (Getts et al., 2011).

However, the therapeutic use of antigenic peptides/proteins coupled via EDC to autologous peripheral blood mononuclear cells has also considerable limitations. First, the manufacturing process for antigen-coupled cells requires experienced handling under GMP conditions in clean rooms and, thereby, is likely to be limited to major clinical institutions such as university hospitals. Second, therapeutic preparations have to be established individually for each patient, which is laborious and cost-intensive. Third, treatment of the cells with EDC is likely to induce apoptosis only in a portion of the cells due to a varying degree of derivatization with this crosslinker and, thereby, introduces a variable factor to this approach that is difficult to control. There is no question that alternative approaches based on phagocytosis of apoptotic cells are needed which provide a comparable therapeutic efficacy, but avoid the above mentioned limitations.

Immuno-Modulating Effects of Phosphatidy-L-Lserine (PS)-Containing Liposomes.

In viable cells, PS is kept exclusively on the inner leaflet of the lipid bilayer via ATP-dependent translocases. In apoptotic cells, the concentration of PS on the outer leaflet of the lipid bilayer is estimated to increase by more than 280-fold within only a few hours after induction of apoptosis. PS exposed on the surface of apoptotic cells represents the key signal for triggering phagocytosis by macrophages (for a review, see Hochreiter-Hufford and Ravichandran, 2013). This is indicated by the observation that macrophage phagocytosis of apoptotic lymphocytes was inhibited in a dose-dependent manner by PS and PS-containing liposomes, but not by liposomes containing other anionic phospholipids including phosphatidyl-D-serine (Fadok et al., 1992).

Furthermore, several studies suggest that liposomes containing PS have the potential to mimic the anti-inflammatory effect of apoptotic cells and, therefore, could serve in some aspects as substitutes of antigen-loaded apoptotic cells. PS-containing liposomes have been shown to exert inhibitory effects on certain macrophage functions in vitro (Kornbluth, 1994). For example, PS-containing liposomes inhibited the IFN-γ-mediated induction of anti-leishmanial activity in murine macrophages (Gilbreath et al., 1985). In vivo effects of PS and PS-containing liposomes have also been reported (Kornbluth, 1994). For example, intravenous injection of PS in mice has been demonstrated to reduce both T cell-dependent and T cell-independent antibody production (Ponzin et al., 1989) and intravenous injection of PS prior to the injection of bacterial lipopolysaccharide has been shown to reduce serum TNF-α levels (Monastra and Bruni, 1992). Comparable effects have been observed also after injection of PS-containing liposomes. For example, intraperitoneal injection of PS-containing liposomes ameliorated the course of extrinsic allergic encephalitis induced in mice by immunization with myelin basic protein (Monastra et al., 1993). Also, PS-containing liposomes specifically inhibited responses in mice to antigens as determined by decreased draining lymph node tissue mass, reduced numbers of total leukocytes and antigen-specific CD4+ T cells and decreased levels of antigen-specific IgG in blood. TGF-β appears to play a critical role in this inhibition, as the inhibitory effects of PS-containing liposomes were reversed by in vivo administration of anti-TGF-β antibodies (Hoffmann et al., 2005). A recent study demonstrated that after uptake of PS-containing liposomes in vitro and in vivo macrophages secrete high levels of the anti-inflammatory cytokines TGF-β and IL-10 and upregulate the expression of CD206 (mannose receptor C type 1; MRC1), concomitant with downregulation of proinflammatory markers such as TNFα and the surface marker CD86 (Harel-Adar et al., 2011). CD86 (also known as B7-2) is a protein expressed on antigen-presenting cells that provides costimulatory signals necessary for T cell activation and survival. In subsequent experiments, the authors demonstrated that modulation of cardiac macrophages by PS-containing liposomes improves infarct repair. Injection of PS-containing liposomes via the femoral vein in a rat model of acute myocardial infarction promoted angiogenesis and prevented ventricular dilatation and remodeling (Harel-Adar et al., 2011).

Application of PS-Containing Liposomes as Tolerance-Promoting Adjuvants for Antigen- or Allergen-Specific Immunotherapy.

While the above listed studies indicate that PS-containing liposomes can inhibit immune responses of antigen-specific CD4+ T cells and B cells in vivo, their potential as tolerance-promoting adjuvants for current approaches of antigen- or allergen-specific immunotherapy is limited for several reasons.

Most important for a tolerance-promoting effect of PS-containing liposomes is their presence at therapeutically effective concentrations in the local microenvironment of the site of antigen or allergen presentation (e.g., subcutaneous location) for an extended period of time, at least as long as the development of immunologic memory requires upon antigen or allergen exposure. Both requirements, however, pose serious problems.

Studies with apoptotic antigen-coupled splenocytes (Ag-SP) have demonstrated that tolerance induction requires intravenous (i.v.) injection of Ag-SP, since intraperitoneal (i.p.) and especially subcutaneous (s.c.) injection of Ag-SP failed to prevent disease development (Getts et al., 2011). It is thought that in particular s.c. injection of Ag-SP triggers uptake and activation of resident leukocyte populations such as Langerhans cells, dermal dendritic cells, and/or γδ-T cells, resulting in the production of proinflammatory cytokines. Most likely, this response negates the upregulation of negative costimulatory molecules such as CTLA-4 and PD-L1, both of which play an important role in Ag-SP tolerance induction (Eagar et al., 2002; Fife et al., 2006). Based on these data, a tolerance-promoting effect of PS-containing liposomes at a peripheral site of antigen or allergen presentation will require concomitant local suppression of proinflammatory cytokines. At this point, however, there is no technology for concomitant local suppression of proinflammatory cytokines available.

The other problem is the period of time necessary for the development of immunologic memory upon antigen or allergen exposure which requires the engagement of the T cell receptor (TCR) over 12-48 hours. Long lasting memory may even require repetitive exposure. Accordingly, tolerance-promoting therapeutics may need to be in effect at least for the same period of time at the site of antigen or allergen presentation, most likely as long as antigens or allergens are released from the injected antigen/allergen-adjuvant complex. However, this requires repeated local injections at the site of antigen or allergen presentation of PS-containing liposomes, inhibitors of proinflammatory cytokines and combinations of 'find me' signals, a procedure that is not acceptable for physicians and patients.

Furthermore, 'find me' signals in addition to surface-exposed PS may be required to trigger effective local phagocytosis and, thereby, to enhance the tolerance-promoting effect of PS-containing liposomes. The role of 'find me' signals is to establish a chemotactic gradient stimulating the migration of phagocytes to the apoptotic cells. To date, several proposed 'find me' signals released by dying cells have been reported including fractalkine (i.e., chemokine CXC3CL1, a membrane associated protein that is proteolytically released from apoptotic B cells), lysophosphatidylcholine (LPC, released from apoptotic cells by caspase-3-dependent activation of phospholipase A2), sphingosine-1-phosphate (SiP, produced by sphingosine kinase 1) and the nucleotides ATP and UTP, the release of which is mediated via the pannexin channels (for a review, see Hochreiter-Hufford and Ravichandran, 2013). Because nucleotides are readily degraded by extracellular nucleotidases, they are unlikely to serve long as 'find me' signals to phagocytes in circulation. Rather, they attract tissue resident macrophages (Rachivandran, 2010). It is currently unclear whether these 'find me' signals function together in an additive or synergistic manner during the phagocyte attraction, but local administration of such 'find me' signals at the site of antigen or allergen presentation is problematic since especially low molecular weight 'find me' signals such as LCP, SiP, ATP and UTP are rapidly eliminated at the site of antigen or allergen presentation due to diffusion and fast degradation. Thereby, single local injections of 'find me' signals cannot establish chemotactic gradients which are comparable to those established by the continuing release of 'find me' signals from apoptotic cells.

As evident from the foregoing, there is a need for suitable approaches that enable tolerance-promoting effects of PS-containing liposomes as adjuvant strategy of antigen- or allergen-specific immunotherapy for the treatment of different allergic and autoimmune diseases in the local microenvironment of the site of antigen or allergen presentation

SUMMARY OF THE INVENTION

For solving this problem the invention teaches the subject matters of the claims, specifically by disclosing methods for sustained local delivery at the site of antigen or allergen presentation of PS-containing liposomes at therapeutically effective concentrations, various combinations of 'find me' signals, and various combinations of immune modulators capable of inhibiting unwanted local immune reactions at the site of antigen or allergen presentation.

For the treatment of allergy, asthma and autoimmune diseases including type I diabetes, rheumatoid arthritis, and multiple sclerosis, allergen- or antigen-specific immunotherapy has the potential of restoring lasting immunological tolerance, but adjuvant strategies are needed to increase the efficacy of this approach.

The present invention provides methods for restoring lasting immunological tolerance in patients suffering from allergy, allergic asthma, type I diabetes, rheumatoid arthritis, and multiple sclerosis, by treatment with allergen- or antigen-specific immunotherapy in combination with tolerance-promoting PS-containing liposomes, various combinations of 'find me' signals for efficient peripheral phagocytosis, various combinations of 'eat me' signals for enhanced phagocytosis, and individual combinations of Treg-modulating therapeutics capable of inhibiting unwanted local immune reactions at the site of antigen or allergen presentation.

In one embodiment, the present invention discloses phosphatidyl-L-serine (PS)-containing liposomes capable of inhibiting immune responses of antigen-specific CD4+ T cells and B cells in vivo. PS-containing liposomes include but are not limited to PS-containing liposomes which are empty, PS-containing liposomes which contain one or more enclosed antigens or autoallergens, or one or more fragments thereof, or one or more allergen extracts in the presence or absence of suitable adjuvants, and PS-containing liposomes which contain one or more surface-attached antigens or autoallergens, or one or more surface-attached fragments thereof, or one or more surface-attached allergen extracts.

In another embodiment, the present invention discloses suitable matrices for sustained local delivery of PS-containing liposomes capable of inhibiting immune responses of antigen-specific CD4+ T cells and B cells in vivo at the site of antigen or allergen presentation along with a prolonged presentation of allergens or antigens or fragments thereof. Preferred matrices include but are not limited to biodegradable polymers which are suitable as depot for substantial quantities of PS-containing liposomes, which allow the release of sufficient quantities of such liposomes for efficient local inhibition of immune responses of antigen-specific CD4+ T cells and B cells over a prolonged period of time, and which are chemically and physically compatible with the different types of PS-containing liposomes or mixtures of adjuvant(s) and allergen (s) or antigen(s) or fragments thereof used for the induction of tolerance according to the method of the present invention. Preferred are injectable in situ-forming gel systems which are biodegradable, are used for controlled delivery of PS-containing liposomes capable of inhibiting immune responses of antigen-specific CD4+ T cells and B cells. Such in situ-forming gel systems (hydrogels) undergo a sol-gel-sol transition, which is free flowing sol at room temperature and a non-flowing gel at body temperature. Compared to other biodegradable polymers, the injectable thermo-gelling polymers possess several advantages including easy preparation, high encapsulation efficiency of bioactive preparations such as PS-containing liposomes, and free of harmful organic solvents in the formulation process.

In another embodiment, the present invention discloses 'find me' signals capable of triggering effective local phagocytosis, thereby enhancing the tolerance-promoting effect of PS-containing liposomes. Suitable 'find me' signals include but are not limited to fractalkine (chemokine CXC3CL1), lysophosphatidylcholine (LPC), sphingosine-1-phosphate (SiP) and the nucleotides ATP and UTP. Preferred are 'find me' signals which can be embedded in substantial quantities in matrices selected for controlled delivery of PS-containing liposomes, which are chemically and physically compatible with such matrices, and which are released from such matrices over a prolonged period of time.

In another embodiment, the present invention discloses 'eat me' signals capable of triggering effective local phagocytosis, thereby further enhancing the tolerance-promoting effect of PS-containing liposomes. Suitable liposomal surface-attached 'eat me' signals include but are not limited to intercellular adhesion molecule 3 (ICAM3), oxidized low-density lipoprotein particle (OxLDL), calreticulin, and annexin I. Suitable 'eat me' signals functioning as adaptor proteins between PS-containing liposomes and receptor molecules on phagocytes include but are not limited to annexin A1, β2-glycoprotein I (β2GP1), the growth arrest-specific gene product 6 (Gas6), the milk-fat globule EGF-factor 8 (MFG-E8), and protein S. Other potentially suitable 'eat me' signals functioning as adaptor proteins include thrombospondin, complement protein C1q, c-reactive protein (CRP), Immunoglobulin M (IgM), and mannose binding lectin (MBL). Preferred are 'eat me' which can be embedded in substantial quantities in matrices selected for controlled delivery of PS-containing liposomes, which are chemically and physically compatible with such matrices, and which are released from such matrices over a prolonged period of time.

In another embodiment, the present invention discloses liposomal surface-attached ligands capable of supporting the tolerance-promoting effect of PS. Such ligands include but are not limited to ligands of B cell inhibitory coreceptors such as CD22 and SIGLEC-10 (SIGLEC-G in mice), and mannose or oligomannose.

In another embodiment, PS-containing liposomes are modified by encapsulation of one or more mediators of macrophage-induced immune suppression including but not limited to microRNA-21 (miR-21) and resolvin D1.

In another embodiment, the present invention discloses low or medium molecular weight molecules capable of modulating the induction of Tregs ('immune modulators') in order to inhibit unwanted local immune reactions at the site of antigen or allergen presentation. Suitable 'immune modulators' include but are not limited to molecules targeting complement-mediated pathways, TNF-alpha-mediated pathways, vitamin D3-mediated pathways, and IL-4/IL-13-mediated pathways. Suitable low molecular weight complement inhibitors include but are not limited to those targeting complement protein C3 and interactions of the anaphylatoxins C3a and C5a with their respective receptors. Suitable low to medium molecular weight inhibitors of TNFR1 or TNFR1-mediated include but are not limited a) to molecules capable of specific inhibition of sTNF so that the mTNF-TNFR1 and mTNF-TNFR2 interactions remain intact such as dominant-negative sTNF mutants, b) molecules capable of specific inhibition of TNFR1 while leaving TNFR2 signaling intact such as antagonistic TNF mutants with specificity for TNFR1, antisense oligonucleotides with specificity for TNFR1, aptamers with specificity for TNFR1, and oligonucleotides capable of TNFR1 silencing via RNAi, and c) molecules capable of inhibiting TNFR1-mediated pathways including such as S-methylglutathione, pro-glutathione drugs (e.g., N-acetylcysteine), and salicylates. Suitable low molecular weight molecules which are capable of modulating the induction of Tregs via vitamin D-mediated pathways include but not limited to a) active vitamin D3 (calcitriol; 1,25-$(OH)_2$D3), b) its inactive form (cholecalciferol; 25(OH)D3), c) vitamin D3 analogues such as 19-nor-vitamin D analogues, 24-hydroxy vitamin D derivatives, and 1α-hydroxyvitamin D3, and d) non-secosteroidal vitamin D receptor (VDR) modulators. Suitable low to medium molecular weight molecules which are capable of modulating the induction of Tregs via inhibition of IL-4/IL-13-mediated pathways include but not limited to a) antagonistic IL-4 and IL-13 derivatives, b) aptamers with specificity for IL-4 and IL-13 capable of blocking their biologic activity, c) aptamers with specificity for IL-4 and IL-13 receptor complexes capable of blocking the interaction of IL-4 and IL-13 with their receptor subunits, and d) monoclonal antibodies fragments or other medium molecular weight proteinaceous constructs with specificity for IL-4 and IL-13 receptor complexes capable of blocking the interaction of IL-4 and IL-13 with their receptor subunits.

In another embodiment, one or more 'immune modulators' are employed for the method of the present invention which can be embedded in substantial quantities in matrices selected for controlled delivery of PS-containing liposomes, which are chemically and physically compatible with such matrices, and which are released from such matrices over a prolonged period of time. Preferred are low to medium molecular weight 'immune modulators' which provide a relatively short serum half-life that is sufficient to be locally active upon their release from a depot at the site of antigen or allergen presentation, and which allows fast removal from circulation upon diffusion and transport away from the site of antigen or allergen presentation. Thereby, stimulation of Treg induction is restricted mainly to the site of antigen or allergen presentation and adverse effects due to interaction of 'immune modulators' with targets distal from the site of antigen or allergen presentation are reduced. Suitable therapeutics providing such characteristics include but are not limited to a) oligopeptide-based complement inhibitors, b) oligonucleotide-based therapeutics for the inhibition of TNF-alpha-mediated pathways, IL-4/IL-13-mediated pathways and complement-mediated pathways, c) glutathione-, salicylate- and oligonucleotide-based therapeutics for the inhibition of TNFR1-mediated pathways, d) selected vitamin D3 analogs such as calipotriol, and e) low to medium molecular weight proteins such as IL-4 muteins and TNF-alpha mutants.

In another embodiment, the present invention discloses adjuvants for allergen or antigen presentation according to the method of the present invention. If IL-4/IL-13 inhibitors are included in the treatment protocols, adjuvants are suitable which elicit Th2-type immune responses including but are not limited to aluminum salts, Montanide emulsions (squalene-based water-in-oil emulsions) and polyphosphazenes. If vitamin D3 or analogs thereof are included in the treatment protocols, adjuvants are also suitable which elicit Th1-type immune responses including but are not limited to monophosphoryl lipid A (MPL) and CpG oligonucleotides. Adjuvants eliciting a combined Th1- and Th2-type immune response may also be used for the method of the present invention if inhibitors of IL-4- and IL-13-mediated pathways and vitamin D3 or analogs thereof are included in the treatment protocols. Suitable adjuvants eliciting a combined Th1-type and Th2-type immune response include but are not limited to squalene-based oil-in-water emulsions, granulocyte-macrophage colony stimulating factor (GM-CSF), and adjuvants based on inulin and virosomes.

In another embodiment, the present invention discloses the application of compositions for the treatment of patients suffering from allergy, allergic asthma or various autoimmune diseases including but not limited to type 1 diabetes, rheumatoid arthritis, juvenile idiopathic arthritis, and multiple sclerosis, wherein compositions for local and systemic applications are included.

For local applications, compositions comprise one or more matrices suitable for sustained local delivery of PS-containing liposomes, optionally 'find me', optionally 'eat me' signals, and optionally one or more low or medium molecular weight 'immune modulators' capable of stimulating the induction of Tregs, in combination with local autoantigen- or allergen-specific immunotherapy, wherein the allergen(s) or autoantigen(s) or fragments thereof are administered in the presence or absence of suitable adjuvants, optionally embedded in PS-containing liposomes or optionally displayed on the surface of PS-containing liposomes. Suitable 'immune modulators' for local treatment procedures are those which are beneficial for individual pathological conditions. Compositions comprising low molecular weight complement inhibitors are applied preferably for the treatment of patients having a complement-associated condition and/or for which inhibition of complement at the C3 level or inhibition of C3a and C5a signaling is beneficial. Compositions comprising low to medium molecular weight inhibitors of TNFR1 or TNFR1-mediated functions are applied preferably for the treatment of patients having a TNF-alpha-related condition and/or for which enhanced mTNF-TNFR2 signaling by specific inhibition of TNFR1-mediated signaling is beneficial. Compositions comprising low molecular weight molecules capable of modulating the induction of Tregs via vitamin D-mediated pathways are applied preferably for the treatment of patients having an autoimmune disease related to vitamin D deficiency and/or for which vitamin D, analogs thereof or low molecular weight VDR modulators are beneficial. Compositions comprising low or medium molecular weight inhibitors of IL-4/IL-13-mediated pathways are applied preferably for the treatment of patients having a Th2-related condition and/or which are treated with therapeutics including adjuvants promoting Th2 immune responses.

For systemic applications, compositions comprise one or more allergens or autoantigens, or fragments thereof, or one or more allergen extracts, either embedded in PS-containing liposomes or covalently attached to the surface of PS-containing liposomes. Optionally, these liposomes may expose one or more surface-attached 'eat me' signals.

In another embodiment, the present invention discloses compositions for one-step and two-step immunotherapeutic procedures for locally restricted treatment procedures. One-step administration procedures for locally restricted treatment procedures comprise one or more matrices suitable for mediating sustained delivery of one or more allergens/autoantigens or fragments thereof, tolerance-promoting PS-containing liposomes, and individual combinations of one or more Treg-modulating therapeutics capable of inhibiting unwanted local immune reactions at the site of allergen/autoantigen presentation. The allergens/autoantigens or fragments thereof can be either embedded in the matrix in the presence or absence of one or more suitable adjuvants, or encapsulated in PS-containing liposomes, or attached to the surface of PS-containing liposomes. In order to enforce the uptake of PS-containing liposomes by macrophages, one or more 'find me' signals and one ore more 'eat me' signals can be added to the composition.

Two-step administration procedures for locally restricted treatment procedures include administration of composition A comprising one or more allergens/autoantigens or one or more fragments thereof, and optionally one or more adjuvants, followed by administration of composition B at the site of administered composition A, comprising one or more matrices suitable for mediating sustained delivery of tolerance-promoting PS-containing liposomes, and individual combinations of one or more Treg-modulating therapeutics capable of inhibiting unwanted local immune reactions at the site of allergen/autoantigen presentation. In order to enforce the uptake of PS-containing liposomes by macrophages, one or more 'find me' signals and one ore more 'eat me' signals can be added to the composition B.

In another embodiment, the present invention discloses methods for incorporating compositions into pharmaceutical formulations suitable for administration.

In yet another embodiment, the present invention discloses therapeutic methods including therapeutic applications of suitable compositions, the determination of therapeutically effective doses, and modes of administration for the induction of allergen or autoantigen tolerance using the compositions of the present invention.

Specific preferred embodiments of the present invention will become evident from the following more detailed description and the claims.

BRIEF DESCRIPTION OF THE DRAWINGS

FIGS. 1A and 1B show in vivo gelation of PLGA-PEG-PLGA hydrogels. FIG. 1A shows the injection of the gel solution into a hairless mouse (strain SKH1) at two points in amounts of 50 and 100 µl; FIG. 1B shows the magnetic resonance imaging (MRI) of the mouse after 2 hours of being injected with the gel solution To test the in vivo gel formation behavior of PLGA-PEG-PLGA hydrogels of Example 1.1., the hydrogel is injected subcutaneously into mice. An aliquot of 240 µl of a 18% PLGA-PEG-PLGA blockpolymer solution in water is mixed with 30 µl of 10× PBS (pH 7.4) buffer and 30 µl of 30 mM morpholino ethanesulfonic acid (MES) buffered solution (pH 6.0) at room temperature. The gel solution is injected into hairless mouse (strain SKH1), euthanized by cervical dislocation and kept in 37° C. pad, at two sites in amounts of 50 and 100 µl (see FIG. 1A). After 2 hours the gels are analyzed in the mouse by magnetic resonance imaging (MRI), using a Bruker BioSpec 9421 instrument (see FIG. 1B).

FIG. 2 shows the gelation characteristics of PLGA-PEG-PLGA/PS-liposome composites.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1. Synthesis of unilamellar PS-liposomes from a lipid mixture of phosphatidyldserine (PS), phosphatidylcholine (PC), and cholesterol (CH) at a ratio of 30:30:40 PS to PC to CH according to Hoffmann et al. (2005) is described in Example 2.2.

For determination of gelation characteristics of PLGA-PEG-PLGA/PS-liposome composites, transparent vials are filled with 100 µl water containing different concentrations of the copolymer of Example 2.1. (22.5% w/w, and 30% w/w), cooled to 4° C. and mixed with 50 µl PBS containing liposomes of Example 2.2 (6.7 µmol lipid) or 50 µl PBS containing no liposomes. The final concentrations of the copolymer are 15% w/w and 20% w/w containing liposomes at a concentration of 22.3 µmol lipid/ml (13.1 mg/ml). The vials are placed in a water bath and each solution is heated in 1° C. steps beginning at 26° C. in a thermomixing device (Eppendorf). At each temperature step the gelation is checked by careful inversion of the tube. When the solution is not free-flowing, gelation of the solution occurred, the temperature read from the thermometer is determined as gelation temperature.

Figure 3:
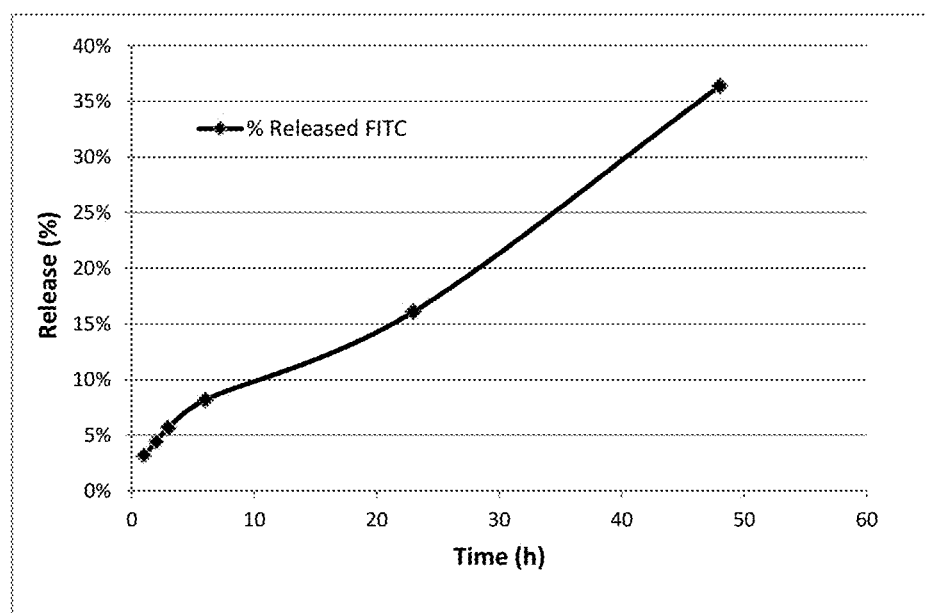

FIG. 3 shows the release of FITC-BSA containing PS-liposomes from PLGA-PEG-PLGA/PS-liposome composites.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1. Synthesis of unilamellar FITC-BSA containing PS-liposomes from a lipid mixture of phosphatidyldserine (PS), phosphatidylcholine (PC), and cholesterol (CH) at a ratio of 30:30:40 PS to PC to CH according to Hoffmann et al. (2005) is described in Example 4.2.

For determination of the in vitro release of FITC-BSA containing PS-liposomes from PLGA-PEG-PLGA/PS-liposome composites, vials are filled with 200 µl water containing 22.5% (w/w) of the copolymer of Example 2.1., cooled to 4° C. and mixed with 100 µl PBS containing liposomes of Example 4.2 (6.7 µmol lipid). The final concentrations of the copolymer is 15% containing liposomes with encapsulated FITC-BSA at a concentration of 22.3 µmol lipid/ml (13.1 mg/ml). The concentration of embedded BSA-FITC was calculated from the difference of the initial concentration and remaining concentration in the supernatant of the liposome suspension after encapsulation and washing. The efficacy of encapsulation was 22%, resulting in 220 µg/ml BSA-FITC in liposome suspension. The reaction mixtures are incubated at 37° C. under mild agitation in a water bath until gelling. Thereafter, 1 ml of phosphate-buffered saline (PBS) pH 7.4 is added to each sample and incubation at 37° C. is continued. At specified sample collection times the supernatant are withdrawn and replaced by an identical volume of PBS pH 7.4 to maintain release conditions. The amount of released PS-liposomes is determined by measuring encapsulated FITC-BSA via fluorescence spectroscopy in an ELISA reader (Tecan GENios) in the supernatant after dissolving the lipid vesicles with 1% (v/v) Triton X-100 (Cohen et al., 1991). The release was calculated in comparison to theoretical maximal release.

Figure 4:
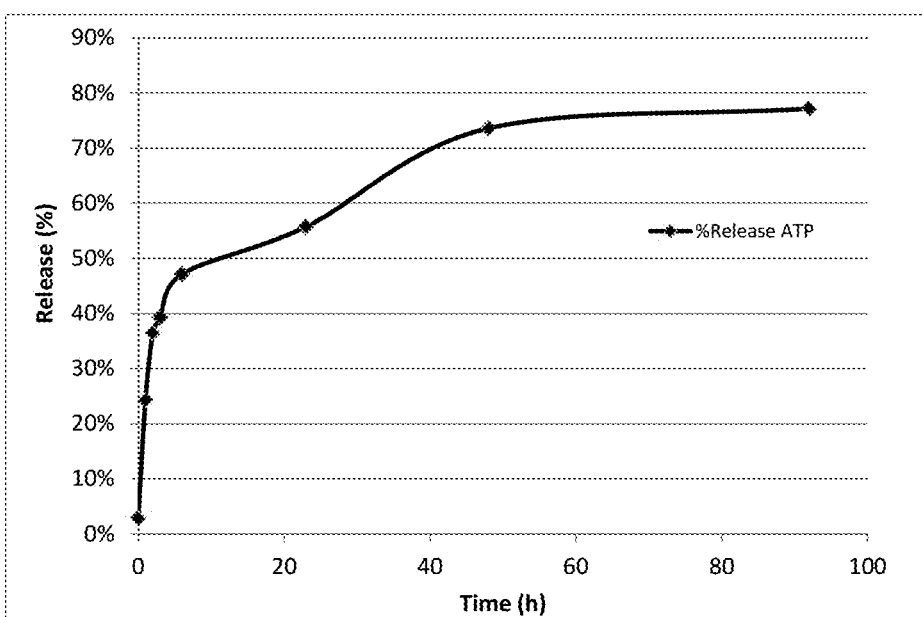

FIG. 4 shows the release of the immune modulator of phagocytosis ATP from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of ATP from PLGA-PEG-PLGA hydrogels, a stock solution of 10 mM ATP is prepared. An aliquot of 20 µl of the stock solution (10 mM ATP) is combined with 160 µl of 25% gel solution and 20 µl of 10× PBS. The mixture is incubated for 2 minutes at 37° C. to induce gelling and overlayed with 1 ml of 1× PBS. At frequent timepoints the supernatant is removed by pipetting and stored at 4° C. The removed supernatant is replaced by fresh 1 ml of 1× PBS. After 48 hours the samples are measured spectrometrically at 260 nm and the amount of released ATP is calculated as percentage of a reference sample containing a concentration of ATP equaling 100% release.

Figure 5:
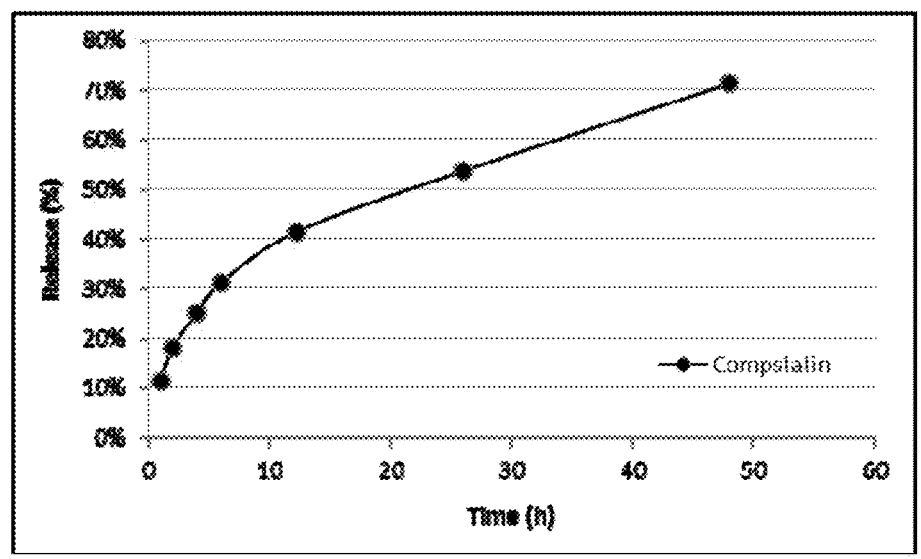

FIG. 5 shows the release of complement inhibitor compstatin from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of compstatin from PLGA-PEG-PLGA hydrogels, a stock solution of 2 mg/ml in 30% acetonitrile of the 13-residue cyclic peptide compstatin (H-I[CVVQDWGHHRC]T-NH2; Tocris Bioscience, UK) is prepared. An aliquot of 20 µl of the stock solution is combined with 160 µl of 25% gel solution and 20 µl of 10× PBS. The mixture is incubated for 2 minutes at 37° C. to induce gelling and overlayed with 200 µl of 1× PBS. At frequent time points the supernatant is removed by pipetting and stored at 4° C. The removed supernatant is replaced by fresh 200 µl of 1× PBS. After 48 hours the samples are measured spectrometrically at 280 nm and the amount of released compstatin is calculated as percentage of a reference sample containing a concentration of compstatin equaling 100% release.

Figure 6:
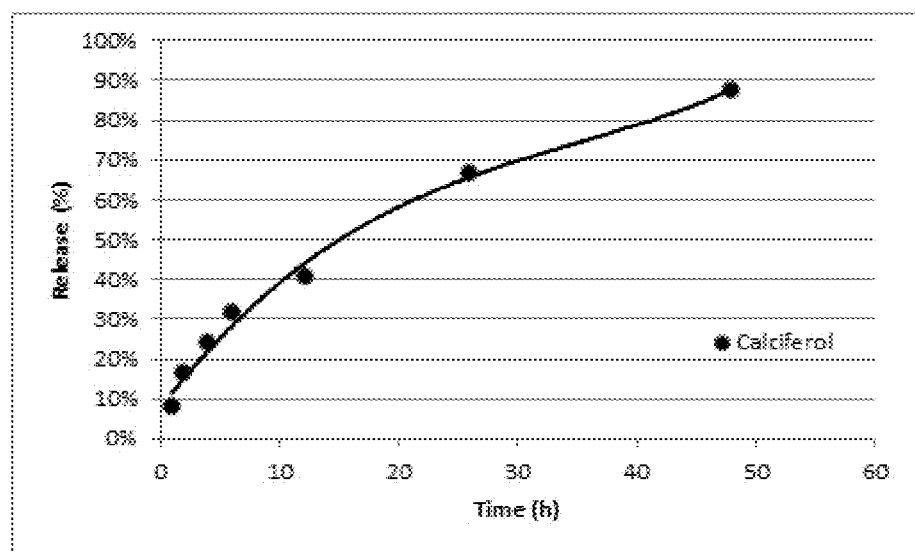

FIG. 6 shows the release of vitamin D3 from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of calcitriol (1α,25-dihydroxyvitamin D3; 1,25-(OH)$_2$D3) from PLGA-PEG-PLGA hydrogels, a stock solution of 2 mg/ml in absolute ethanol of calcitriol (Cayman/Biomol GmbH, Hamburg) is prepared. An aliquot of 20 µl of the stock solution is combined with 160 µl of 25% gel solution and 20 µl of 10× PBS. The mixture is incubated for 2 minutes at 37° C. to induce gelling and overlayed with 200 µl of 1× PBS. At frequent timepoints the supernatant is removed by pipetting and stored at 4° C. The removed supernatant is replaced by fresh 200 µl of 1× PBS. Controls of the same concentration of calcitriol in 1× PBS without gel are incubated and sampled in parallel. After 48 hours the samples and controls are analysed using a Vitamin D ELISA kit, according to the manual of the manufacturer (Euroimmun 28 AG, Luebeck). In brief, 20 µl of diluted samples are mixed with 230 µl of sample buffer containing a biotin-labeled 25-OH vitamin D derivative. 200 µl of the mixture are transferred to an ELISA well of a 8-well strip and incubated at room temperature for 2 hours. The wells are washed with 3×300 µl washing buffer. Peroxidase labelled streptavidin-conjugate (100 µl) is added and incubated for a further hour. The well is again washed 3× with 300 ml washing buffer. Tetramethyl-benzidine (100 µl) substrate solution is added and developed until sufficient coloring. The reaction is stopped by addition of 100 µl 0.5 M sulphuric acid and measured spectrometrically at 420 nm with reference 650 nm.

Figure 7:
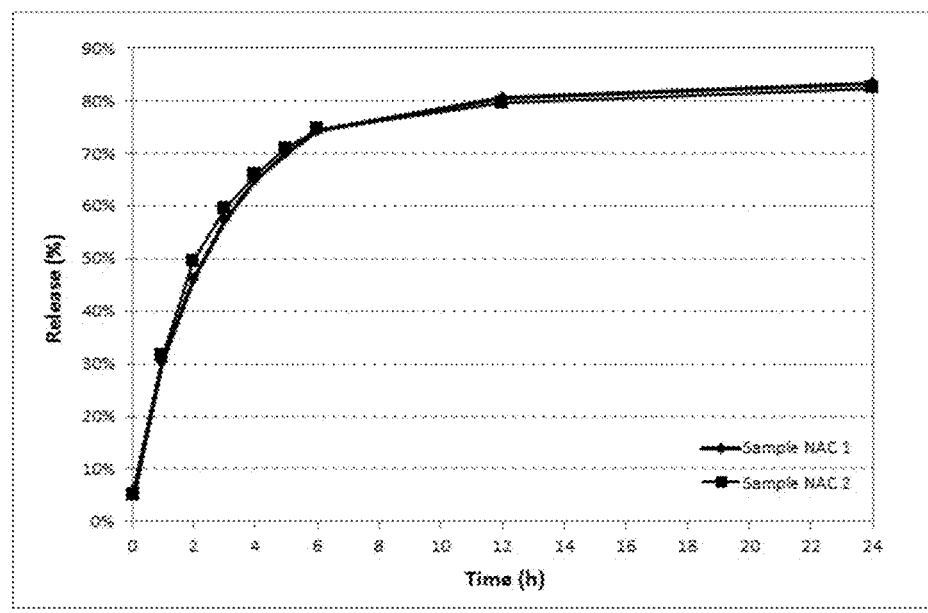

FIG. 7 shows the release of TNFR1 inhibitor N-acetyl-L-cysteine (NAC) from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of NAC from PLGA-PEG-PLGA hydrogels, varying volumes (10 µl, 20 µl, 40 µl, 80 µl) of NAC (50 mg/ml PBS (0.3 M) at pH 7.4,) are added to 200 µl gel solution (25% concentration in PBS pH 7.4) and incubated at 37° C. for gelation. Gels are covered with 1.8 ml PBS and incubated at 37° C. At indicated times samples of the supernatant of the gels are taken and analysed for NAC using the reaction of 4,4'-dithiopyridine (4-PDS) with thiols, which gives the corresponding 4-thiopyridone (4-TP).

Figure 8:
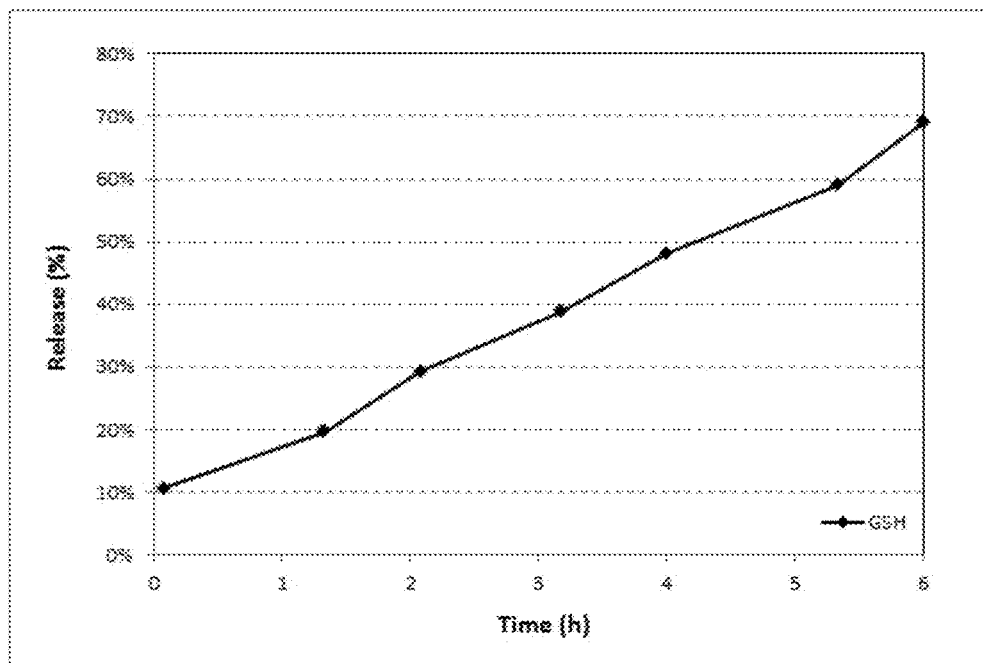

FIG. 8 shows the release of TNFR1 inhibitor glutathione (GSH) from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of GSH from PLGA-PEG-PLGA hydrogels, varying volumes (10 µl, 20 µl, 40 µl, 80 µl) of 10 mM GSH in PBS, pH 7.4, were added to 200 µl gel solution (25% concentration in PBS pH 7.4) and incubated at 37° C. for gelation. Gels are covered with 1.8 ml PBS and incubated at 37° C. At indicated times samples of the supernatant of the gels are taken and analysed for GSH using the reaction of 4,4'-dithiopyridine (4-PDS) with thiols, which gives the corresponding 4-thiopyridone (4-TP).

Figure 9:
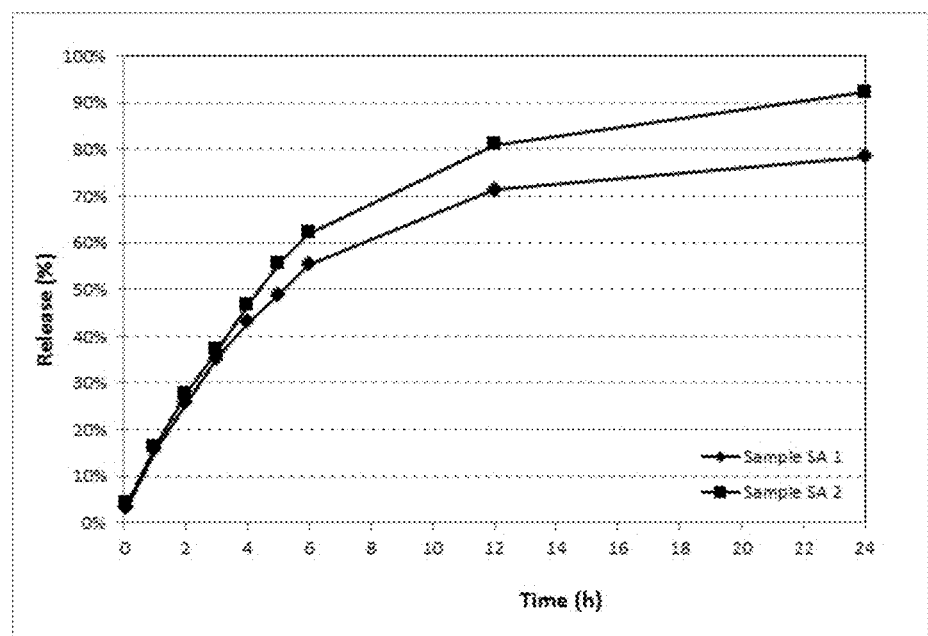

FIG. 9 shows the release of TNFR1 inhibitor sodium salicylate (SA) from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of SA from PLGA-PEG-PLGA hydrogels, varying volumes (10 µl, 20 µl, 40 µl, 80 µl) of 10 mM SA in PBS, pH 7.4, are added to 200 µl gel solution (25% concentration in PBS pH 7.4) and incubated at 37° C. for gelation. Gels are covered with 1.8 ml PBS and incubated at 37° C. At indicated times samples of the supernatant of the gels are taken and analysed for SA by derivatization with Fe(III) and quantification of the violet coloured tetraaquosalicylatroiron (III) complex at 530 nm.

Figure 10:
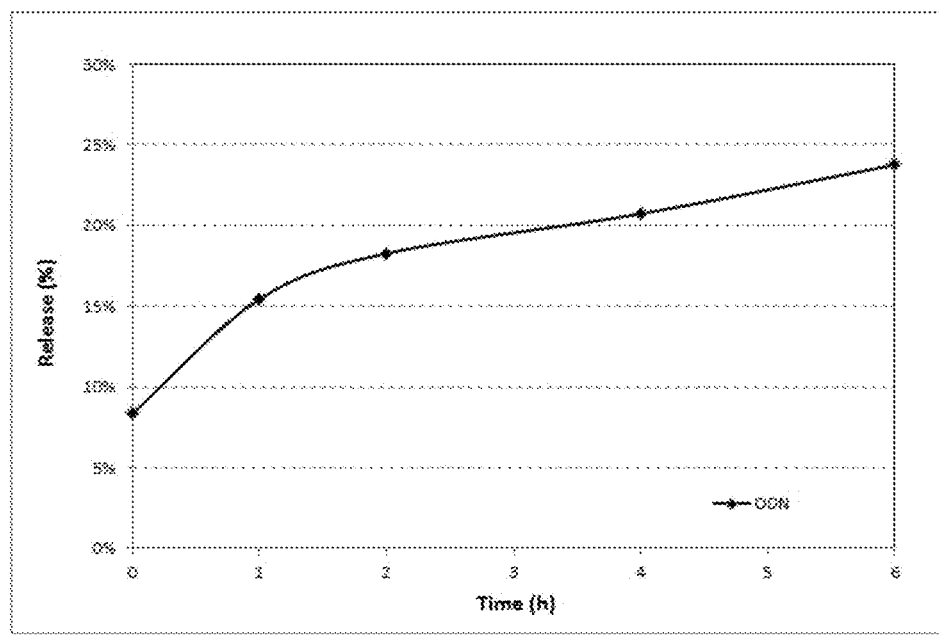

FIG. 10 shows the release of oligodeoxynucleotides (ODNs) complexed with cationic liposomes from PLGA-PEG-PLGA hydrogels.

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

For determination of the in vitro release of ODNs complexed with cationic liposomes (Cellfectin) from PLGA-PEG-PLGA hydrogels, varying volumes (10 µl, 20 µl, 40 µl, 80 µl) of ODN/Cellfection complexes prepared with a 22-mer ODN according to Example 5.4., are added to 200 µl gel solution (25% concentration in PBS pH 7.4) and incubated at 37° C. for gelation. Gels are covered with 1.8 ml PBS and incubated at 37° C. At indicated times samples of the supernatant of the gels are taken and analysed for released ODNs by absorption at 260 nm.

FIG. 11 shows the DNA sequence coding for human TNF-alpha receptor 1 (SEQ ID NO.: 1).

Shown is the DNA sequence (SEQ ID NO.: 1) coding for human TNF-alpha receptor 1 (TNFR1; Database no.: NM-001065.3; mRNA with 5'- and 3'-untranslated regions; 2258 base pairs; CDS: 304-1671, Signal peptide: 304-366, Mature peptide: 367-1668). The underlined sequence marks position of TNFR1-specific 22mer antisense pPT ODN (Ojwang and Rando 1999).

FIGS. 12A and 12B show the DNA and amino acid sequence of murine interleukin-4.

FIG. 12A shows the DNA sequence (without signal peptide sequence; 363 base pairs; Stop codon marked in bold) and protein sequence SEQ ID NO.: 3 (without signal peptide; 120 amino acids; Asterix is marking stop codon position) of the native form.

FIG. 12B shows the DNA sequence (codon optimized for E. coli expression; 429 base pairs; N-terminal 6×His- and protease cleavage-Tag; Stop codon marked in bold) and protein sequence SEQ ID NO.: 5 (141 amino acids, approx. 15.8 kDa; N-terminal tag underlined; Asterix is marking stop codon position) of the murine IL-4 QY mutant. The introduced mutations are Q137D and Y140D.

Figure 13:
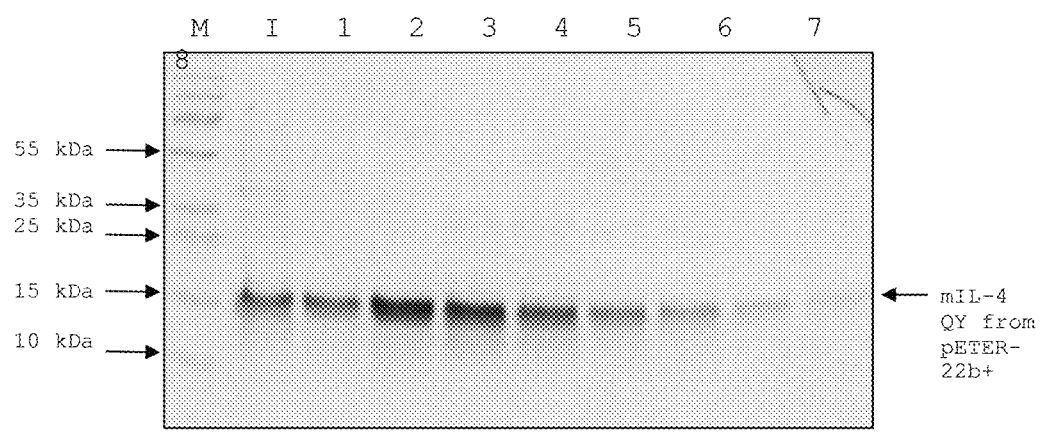

FIG. 13: Expression and purification of murine interleukin-4 (IL-4) antagonist QY Expression of recombinant His-tagged murine IL-4 antagonist QY (Q116D/Y119D) in E. coli (BL21(DE3) pLysS; Novagen) is performed as described in Example 5.7.1., followed by refolding of the insoluble IL-4 antagonist on a Ni-charged HisTrap™ FF columns (GE Healthcare) as described in Example 5.7.1. The figure shows the PAGE analysis of Ni-column purified and refolded mIL4 QY, expressed in pETER-22b+ and BL21(DE3). Coomassie stain, reducing sample buffer conditions. From left to right: M=Protein size marker (PageRuler™ Plus, Fermentas), I=purified inclusion bodies in 8 M urea, 1-8=fractions 11, 13, 15, 17, 19, 21, 23, and 25. The protein was expressed in comparably better yield than in the original TriEx construct.

DETAILED DESCRIPTION OF THE INVENTION

For the treatment of allergy, asthma and autoimmune diseases including type I diabetes, rheumatoid arthritis, and multiple sclerosis, allergen- or antigen-specific immunotherapy has the potential of restoring lasting immunological tolerance, but adjuvant strategies are needed to increase the efficacy of this approach.

The present invention provides methods for restoring lasting immunological tolerance in patients suffering from allergy, allergic asthma, various autoimmune diseases including but not limited to type 1 diabetes, rheumatoid arthritis, juvenile idiopathic arthritis, and multiple sclerosis, by treatment with allergen- or antigen-specific immunotherapy in combination with tolerance-promoting PS-containing liposomes, various combinations of 'find me' signals, various combinations of 'eat me' signals for efficient phagocytosis, various combinations of tolerance promoting liposomal surface attached ligands and individual combinations of Treg-modulating therapeutics capable of inhibiting unwanted local immune reactions at the site of antigen or allergen presentation.

I. PS-Containing Liposomes

In one embodiment, the present invention discloses phosphatidyl-L-serine (PS)-containing liposomes capable of inhibiting immune responses of antigen-specific CD4+ T cells and B cells in vivo.

Liposomes are thermodynamically stable vesicles composed of one or more concentric lipid bilayers. Liposomes have two compartments, an aqueous central core, and a lipophilic area within the lipid bilayer. Hydrophilic molecules such as hydrophilic antigens or allergens can be incorporated into the inner aqueous volume, while hydrophobic molecules can be entrapped in the lipid bilayers. A variety of liposomal carrier systems have been used for encapsulating hydrophilic and hydrophobic molecules including conventional liposomes, ethosomes, niosomes, and elastic liposomes (the initial formulation approach being termed transferosomes). Preferred for the method of the present invention are conventional PS-containing liposomes.

Conventional PS-containing liposomes are composed of PS and other phospholipids such as phosphatidylcholine (PC) from soybean or egg yolk, with or without cholesterol (CH). The most common applied PS is derived from bovine brain, but other PS sources and synthetic PS preparations such as 1-palmitoyl-2-oleyl-sn-3-glycerophosoho-L-serine or 1,2-distearoyl-sn-3-glycerophosoho-L-serine are also suitable. Cholesterol is used to stabilize the system. For the preparation of conventional PS-containing liposomes various lipid mixtures containing PS, PC and, optionally, CH are applicable including but not limited to lipid mixtures comprising molar ratios of PS:PC of 30:70 (Gilbreath et al., 1985) or 50:50 (Fadok et al., 2001) for PS-containing liposomes without cholesterol and molar ratios of PS:PC:CH of 1:1:1.33 (Harel-Adar et al., 2011) or 30:30:40 (Hoffmann et al., 2005) for PS-containing liposomes with cholesterol. As demonstrated recently, however, efficient uptake by macrophages can also be achieved with liposomes containing PS as low as 6 mol % (Geelen et al., 2012).

Conventional liposomes can be prepared in several ways. Most frequently, a film hydration method is employed, where a thin layer of lipid is deposited on the walls of a container by evaporation of a volatile solvent. An aqueous solution containing the molecule to be entrapped is added at a temperature above the transition temperature of the lipids, resulting in the formation of multilamellar vesicles. These systems contain several lipid bilayers surrounding the aqueous core. Further processing by sonication or filter extrusion generates large unilamellar vesicles (LUV, 1-5 µm diameter), or small unilamellar vesicles (LUV, 0.1-0.5 µm diameter). PS-containing liposomes with 1 µm diameter have been shown to trigger efficient uptake by macrophages (Harel-Adar et al., 2011).

PS-containing liposomes include but are not limited to PS-containing liposomes which are empty, PS-containing liposomes which contain one or more enclosed antigen or allergen, or one or more fragments thereof, or one or more allergen extracts in the presence or absence of suitable adjuvants, and PS-containing liposomes which contain one or more surface-attached antigen or allergen, or one or more surface-attached fragments thereof, or one or more surface-attached allergen extracts. In general, the surface conjugation methodology is based on three main reactions, reaction between activated carboxyl groups and amino groups yielding amide bonds, reaction between pyridyldithiols and thiols yielding disulphide bonds, and reaction between maleimide derivatives and thiols yielding thioether bonds. Other approaches also exist, such as those that yield carbamate bonds via the reaction of p-nitrophenylcarbonyl groups and amino groups (for a review, see Torchilin, 2005). All of these conjugation reactions can be used to directly attach ligands to the liposomal surface (e.g., via phosphatidylethanolamine) or to attach ligands to liposomes via spacer molecules such as polyethylene glycol (PEG) spacer molecules (e.g., via PEGylated phosphatidylethanolamine).

II. 'Find Me' Signals

Apoptotic cells are quickly recognized and removed by phagocytes, which can be either neighboring healthy cells or professional phagocytes recruited to the site of apoptotic cell death. Phagocytes are extremely efficient in sensing and detecting the dying cells at the earliest stages of apoptosis and in the recent past, several find-me signals released from apoptotic cells have been identified (for a review, see Ravichandran, 2011).

In one embodiment, the present invention utilizes 'find me' signals capable of triggering effective local phagocytosis. Suitable 'find me' signals include but are not limited to fractalkine (chemokine CXC3CL1), lysophosphatidylcholine (LPC), sphingosine-1-phosphate (SiP) and the nucleotides ATP and UTP. Preferred are 'find me' signals which can be embedded in substantial quantities in matrices selected for controlled delivery of PS-containing liposomes, which are chemically and physically compatible with such matrices, and which are released from such matrices over a prolonged period of time.

In a preferred embodiment, equimolar quantities of ATP and UTP are employed as 'find me' signals. Using a transwell migration assay, both nucleotides have been demonstrated to effect maximal migration (approximately a three-fold increase) of phagocytes at a concentration of about 100 nM (Elliott et al., 2009). For the method of the present invention it is important to restrict the concentration of ATP and UTP to the lower nanomolar range since extracellular nucleotides at higher concentrations (more than 1 µM, for example, by necrotic cells) are considered pro-inflammatory (Kono and Rock, 2008).

II. Eat Me' Signals

Several studies have suggested that PS recognition is both necessary and sufficient for clearance of apoptotic cells. However, there is also evidence that apoptotic cells expose additional 'eat me' signals, the combination of which may enhance engulfment. Numerous 'eat me' signals exposed on apoptotic cells have been identified to date including but not limited to changes in glycosylation of surface proteins or changes in surface charge, expression of intercellular adhesion molecule 3 (ICAM3) and oxidized low-density lipoprotein particle (OxLDL), and exposure of certain intracellular proteins such as calreticulin and annexin I (for a review, see Hochreiter-Hufford and Ravichandran, 2013).

In one embodiment, one or more of these additional 'eat me' signals exposed on apoptotic cells, are attached to the surface of PS-containing liposomes or added to mixtures comprising PS-containing liposomes in order to enhance tolerance-promoting phagocytosis.

In a preferred specific embodiment, annexin I (annexin A1, ANXA1) is employed as additional 'eat me' signal attached to PS-containing liposomes. ANXA1 is a 38 kDa protein that is recruited from the cytosol and exported to the outer plasma membrane leaflet, where it is required for efficient clearance of apoptotic cells. It binds to PS in a calcium-dependent manner, thereby mediating tethering of apoptotic cells to engulfing cells and internalization. ANXA1 is thought to bind to PS in a bivalent manner. Thereby, ANXA1 can act as a bridging protein between two PS molecules and is capable of pulling two membranes together. However, ANXA1 can also bind to other proteins such as S100 to produce complexes that can cross-link two membranes. Silencing of ANXA1 gene expression via siRNA has been shown to result in defective engulfment of apoptotic cells and the addition of purified soluble annexin I restored the observed engulfment defects observed in these cells (Arur et al., 2003). For the method of the present invention it is also advantageous that that ANXA1 mediates various other anti-inflammatory functions in addition to its tethering function. For example, ANXA1 mediates also the anti-inflammatory action of glucocorticoids and its N-terminal peptide can bind to the formyl peptide receptor on neutrophils, thereby preventing their trans-endothelial extravasation. Furthermore, exogenous administration of annexin I has been demonstrated to confer anti-inflammatory activity in animals (Goulding et al., 1998).

In another preferred specific embodiment, calreticulin is employed as additional 'eat me' signal in cooperation with PS-containing liposomes. The endoplasmatic protein calreticulin (CRT) is a highly conserved 46 kDa protein. By still unknown mechanisms, CRT can be transported to the plasma membrane and is detectable on the cell surface. As a cell surface protein CRT has been implicated in antigen presentation and complement activation, immunogenicity of cancer cell death, wound healing, thrombospondin signaling, and clearance of apoptotic cells. Via trans-activation of the Low density lipoprotein Receptor-related Protein 1 (LRP1, also known as CD91 or the α2-macroglobulin receptor) on phagocytes, CRT can act as a receptor for collectin family members (e.g., mannose binding lectin (MBL) and surfactant proteins A and D) and mediate uptake of apoptotic cells (Gardai et al., 2005). Most important for the method of the present invention is the fact that CRT does not need to be bound by a ligand to engage and stimulate LRP (Gardai et al., 2005). Thus, CRT and PS-containing liposomes can be administered as individual components and still act together to drive optimal phagocytosis. Also important for the method of the present invention is the observation that PS appears to drive the anti-inflammatory consequences of apoptotic cell-recognition, although LRP1 stimulation by CRT is known to be pro-inflammatory (Gardai et al., 2005). Thus, the combination of CRT and PS-containing liposomes can be assumed to drive optimal tolerance-promoting phagocytosis.

In another embodiment, one or more serum adaptor proteins capable of bridging PS to receptors on phagocytes, are employed in addition to 'eat me' signals on apoptotic cells in order to enhance phagocytosis. Suitable serum adaptor proteins include but are not limited to β2-glycoprotein I (β2GPI), the growth arrest-specific gene product 6 (Gas6), the milk-fat globule EGF-factor 8 (MFG-E8), and protein S.

In a preferred specific embodiment, the milk-fat globule EGF-factor 8 (MFG-E8) is employed as additional 'eat me' signal in cooperation with PS-containing liposomes. MFG-E8 contains one or two EGF-like domains, two F5/8 type C domains, a PS-binding domain and an arginine-glycine-aspartic acid (RGD) motif, which enables the binding to integrins. Thereby, MFG-E8 bridges apoptotic cells or PS-containing liposomes to integrins on the surface of phagocytes (Hanayama et al., 2002). For the method of the present invention, recombinant human MFG-E8 can be produced in different eukaryotic systems. One MFG-E8 construct comprising 463 amino acid residues (apparent molecular weight 72 kDa) has been expressed in human 293T cells (Hanayama et al., 2002) and another MFG-E8 construct comprising 374 amino acid residues (apparent molecular weight 45 kDa) has been expressed in a baculovirus/insect cell system (e.g., Sino Biological Inc., Bejing, P-R. China).

In another preferred specific embodiment, β2-glycoprotein I (β2GPI) is employed as additional 'eat me' signal in cooperation with PS-containing liposomes. $β_2$-Glycoprotein I (also known as apolipoprotein H) is an anionic phospholipid-binding glycoprotein that belongs to the complement control protein (CCP) superfamily. $β_2$-GPI consists of 326 amino acids and contains four N-glycosylation sites (Arg143, Arg164, Arg174, and Arg234) and one O-linked sugar on Thr130. The glycans account for approximately 20% w/w of the total molecular mass (50 kDa). $β_2$-GPI is organized in five CCP domains. The first four domains have the regular, conserved sequences, but the fifth domain is aberrant. This domain contains a six-residue insertion, a 19-residue C-terminal extension, and an additional disulfide bond that includes a C-terminal cysteine. These additional amino acids in domain V constitute a large positively charged patch that mediates binding to anionic phospholipids. Thereby, $β_2$-GPI serves as an intermediate for the interaction of PS-exposing apoptotic cells or PS-containing liposomes with macrophages (Balasubramanian and Schroit, 1998). $β_2$-GPI is a relatively abundant plasma protein and it circulates in blood at a level of 50-500 µg ml$^{-1}$ (1-10 µm). For the method of the present invention, PS-containing liposomes are preincubated with $β_2$-GPI prior to administration at the site of antigen or allergen presentation. Recombinant human $β_2$-GPI can be produced in different eukaryotic systems. For example, a full-length cDNA coding a human $β_2$-GPI (mol. wt 43000) has been produced in a baculovirus/insect cell system and purified from the culture supernatant by sequential cardiolipin-affinity column chromatography and gel filtration (Igarashi et al., 1993).

In another embodiment, one or more serum adaptor proteins involved in the recognition of apoptotic cells, are employed in addition to 'eat me' signals on apoptotic cells in order to enhance phagocytosis. Suitable serum adaptor proteins include but are not limited to thrombospondin, complement protein C1q, c-reactive protein (CRP), Immunoglobulin M (IgM), and mannose binding lectin (MBL) (for a review, see Chaurio et al., 2009).

IV. Tolerance-Supporting Liposomal Surface Ligands

In one embodiment, PS-containing liposomes are modified by one or more surface-attached ligands capable of supporting the tolerance-promoting effect of PS. Such ligands include but are not limited to ligands of B cell inhibitory coreceptors and mannose receptors.

B cell inhibitory coreceptors include but are not limited to CD22 and SIGLEC-10 (SIGLEC-G in mice), both members of the sialic acid binding Ig-like lectin immunoglobulin family which contain at least one ITIM on their cytoplasmic tail and are capable of inhibiting B cell receptor-mediated signaling. Ligands of these coreceptors are sialic acid-containing glycans of glycoproteins and glycolipids. CD22 exhibits a strict preference for α2-6-sialosides over α2-3-sialosides, whereas SIGLEC-G has the ability to bind α2-3-sialosides. Liposomes displaying both antigen and CD22 glycan lipids have been shown to induce robust antigen-specific tolerance to protein antigens in mice (Macauley et al., 2013). Liposomes displaying both antigen and SIGLEC-G glycan lipids have also been shown to inhibit B cell receptor signaling and to induce robust tolerance toward T-independent and T-dependent antigens in mice (Pfrengle et al., 2013).

Preferred ethylamine-derivatized human CD22 glycan ligands include but are not limited to [9-biphenylcarboxyl-N-glycolylneuraminic acid-α2-6-galactose-β1-4-N-acetylglucosamine-β-ethylamine (6'-$^{BPC}$NeuGc)]. Preferred murine ethylamine-derivatized CD22 glycan ligands include but are not limited to [9-biphenylacetyl-N-glycolylneuraminic acid-α2-6-galactose-β1-4-N-acetylglucosamine-β-ethylamine (6'-$^{BPA}$NeuGc)], which binds to murine CD22 with 200-fold higher affinity than its natural ethylamine-derivatized ligand NeuGcα2-6Galβ1-4GlcNAc-β-ethylamine. Preferred murine ethylamine-derivatized SIGLEC-G glycan ligands include but are not limited to [9-biphenylacetyl-N-glycolylneuraminic acid-α2-3-galactose-β1-4-N-acetylglucosamine-β-ethylamine (3'-$^{BPA}$-NeuGc)], and the natural ethylamine-derivatized ligand NeuGcα2-3Galβ1-4GlcNAc-β-ethylamine. Methods for coupling of these glycan ligands to lipid molecules are known to the person skilled in the art. In a preferred coupling procedure the ethylamine-derivatized glycan ligands are reacted with NHS-derivatized PEG-spacer which are covalently attached to phosphatidylethanolamine molecules.

In another embodiment, PS-containing liposomes are modified by one or more surface-attached mannose residues or oligomannose molecules capable of supporting the tolerance-promoting effect of PS. On one hand, oligomannose-coated liposomes have been reported to induce a strong Th1 immune response against encapsulated antigens in mice, with significant IFN-γ production and suppressed IL-4 production following uptake of such liposomes by antigen-presenting cells such as macrophages (Ishii et al., 2010). On the other hand, however, there is also evidence that oligomannose-coated liposomes with encapsulated antigens induce IL-10 production in murine spenocytes, pointing to the induction of regulatory T cells (Ishii et al., 2010). This observation is supported by a recent immunotherapy study in which intranasal immunization with oligomannose-coated liposomes containing encapsulated antigens induced a subset of regulatory CD8+ T cells as well as CD4+CD25+ Foxp3+ T cells and, thereby, ameliorated allergic symptoms in allergen-sensitized mice (Kawakita et al., 2012). In another recent study, subcutaneous (s.c.) injection of oligomannose-coated liposomes containing encapsulated immunodominant peptides of the myelin basic protein (MBP) protected Dark Agouti rats against experimental autoimmune encephalomyelitis (Belogurov et al., 2013). According to the authors several mechanisms may have a role in disease suppression, including effective harvesting of the liposomes with surface-exposed mannose residues by antigen-presenting cells which are rich in mannose receptors, with subsequent induction of immune suppression, probably via regulatory T cells. The latter assumption is supported by histological analyses for cytokines in the CNS of treated rats which revealed significant down-regulation of Th1 cytokines IL-2 and IFN-γ (Belogurov et al., 2013). Furthermore, for the method of the present invention it is important that apparently s.c. injected oligomannose-coated liposomes have the ability to act in the periphery with subsequent induction of immune suppression in the CNS. It is unlikely that s.c. injected liposomes penetrate the blood brain barrier and reach the CNS.

Methods for coupling of mannose or oligomannose to lipid molecules are known to the person skilled in the art. In a preferred coupling procedure mannotriose with the structure Manα1-6(Manα1-3)Man is covalently attached to phosphatidylethanolamine molecules as described (Mizuochi et al., 1989).

V. Mediators of Macrophage-Mediated Immune Suppression

In one embodiment, PS-containing liposomes are modified by encapsulation of one or more mediators of macrophage-induced immune suppression including but not limited to microRNA-21 (miR-21) and resolvin D1.

MicroRNAs (miRs) are 19-22 nucleotides long and function as non-coding RNAs. In general, miRs negatively regulate gene expression post-transcriptionally by binding to the 3'-untranslated region (UTR) of the targeted messenger RNA (mRNA) to inhibit gene translation. Emerging evidence indicates that miR-21 regulates inflammatory responses. For example, in macrophages miR-21 silences the pro-inflammatory IL-12. Furthermore, upon phagocytosis of apoptotic cells (named efferocytosis) the expression of inducible miR-21 in macrophages is increased, leading to silencing of PDCD4 (programmed cell death protein 4) and favoring of c-Jun-AP-1 activity (c-Jun in combination with c-Fos forms the AP-1 early response transcription factor), which in turn results in elevated production of anti-inflammatory IL-10 (Das et al., 2014).

In a preferred specific embodiment, PS-containing liposomes are modified by encapsulation of miR-21 mimic which is a double strand sense mature miR-21. As demonstrated in a recent study, an increase of the cellular abundance of miR-21 levels in human monocyte-derive macrophages by transfection with miR-21 mimic (miRIDIAN mimic-miR-21; Dharmacon RNA Technologies) inhibited PDCD4 expression and resulted in significant suppression of LPS-induced TNF-α expression and NF-κB activation (Das et al., 2014).

In another embodiment, PS-containing liposomes are modified by encapsulation of resolvin D1, an inducer of miR-21 (Das et al., 2014). Resolvins are compounds that are made by the human body from the omega-3 fatty acids eicosapentaenoic acid (EPA) docosahexanenoic acid (DHA). They are produced by the COX-2 pathway especially in the presence of acetyl salicylic acid. Experimental evidence indicates that resolvins reduce cellular inflammation. Resolvin D1 is produced physiologically from the sequential oxygenation of DHA by 15- and 5-lipoxygenase.

In a preferred specific embodiment, PS-containing liposomes are modified by encapsulation (ethanolic solution) or incorporation into the liposomal layers of commercially available 7(R)-Resolvin D1, an aspirin-triggered epimer of resolvin D1 that reduces human polymorphonuclear leukocyte (PMN) transendothelial migration, the earliest event in acute inflammation, with equipotency to resolvin D1

($EC_{50}$=~30 nM). 17(R)-Resolvin D1 exhibits a dose-dependent reduction in leukocyte infiltration in a mouse model of peritonitis with maximal inhibition of ~35% at a 100 ng dose. In contrast to resolvin D1, the aspirin-triggered form resists rapid inactivation by eicosanoid oxidoreductases (Sun et al., 2007).

VI. Immune Modulators of Treg Functions

Subcutaneous injection of PS-containing liposomes at the site of allergen or antigen presentation could also trigger, in addition to the tolerance-promoting uptake by macrophages, uptake and activation of resident leukocyte populations such as Langerhans cells, dermal dendritic cells, and/or γδ-T cells, resulting in the production of proinflammatory cytokines. Since a proinflammatory response could negate the upregulation of negative costimulatory molecules such as CTLA-4 and PD-L1, both of which play an important role in phagocyte-induced tolerance (Eagar et al., 2002; Fife et al., 2006), the present invention provides methods for local inhibition of a proinflammatory response via Treg-mediated suppression of effector T cells at the site of allergen or antigen presentation.

The activation, proliferation and effector functions of a large spectrum of immune-competent cells such as CD4+ cells, CD8+ cells are susceptible to suppression mediated by regulatory T cells (Tregs). The induction of Treg-suppressive activity is specific and requires antigenic or allergenic stimulation through the T cell receptor (TCR). The suppressive activity of Tregs, however, is not antigen/allergen-specific. Therefore, a wide range of immune responses can be inhibited by Tregs via 'bystander' suppression. The exact mechanisms of Treg-mediated suppression remain to be elucidated, but cell-to-cell contacts and several molecules such as IL-10, TGF-beta, CTLA-4 (cytotoxic T lymphocyte antigen 4; CD152) and granzyme/perforin are reported to contribute to the suppressive activity of Tregs (for a review, see Chen and Oppenheim, 2010).

In one embodiment, the present invention discloses low molecular weight immune modulators capable of addressing the complex network of Treg induction at different target sites including low molecular weight immune modulators targeting complement-mediated pathways, TNF-alpha-mediated pathways, vitamin D3-mediated pathways, and IL-4/IL-13-mediated pathways as described in detail in patent application EP 13075040.9.

In another embodiment, the present invention discloses methods for restricting high local concentrations of low molecular weight immune modulators capable of stimulating the induction of Tregs mainly to the site of allergen presentation to reduce adverse effects due to interaction of the immune modulators with targets distal from the site of allergen or antigen presentation. Preferred are low molecular weight immune modulators which provide a relatively short serum half-life that is sufficient to be locally active upon their release from a depot at the site of allergen presentation, and which allows fast removal from circulation upon diffusion and transport away from the site of allergen presentation. Preferred therapeutics providing such characteristics include but are not limited to a) oligopeptide-based complement inhibitors, b) oligonucleotide-based therapeutics for the inhibition of TNF-alpha-, IL-4/IL-13- and complement-mediated pathways, c) glutathione-, salicylate- and oligonucleotide-based therapeutics for the inhibition of TNFR1-mediated pathways, d) selected vitamin D3 analogs such as calcipotriol, and e) medium molecular weight proteins such as IL-4 muteins and TNF-alpha mutants.

In one specific embodiment, the present invention discloses low molecular weight complement inhibitors capable of modulating the induction of Tregs. In a preferred specific embodiment, the present invention discloses low molecular weight complement inhibitors targeting complement protein C3 and interactions of the anaphylatoxins C3a and C5a with their respective receptors. In a preferred specific embodiment, the 13-residue cyclic peptide (H-I[CVVQDWGHHRC]T-$NH_2$) is used for the method of the present invention. This cyclic peptide is able to bind selectively to primate C3 and its C3b and C3c fragments, and to inhibit cleavage of C3 by C3 convertases of both the classical and the alternative pathway (Sahu et al., 1996; Ricklin and Lambris, 2008).

In another specific embodiment, the present invention discloses low to moderate molecular weight inhibitors of TNFR1 or TNFR1-mediated functions capable of modulating the induction of Tregs. Suitable low to moderate molecular weight inhibitors of TNFR1 or TNFR1-mediated include but are not limited a) to molecules capable of specific inhibition of sTNF so that the mTNF-TNFR1 and mTNF-TNFR2 interactions remain intact such as dominant-negative sTNF mutants, b) molecules capable of specific inhibition of TNFR1 while leaving TNFR2 signaling intact such as antagonistic TNF mutants with specificity for TNFR1, antisense oligonucleotides with specificity for TNFR1, aptamers with specificity for TNFR1, and oligonucleotides capable of TNFR1 silencing via RNAi, and c) molecules capable of inhibiting TNFR1-mediated pathways including such as S-methylglutathione, pro-glutathione drugs (e.g., N-acetylcysteine), and salicylates. In one preferred specific embodiment, sodium salicylate (SA), salicylamide or choline magnesium trisalicylate are used as inhibitors of TNFR1-mediated effects. SA has been shown to reduce IL-4 secretion and RNA expression in human CD4+ T cells (Cianferoni et al., 2001). As important is the observation that salicylate-mediated inhibition of IL-4 expression does not affect IL-2 expression (Cianferoni et al., 2001), which is an essential cytokine for up-regulating TNFR2 expression on Tregs (Chen and Oppenheim, 2010). In another preferred specific embodiment, antisense oligonucleotides with specificity for TNFR1, are used as inhibitors of TNFR1-mediated effects. TNFR1-specific antisense oligonucleotides have been applied to prevent apoptotic signaling through TNFR1 after ionizing radiation treatment (Huang et al., 2006). Pretreatment of mice with 2'-O-(2-methoxy)ethyl-modified antisense oligonucleotides (25 mg/kg i.p. every other day for a total of four times) protected the mice successfully against radiation-induced liver damage. In order to overcome the limited cellular uptake of such oligonucleotides, they are complexed with cationic lipids and then formulated into cationic liposomes.

In another specific embodiment, the present invention discloses low molecular weight molecules capable of modulating the induction of Tregs via vitamin D-mediated pathways including but not limited to a) active vitamin D3 (calcitriol; 1,25-$(OH)_2$D3), b) its inactive form (cholecalciferol; 25(OH)D3), c) vitamin D3 analogues such as 19-nor-vitamin D analogues, 24-hydroxy vitamin D derivatives, and 1α-hydroxyvitamin D3, and d) non-secosteroidal vitamin D receptor (VDR) modulators.

In a preferred specific embodiment, calcipotriol is used for the method of the present invention. As compared to 1,25-$(OH)_2$D3, calcipotriol has 100-200 times less effect on calcium metabolism including activation of calcium absorption and bone calcium mobilization (Kissmeyer and Binderup, 1991). An important advantage for the method of the present invention is the short half-life of calcipotriol in circulation which is measured in minutes (Kragballe, 1995).

After i.v. injection of 10 µg/kg calcipotriol in rats, calcipotriol was detectable in serum by HPLC analysis only up to 5 min, and after i.v. injection of 50 µg/kg up to 10 min (Kissmeyer and Binderup, 1991). The rate of clearance (half-life of 4 min) was approximately 140 times higher for calcipotriol than for 1,25-$(OH)_2$D3. Furthermore, calcipotriol is rapidly metabolized and effects of the metabolites have been demonstrated to be 100 times weaker than those of the parent compound (Kissmeyer and Binderup, 1991). Due to these characteristics, calcipotriol has been used clinically for more than 10 years for topical treatment of psoriasis without systemic toxicity (for a review, see Plum and DeLuca, 2010).

In still another specific embodiment, the present invention discloses low to moderate molecular weight molecules capable of modulating the induction of Tregs via inhibition of IL-4/IL-13-mediated pathways including but not limited to a) antagonistic IL-4 and IL-13 derivatives, b) aptamers with specificity for IL-4 and IL-13 capable of blocking their biologic activity, c) aptamers with specificity for IL-4 and IL-13 receptor complexes capable of blocking the interaction of IL-4 and IL-13 with their receptor subunits, and d) monoclonal antibodies fragments or other medium molecular weight proteinaceous constructs with specificity for IL-4 and IL-13 receptor complexes capable of blocking the interaction of IL-4 and IL-13 with their receptor subunits. In a preferred specific embodiment, antagonistic interleukin-4 variants are used comprising single, double and triple mutations, single mutations including but not limited to amino acid positions R121, Y124, and S125, double and triple mutations including but not limited to combinations of the above listed amino acid positions.

VII. Adjuvants

The time of allergen or antigen exposure is extremely important since T cell differentiation and thus the development of immunologic memory requires the engagement of the T cell receptor (TCR) over 12-48 h and long lasting memory may even require repetitive exposure. Adjuvants such as oils and alum provide a depot effect that extends the lifetime of allergens and antigens and thus prolong antigen-stimulation of T cells. However, in addition to the depot effect currently available adjuvants trigger either Th1-type or Th2-type immune responses or both (for reviews, see Leroux-Roels, 2010; Nicholls et al., 2010; Brunner et al., 2010). Based on the assumption that the generation of Tregs represents a default pathway which requires T-cell receptor activation but the absence of decision signals for effector T cells, currently available adjuvants are not optimal for the purpose of the present invention. For the method of the present invention adjuvants are needed that promote antigen or allergen uptake and prolonged stimulation of T cells without providing decision signals, thereby inducing Treg expansion. Unfortunately, adjuvants providing all of the desired properties are not available.

In one embodiment of the present invention, adjuvants eliciting a Th2-type immune response, including but not limited to aluminum salts, Montanide emulsions (squalene-based water-in-oil emulsions) and polyphosphazenes, are employed in combination with locally administered Treg-modulating therapeutics capable of inhibiting IL-4/IL-13-mediated pathways. In the presence of inhibitors of IL-4- and IL-13-mediated pathways the contra-productive activity of adjuvants eliciting Th2-type immune responses is significantly reduced or even abolished.

In another embodiment of the present invention, adjuvants eliciting a Th1-type immune response, including but not limited to monophosphoryl lipid A (MPL) and CpG oligonucleotides, are employed in combination with locally administered vitamin D3 or analogs thereof. A recent study in mice has demonstrated that topical pretreatment with the vitamin D3 analog calcipotriol for 1 day followed by transcutaneous immunization within the treated skin area with ovalbumin in the presence of a CpG oligonucleotide adjuvant (TLR9 agonist) abolished antigen-specific CD8+ T cell priming and induced CD4+CD25+ Tregs, thereby promoting antigen-specific tolerance (Ghoreishi et al., 2009). Based on this study, the contra-productive activity of adjuvants eliciting Th1-type immune responses can be assumed to be significantly reduced or even abolished in the presence of vitamin D3 or analogs thereof.

In still another embodiment of the present invention, adjuvants eliciting a combined Th1-type and Th2-type immune response, including but not limited to squalene-based oil-in-water emulsions (MF59), saponins (e.g., Quil-A or a purified fraction of Quil-A (QS21)), granulocyte-macrophage colony stimulating factor (GM-CSF), and adjuvants based on inulin and virosomes are employed in combination with locally administered vitamin D3 or analogs thereof and Treg-modulating therapeutics capable of inhibiting IL-4/IL-13-mediated pathways.

In a preferred embodiment, PS-containing liposomes presenting encapsulated or surface-attached antigens or allergens are employed as adjuvants in combination with one or more Treg-modulating therapeutics for local inhibition of a proinflammatory response via Treg-mediated suppression of effector T cells at the site of allergen or antigen presentation. While regular liposomes are not active per se. PS-containing liposomes represent a tolerance-promoting adjuvant via macrophage-mediated uptake, optionally enforced by locally administered 'find me' and 'eat me' signals. The sustained release of PS-containing liposomes presenting encapsulated or surface-attached antigens or allergens from a locally administered hydrogel guarantees a continuous uptake of such liposomes by macrophages and, thereby, a prolonged engagement of the T cell receptor (TCR) which appears to be essential for the induction of tolerance.

VIII. Matrices for Sustained Delivery

Effective supportive promotion of tolerance by PS-containing liposomes at the site of allergen or antigen presentation requires a sustained local delivery of PS-containing liposomes and, optionally, in combination with one or more 'find me' signals for efficient peripheral phagocytosis, one or more 'eat me' signals for enhanced phagocytosis, and individual combinations of Treg-modulating therapeutics capable of inhibiting unwanted local immune reactions at the site of antigen or allergen presentation, from a depot-mediating matrix for a period of time that is sufficient for the purpose of the particular medical treatment, at least for the period of allergen or antigen presentation.

In one embodiment, the present invention discloses suitable matrices for sustained local delivery of PS-containing liposomes capable of inhibiting immune responses of antigen-specific CD4+ T cells and B cells in vivo at the site of antigen or allergen presentation along with a prolonged presentation of allergens or antigens or fragments thereof. Preferred matrices a) can serve as depot for sufficient quantities of PS-containing liposomes, and, optionally, one or more 'find me' signals, one or more 'eat me' signals, and individual combinations of Treg-modulating therapeutics, b) allow the release of sufficient quantities of the embedded components over a prolonged period of time (optimally for a few days), and c) are chemically and physically compatible with all embedded components.

VIII.1. Biodegradable Polymers

In one specific embodiment of the invention, biodegradable polymers are used for sustained delivery of PS-containing liposomes and, optionally, one or more 'find me' signals, one or more 'eat me' signals, and individual combinations of Treg-modulating therapeutics. Preferred biodegradable polymers approved by FDA and used in a clinical trial, include but are not limited to poly(D,L-lactic acid), poly(lactic-co-glycolic acid) (PLGA), and copolymers of L-lactide and D,L-lactide. An important characteristic of such polymers is their ability to be applied locally. All FDA approved polymers have been studied extensively for their biocompatibility, toxicology, and degradation kinetics. Furthermore, these polymers have been shown to release embedded therapeutics for several hours up to 40 weeks in vitro and several weeks in vivo.

VIII.2. Biodegradable Thermogelling Hydrogels

In a preferred specific embodiment, injectable in situ-forming gel systems which are biodegradable, are used for sustained delivery of PS-containing liposomes and, optionally, one or more 'find me' signals, one or more 'eat me' signals, and individual combinations of Treg-modulating therapeutics (for a review, see Ruel-Gariepy and Leroux, 2004). Preferred in situ-forming gel systems (hydrogels) undergo a sol-gel-sol transition, which is a free flowing sol at room temperature and a non-flowing gel at body temperature. Compared to other biodegradable polymers, the injectable thermo-gelling polymers possess several advantages including easy preparation, high encapsulation efficiency of bioactive molecules including therapeutic proteins, and free of harmful organic solvents in the formulation process (Qiao et al. 2005).

Useful for the method of the present invention are biodegradable thermogelling block polymers which are based on monomethoxy poly(ethylene glycol) (MPEG) including but not limited to a) diblock copolymers consisting of MPEG and poly(ε-caprolactone) (PCL) (Hyun et al., 2007), b) MPEG-b-(PCL-ran-PLLA) diblock copolymers (Kang et al., 2010), and c) diblock copolymers consisting of MPEG and PLGA (Peng et al., 2010). MPEG copolymers containing PCL provide the advantage that they do not create an acidic environment upon biodegradation in contrast to MPEG copolymers containing PLLA and PLGA (Hyun et al., 2007).

Useful for the method of the present invention are also biodegradable thermogelling triblock polymers including but not limited to a) PLGA-PEG-PLGA (Qiao et al., 2005), b) PEG-PLGA-PEG (Zhang et al., 2006), and c) PEG-PCL-PEG (PECE) (Gong et al., 2009a). Various biodegradable thermogelling triblock polymers made up of PLGA and PEG are disclosed in patent application WO 99/18142. At lower temperatures, hydrogen bonding between hydrophilic PEG segments of the copolymer chains and water molecules dominate in aqueous solutions, resulting in the dissolution of these copolymers in water. As the temperature increases, the hydrogen bonding becomes weaker, while hydrophobic forces of the hydrophobic segments such as PLGA segments are getting stronger, leading to sol-gel transition. PEG, PLGA and PCL are well-known FDA-approved biodegradable and biocompatible materials which have been widely used in the biomedical field.

Useful for the method of the present invention are also biodegradable thermo-gelling diblock and triblock copolymers which consist of polyethylene oxide (PEO) and a biodegradable polyester such as poly-L-lactic acid (PLLA) (Jeong et al., 1997). These block copolymers, however, are a free flowing sol at a higher temperature and form a gel at a lower temperature. For example, a 23% aqueous solution of PEO-PLLA-PEO ($M_r$ 5,000-2,040-5,000) is a sol at 45° C. and becomes a gel at 37° C. By changing the biodegradable block length, the sol-gel transition temperature can be manipulated, e.g., increasing the PLLA block length increases the aggregation tendency of a block copolymer in water, resulting in a steepening of the gel-sol transition curve slopes and the onset of gelation at lower concentrations. The sol-gel transition temperature is a function of concentration as well as composition of a block polymer.

VIII.3. Non-Biodegradable Thermogelling Hydrogels

In another specific embodiment, poloxamers (trade name Pluronics) are used. Poloxamers are nonionic triblock copolymers composed of a central hydrophobic chain of poly (propylene oxide) (PPO) flanked by two hydrophilic chains of poly (ethylene oxide) (PEO) (Gilbert et al., 1987). Poloxamers exhibit a sol-gel transition behavior in aqueous solutions and have been used for sustained delivery of several therapeutic agents. However, poloxamers are not biodegradable and can be accumulated in the body which may lead to toxic side effects. Thus, the application of poloxamers in biomedical fields has been greatly restricted. In a recent study, Pluronic F127 (100-unit PEO chain surrounding one 65-unit PPO) has been used to form composite thermosensitive hydrogels with PECE (Gong et al., 2009b). Based on the results of this study Pluronic F127/PECE composite hydrogels are biocompatible with low cell cytotoxicity and, therefore, may also be suitable for the method of the present invention.

VIII.4. Trimethylated Chitosan-Based Hydrogels

In another specific embodiment, thermo-sensitive hydrogels formulated on the basis of trimethylated chitosan derivatives (Wu et al., 2012) are used for the sustained delivery of suitable active substances and one or more antigens or allergens. In addition to its application as a vaccine delivery system, the cationic polysaccharide has shown promising results as an adjuvant. For example, application of a chitosan solution for subcutaneous vaccination has been demonstrated to enhance both humoral and cell-mediated immune responses (Zaharoff et al., 2007). However, the unfavorable pH-dependent solubility and charge density of chitosan is a limiting factor. In contrast, trimethylated chitosan is well soluble in aqueous solution at neutral pH and provides excellent biocompatibility and mucoadhesive nature. Trimethylated chitosan derivatives are best characterized by the degree of quarternization, the degree of O-methylation and the degree of acetylation (Hagenaars et al., 2010).

Trimethylated chitosan derivatives are especially suited for nasal delivery of vaccines and are frequently formulated into particles or spray powder (Alhalaweh et al., 2009). Very recently, however, the trimethylated chitosan derivative N[(2-hydroxy-3-trimethylammonium) propyl] chitosan chloride has also been formulated together with α,β-glycerophosphate into a thermal-sensitive hydrogel (Wu et al., 2012). This hydrogel was shown a) to significantly prolong the antigen residence time in the nasal cavity, b) to enhance the transepithelial transport via the paracellular routes, and c) to induce in mice a high mucosal immunity (sIgA) and systemic immune response (IgG1 and IgG2a).

VIII.5. Liposome-Thermogelling Hydrogel Formulations

For sustained local delivery of PS-containing liposomes at the site of antigen or allergen presentation according to the method of the present invention, different liposome-hydrogel formulations are suitable (e.g., Xing et al., 2013; Nie et al., 2011).

In a preferred specific embodiment, thermo-sensitive copolymeric hydrogels composed of PLGA-PEG-PLGA are employed for sustained local delivery of PS-containing liposomes and, optionally, in combination with one or more 'find me' signals for efficient peripheral phagocytosis, one or more 'eat me' signals for enhanced phagocytosis, and individual combinations of Treg-modulating therapeutics capable of inhibiting unwanted local immune reactions at the site of antigen or allergen presentation. As demonstrated in a recent study, liposome-loaded PLGA-PEG-PLGA hydrogels exhibit still reversible thermo-sensitive properties (Xing et al., 2013). However, its sol-gel and gel-precipitate transition temperatures decreased with increasing liposome concentration. Most important, the particle size of free liposomes and those released from the PLGA-PEG-PLGA hydrogels were found to be close regardless of particle size of liposomes, indicating that the liposomes were stable in the hydrogel and intact liposomes could be released (Xing et al., 2013).

VIII.6. Stability of Thermo-Gelling Polymers

The various biodegradable thermo-gelling polymers provide different stability characteristics. For example, poloxamer triblock polymers provide excellent thermo-sensitivity, but due to weak hydrophobicity of the PPO block such copolymers form fast eroding gels which have been reported to persist in vivo a few hours at most. Exposure of poloxamer gels to phosphate-buffered saline under in vitro conditions demonstrated gel erosion within 2 days (Hyun et al., 2007). Similar results were observed when the polymer solutions were subcutaneously injected into rats. Remaining poloxamer gels could not be observed after 2 days (Hyun et al., 2007). Different results were obtained with MPEG-PCL gels. Under in vitro conditions MPEG-PCL gels maintained their structural integrity for more than 28 days and after subcutaneous injection into rats MPEG-PCL gels maintained their structural integrity longer than 30 days. The stability of MPEG-PCL gels, however, may also create problems since the rate of degradation of PCL in vivo is rather slow (2-3 years) compared to that of PLA, PGA or PLGA (for a review, see Sinha et al., 2004). Thus, after serving the function in delivering suitable Treg-modulating therapeutics, MPEG-PCL copolymers may remain in the body under physiological conditions for an uncertain period. Therefore, most preferred biodegradable thermo-gelling polymers for the method of the present invention are those which maintain their structural integrity for a few days but do not remain in the body for more than a month.

In a preferred embodiment of the present invention, biodegradable thermo-gelling polymers are used which allow to modify their degradation kinetics. For example, PLLA segments can be incorporated into the PCL segment of MPEG-PCL copolymers, since PLLA provides better accessibility of water to the ester bonds of PLLA which enhances the hydrolytic degradation of the copolymer (Kang et al., 2010). The resulting MPEG-b-(PCL-ran-PLLA) diblock copolymers offer a therapeutic window that is adjustable from a few weeks to a few months by varying the amount of PLLA in the PCL segment (Kang et al., 2010). In another example, the rate of PLGA-PEG-PLGA hydrogel erosion can be modified by altering the molar ratio of DL-lactide/glycolide in the PLGA segment. The DL-lactide moiety is more hydrophobic than the glycolide moiety. Therefore, by increasing the molar ratio of DL-lactide/glycolide in the PLGA segment of PLGA-PEG-PLGA triblock copolymers, more stable hydrogels are formed due to stronger hydrophobic interactions among the copolymer molecules (Qiao et al. 2005).

VIII.7. Release of Proteins from Thermogelling Polymers

Several of the biodegradable thermogelling polymers have been analyzed for their ability to mediate sustained release of proteins. Although different proteins are likely to affect the release behavior of each copolymer in individual ways, characterization of the release of model proteins such as bovine serum albumin (BSA) provides important information.

Using composite hydrogels containing different percentages of PECE and Pluronic F127, the in vitro release behavior of BSA proved to be dependent on the hydrogel composition, initial BSA loading amount, and hydrogel concentration (Gong et al., 2009b). Sustained release of BSA above 15 days was achieved with a composite hydrogel containing 60% PECE and 40% Pluronic F127, loaded with 4 mg BSA in the presence of 30 wt % hydrogel. Using MPEG-PCL copolymers, sustained in vitro release of BSA proved to be above 20 days, and under in vivo conditions (after subcutaneous injection into rats) sustained release lasted for more than 30 days (Hyun et al., 2007).

While for most clinical applications a sustained release of therapeutic drugs from biodegradable thermogelling polymers over a period of several weeks is desirable, the method of the present invention does not require such an extended sustained release of active substance since the development of immunologic memory requires the engagement of the T cell receptor (TCR) for a period of only 1 to 2 days. Therefore, preferred are biodegradable thermo-gelling polymers which deliver TNFR1 inhibitors for a limited period only which does not exceed a week.

In a preferred specific embodiment, triblock copolymers based on poly(lactide) (PLA) or poly)lactide-co-glycolide) (PLGA) and poly(ethylene glycol)(PEG) or poly(ethylene oxide) (PEO) blocks are employed for the method of the present invention. PLGA-PEG-PLGA triblock copolymers represent one example of hydrogels providing advantageous degradation and release kinetics for the method of the present invention. As demonstrated in a recent study, the release of insulin from PLGA-PEG-PLGA triblock copolymers lasted for approximately 4 days with an initial burst effect during the first day (Choi et al, 2003). The initial burst effect may be advantageous in the initial phase for effective phagocytosis by the release of 'find me' and 'eat me' signals as well as for effective inhibition of unwanted local immune reactions at the site of antigen or allergen presentation by the release of Treg-inducing immune modulators. However, the release kinetics from PLGA-PEG-PLGA triblock copolymers can be modified according to the requirements of individual therapeutic approaches. For example, modifying the copolymer composition and/or increasing the polymer concentration (e.g., from 25% (w/v) to 30% (w/v)) has been shown to decrease the burst release and to extend the release of proteins (Singh et al., 2007).

Although Poloxamer gels are not biodegradable, Poloxamer 407 (trade name Pluronic F127) gels represent also an example of thermogelling polymers providing advantageous degradation and release kinetics for the method of the present invention. Although under in vitro conditions the release of BSA from Poloxamer 407 gels proved to be almost complete within 1 day, the sustained release of BSA under in vivo conditions (after subcutaneous injection into rats) lasted for 3 days (Hyun et al., 2007).

Another important aspect of thermogelling polymers which are useful for the method of the present invention, is their ability to deliver proteins in biologically active forms. Examples of thermogelling polymers capable of releasing a protein in its native form include but are not limited to triblock copolymers based on poly(lactide) (PLA) or poly) lactide-co-glycolide) (PLGA) and poly(ethylene glycol) (PEG) or poly(ethylene oxide) (PEO) blocks. Utilizing such triblock copolymers, two model enzymes, lysozyme (N-acetylmuramide glycanhydrolase) and bromelain (cysteine protease), have been shown to be released from the triblock copolymers in biologically active forms (Singh et al., 2007).

VIII.8. Safety Aspects of PEG/PLA/PLGA-Based Hydrogels

Preferred biodegradable polymers include but are not limited to poly(ethylene glycol) (PEG), poly(D,L-lactic acid) (PLA), copolymers of L-lactic acid and D,L-lactic acid, poly(glycolic acid), and poly(lactic-co-glycolic acid) (PLGA). The use of these polymers as sustained-release protein delivery systems has been studied extensively (for a review, see Pai et al., 2009) and they represent the most compelling biodegradable polymers for depot systems due to their inclusion in the FDA's General Recognized as Safe (GRAS) list for use in medical devices and drug formulations (FDA, http://vm.cfsan.fda.gov/%7Edms/eafus.html, accessed at various dates).

IX. Fields of Application and Treatment Options

In one embodiment, the present invention discloses allergic and autoimmune diseases for which the method of the present invention is beneficial. Allergic diseases include but are not limited to allergic conjunctivitis, allergic rhinitis, and allergic asthma. Autoimmune diseases include but are not limited to type I diabetes, rheumatoid arthritis, and multiple sclerosis. For such diseases, the present invention discloses methods for restoring lasting immunological tolerance by allergen- or autoantigen-specific immunotherapy in combination with tolerance-promoting PS-containing liposomes, optionally containing encapsulated allergens/autoantigens or fragments thereof and/or one or more mediators of macrophage-induced immune suppression, one or more 'find me' signals for efficient peripheral phagocytosis, one or more 'eat me' signals for enhanced phagocytosis, and individual combinations of Treg-modulating therapeutics capable of inhibiting unwanted local immune reactions at the site of antigen or allergen presentation, all of them embedded in a matrix capable of mediating the sustained local supply of these therapeutics.

The present invention aims for immune intervention by targeting the molecular mechanisms of allergen or autoantigen tolerance and reciprocal regulation of effector and regulatory T cells. The locally restricted adjuvant therapy at the site of allergen presentation according to the method of the present invention is based on varying combinations of different therapeutic approaches, each of which addresses macrophage-induced immune suppression, the complex network of Treg induction and, thereby, reciprocal regulation of effector T cells by a different mechanism.

IX.1. Treatment of Allergy

Allergen-specific immunotherapy has been used for many decades as a desensitizing therapy for allergic diseases and represents the potentially curative method of treatment. Based on current knowledge, allergen tolerance is mediated by peripherally induced regulatory T cells as evidenced by a deficit of allergen-specific IL-10 producing T cells in the peripheral blood of allergic patients (for a review, see Schmidt-Weber et al., 2006). The limiting factor is anaphylactic side-effects, which vary in incidence from 0.1-5% of individuals depending on severity. Therefore, improved approaches are needed.

The present invention discloses methods for restoring lasting immunological tolerance by allergen-specific immunotherapy in combination with adjuvant therapeutic approaches which include various combinations of a) PS-containing liposomes (selected from those listed in section I), which optionally contain encapsulated allergens or fragments thereof and optionally one or more mediators of macrophage-induced immune suppression (selected from those listed in section V), and which optionally display one or more tolerance supporting liposomal surface ligands (selected from those listed in section IV), b) optionally one or more 'find me' signals (selected from those listed in section II), c) optionally one or more 'eat me' signals (selected from those listed in section III), d) individual combinations of Treg-modulating therapeutics capable of inhibiting unwanted local immune reactions at the site of allergen presentation (selected from those listed in section VI), e) optionally one or more adjuvant molecules (selected from those listed in section VII), and f) matrices for sustained local delivery of the embedded therapeutics (selected from those listed in section VIII).

Most important for adjuvant therapeutic approaches in combination with allergen-specific immunotherapy appears to be at the site of allergen presentation the combination of a) local production of the anti-inflammatory cytokines TGF-$\beta$ and IL-10 by macrophages upon phagocytosis of PS-containing liposomes, b) local inhibition of allergy promoting effects by IL-4/IL-13, c) local inhibition of complement, d) local inhibition of the production of proinflammatory cytokines by activated resident leukocyte populations such as Langerhans cells, dermal dendritic cells, and/or $\gamma\delta$-T cells via local administration of vitamin D3 or analogs thereof and/or local inhibition of TNFR1 and TNFR1-mediated pathways, and e) the sustained local supply of therapeutics capable of mediating the desired effects for a period of two or more days.

In one specific embodiment, PS-containing liposomes with encapsulated allergens are used to promote allergen-specific tolerance by macrophage-mediated phagocytosis in the presence of one or more 'find me' signals and, optionally, one or more 'eat me' signals. A recent study demonstrated that after uptake of PS-containing liposomes in vitro and in vivo macrophages secrete high levels of the anti-inflammatory cytokines TGF-$\beta$ and IL-10, concomitant with down-regulation of proinflammatory markers such as TNF$\alpha$ and the surface marker CD86 (Harel-Adar et al., 2011).

In another specific embodiment, interleukin variants capable of antagonizing the activity of IL-4 and IL-13 such as the double mutant of human IL-4 (R121D/Y124D) are used as inhibitors. Animal experiments in mice have demonstrated that inhibition of the IL-4/IL-13 receptor system can completely abrogate humoral immune response to allergen and development of allergic symptoms in vivo (Grunewald et al., 1998).

In another specific embodiment, low molecular weight agents capable of inhibiting locally synthesized complement component C3 are used for the method of the present invention. The impact of local inhibition of complement activation on the development of tolerance to allergens is evident from experiments with C3-deficient mice (Yalcindag et al., 2006). The study revealed that splenocytes from C3-deficient mice secreted less TH2-specific interleukins including IL-4, IL-5 and IL-13, and less TH1-specific IFN-$\gamma$ in response to OVA stimulation than splenocytes from wild-type control mice. C3-deficient mice had impaired IgG1, IgG2a, and IgE antibody responses after both epicutaneous and intraperitoneal immunization. It is important to note that the defect was corrected by the addition of purified C3 protein. One preferred low molecular weight inhibitor targeting complement component C3 is the 13-residue cyclic peptide (H-I[CVVQDWGHHRC]T-NH$_2$) which is able to bind selectively to primate C3 and its C3b and C3c fragments, and to inhibit cleavage of C3 by C3 convertases of both the classical and the alternative pathway.

In another specific embodiment, the vitamin D3 analogue calcipotriol, capable of inducing CD4+CD25+ Tregs and abolishing allergen-specific CD8+ T cell priming (Ghoreishi et al., 2009), is used to inhibit the production of proinflammatory cytokines. As shown in a recent study, 1,25-(OH)$_2$D3 promotes tolerogenic epidermal Langerhans cells (LCs) and dermal dendritic cells (DDCs), both of which are able to generate Treg cells with different effector functions. Treatment of epidermal LCs with 1,25-(OH)$_2$D3 generates functional Foxp3+ Tregs through a mechanism that is dependent on keratinocyte-derived TGF-β. In contrast, treatment of DDCs with 1,25-(OH)$_2$D3 generates functional IL-10+ FoxP3$^-$ T$_R$1 cells in an IL-10-dependent fashion (van der Aar et al., 2011).

In still another specific embodiment, thermo-sensitive copolymeric hydrogels composed of PLGA-PEG-PLGA are employed for sustained local delivery of therapeutics capable of mediating the desired effects.

IX.2. Treatment of Allergic Asthma

According to a review of 75 trials covering a total of 3,188 patients with asthma, SCIT (subcutaneous immunotherapy) led to a significant reduction in asthma symptom scores, medication use and airway hyper-responsiveness, with evidence of a dose-related effect (Abramson et al., 2003). SCIT and SLIT (sublingual immunotherapy) also decrease the development of sensitization to new allergens and decrease the risk of new asthma in both adults and children with rhinitis. A recent retrospective cohort study of 322 subjects with allergic rhinitis showed that 53.1% of subjects who were not treated with SCIT developed asthma, whereas only 41.6% of subjects who received SCIT were diagnosed with asthma (for a review, see Holgate and Polosa, 2008).

Taken together, immunotherapy has been proven efficacious in treating mild asthma, as well as in preventing the progression to asthma in patients suffering from rhinoconjunctivitis (Moller et al., 2002; Jacobsen et al., 2007), but it is not yet recommended for the treatment of moderate to severe asthmatic patients (Rolland et al., 2009). Therefore, new strategies are required that are capable to reconstitute regulatory responses in combination with allergen-specific immunotherapy. Since Treg cells are key players in maintaining homeostasis within the lung, enhancement of the proliferation, Foxp3 expression and the suppressive activity of Tregs in support of allergen-specific immunotherapy by Treg-modulating therapeutics at the site of allergen presentation represents an attractive adjuvant therapeutic approach.

The present invention discloses methods for restoring lasting immunological tolerance by allergen-specific immunotherapy in combination with adjuvant therapeutic approaches which include various combinations of a) PS-containing liposomes (selected from those listed in section I), which optionally contain encapsulated allergens or fragments thereof and optionally one or more mediators of macrophage-induced immune suppression (selected from those listed in section V), and which optionally display one or more tolerance supporting liposomal surface ligands (selected from those listed in section IV), b) optionally one or more 'find me' signals (selected from those listed in section II), c) optionally one or more 'eat me' signals (selected from those listed in section III), d) individual combinations of Treg-modulating therapeutics capable of inhibiting unwanted local immune reactions at the site of allergen presentation (selected from those listed in section VI), e) optionally one or more adjuvant molecules (selected from those listed in section VII), and f) matrices for sustained local delivery of the embedded therapeutics (selected from those listed in section VIII).

Most important for adjuvant therapeutic approaches in combination with allergen-specific immunotherapy appears to be at the site of allergen presentation the combination of a) local production of the anti-inflammatory cytokines TGF-β and IL-10 by macrophages upon phagocytosis of PS-containing liposomes, b) local inhibition of allergy promoting effects by IL-4/IL-13, c) local inhibition of complement, d) local inhibition of the production of proinflammatory cytokines by activated resident leukocyte populations such as Langerhans cells, dermal dendritic cells, and/or γδ-T cells via local administration of vitamin D3 or analogs thereof and/or local inhibition of TNFR1 and TNFR1-mediated pathways, and e) the sustained local supply of therapeutics capable of mediating the desired effects for a period of two or more days.

In one specific embodiment, PS-containing liposomes with encapsulated allergens are used to promote allergen-specific tolerance by macrophage-mediated phagocytosis in the presence of one or more 'find me' signals and, optionally, one or more 'eat me' signals. A recent study demonstrated that after uptake of PS-containing liposomes in vitro and in vivo macrophages secrete high levels of the anti-inflammatory cytokines TGF-β and IL-10, concomitant with downregulation of proinflammatory markers such as TNFα and the surface marker CD86 (Harel-Adar et al., 2011).

In another specific embodiment, interleukin variants capable of antagonizing the activity of IL-4 and IL-13 such as the double mutant of human IL-4 (R121D/Y124D) are used as inhibitors. The effect of the double mutant of IL-4 (R121D/Y124D) on late phase asthmatic response to allergen challenge in asthmatic patients has been evaluated recently in clinical studies (Wenzel et al., 2007). The studies demonstrate that dual inhibition of IL-4 and IL-13 can positively affect the course of late asthmatic response after experimental allergen challenge. Treatment with the double mutant was associated with few adverse events, whether administered by subcutaneous injection (up to 30 mg for up to 13 weeks) or by inhalation (up to 60 mg for up to 4 weeks) in participants with atopic asthma or atopic eczema.

In another specific embodiment, low molecular weight agents capable of inhibiting locally synthesized complement component C3 are used for the method of the present invention. In the past decade, an important role for complement in the pathogenesis of allergic asthma has been uncovered. Several studies have demonstrated complement activation in human and experimental allergic asthma. Furthermore, blockade of complement activation with the mouse membrane complement inhibitor Crry (complement receptor-related gene y) and by targeting C3, C5, C3aR (C3a receptor) or C5aR (C5a receptor) during the allergic effector phase has been shown to decrease the alleric phenotype in different models of experimental allergic asthma (for a review, see Zhang and Kohl, 2010). One preferred low molecular weight inhibitor targeting complement component C3 is the 13-residue cyclic peptide (H-I[CVVQDWGHHRC]T-NH$_2$) which is able to bind selectively to primate C3 and its C3b and C3c fragments, and to inhibit cleavage of C3 by C3 convertases of both the classical and the alternative pathway.

In another specific embodiment, the vitamin D3 analogue calcipotriol capable of inducing CD4+CD25+ Tregs and abolishing allergen-specific CD8+ T cell priming (Ghoreishi et al., 2009), is used to inhibit the production of proinflammatory cytokines. Evidence for the beneficial effect of vitamin D on the symptoms and laboratory parameter associated with allergic asthma comes from in vitro and in vivo studies. For example, vitamin D receptor (VDR)-deficient mice (VDR-KO) failed to develop experimental allergic asthma (Wittke et al., 2004). VDR-KO mice did develop antigen-specific Th2 cell responses, but failed to develop lung inflammation or airway hyper-responsiveness. The absence of vitamin D signaling through VDRs protected these mice from developing experimental allergic asthma. Furthermore, in a mouse model of ovalbumin (OVA)-induced allergic asthma 1,25-$(OH)_2D3$ has been demonstrated to potentiate the beneficial effects of allergen immunotherapy (Taher et al., 2008). Co-administration of 10 ng 1,25-$(OH)_2D3$ with 100 μg of OVA immunotherapy significantly inhibited airway hyper-responsiveness (AHR) and potentiated the reduction of serum OVA-specific IgE levels, airway eosinophilia, and Th2-related cytokines concomitant with increased IL-10 levels in lung tissues and TGF-β and OVA-specific IgA levels in serum. Omission of 1,25-$(OH)_2D3$ during immunotherapy resulted in partial suppression of bronchioalveolar lavage eosinophilia, but no reduction of AHR (Taher et al., 2008).

In still another specific embodiment, thermo-sensitive copolymeric hydrogels composed of PLGA-PEG-PLGA are employed for sustained local delivery of therapeutics capable of mediating the desired effects.

IX.3. Treatment of Diabetes Type 1

Adverse effects of the therapeutic approaches with broad immune-suppressive agents as well as the lack of permanent remission of disease with any agent tested to date have boosted interest in the development of antigen-specific interventions. Such an approach may require only a single beta-cell-derived antigen despite the polyclonal nature of the autoimmune response, reflected by the presence of multiple autoantibodies and multiple T cell epitopes that are recognized by peripheral blood cells. Immunological tolerance mechanisms, even by antigen-specific cells, are not restricted to a single antigen. Cytokines such as IL-10 and TGF-β, produced by T cells in response to antigen or antigen-presenting cells, can modulate the function of effector T cells in the vicinity of the antigen. Thereby, activated regulatory T cells can exert their function at the site of the immune response without the need to recognize those antigen(s) recognized by effector T cells. In addition, CD4+ CD25+ Foxp3+ and other regulatory T cells are able to modulate the function of effector T cells through contact-dependent mechanisms. It has been demonstrated that polyclonal diabetogenic T cells can be inhibited by antigen-specific Treg cells in vitro and in an adoptive transfer model of diabetes (for a review, see Bluestone et al., 2010).

A promising approach is the vaccination with the 65 kDa isoform of glutamic acid decarboxylase (GAD65). Immunization with alum-GAD65 was shown to attenuate the loss of C-peptide in individuals treated within six months of diagnosis (Ludvigsson et al., 2008). Furthermore, oral insulin administration yielded also promising results in a subset of patients with high levels of insulin autoantibodies (Skyler et al., 2005), an observation that is now being studied in detail. These data support the concept that an antigen-specific intervention may have broad immunological effects, provided the selected antigen is directly involved in the disease pathogenesis and/or regulation. Phase III trials with alum-GAD65 are underway in the USA and in Europe (Diamyd, 2011a and 2011b). In addition, prevention studies are underway in which this vaccine is given to persons who have not yet developed type 1 diabetes (Diamyd, 2011c).

Taken together, auto-antigen-specific immunotherapy has been proven efficacious for the treatment of patients with type 1 diabetes, provided the therapy is initiated shortly after diagnosis of the disease. There is no question, however, that current immunotherapeutic approaches need to be optimized. The present invention provides methods that are capable to reconstitute regulatory responses in combination with auto-antigen-specific immunotherapy.

The present invention discloses methods for restoring lasting immunological tolerance by autoantigen-specific immunotherapy in combination with adjuvant therapeutic approaches which include various combinations of a) PS-containing liposomes (selected from those listed in section I), which optionally contain encapsulated autoantigens or fragments thereof and optionally one or more mediators of macrophage-induced immune suppression (selected from those listed in section V), and which optionally display one or more tolerance supporting liposomal surface ligands (selected from those listed in section IV), b) optionally one or more 'find me' signals (selected from those listed in section II), c) optionally one or more 'eat me' signals (selected from those listed in section III), d) individual combinations of Treg-modulating therapeutics capable of inhibiting unwanted local immune reactions at the site of allergen presentation (selected from those listed in section VI), e) optionally one or more adjuvant molecules (selected from those listed in section VII), and f) matrices for sustained local delivery of the embedded therapeutics (selected from those listed in section VIII).

Most important for the adjuvant therapeutic approaches appears to be at the site of autoantigen presentation the combination of a) local production of the anti-inflammatory cytokines TGF-β and IL-10 by macrophages upon phagocytosis of PS-containing liposomes, b) local inhibition of complement activation, in particular local inhibition of C3a-C3aR and C5a-C5aR interactions, c) local inhibition of the production of proinflammatory cytokines by activated resident leukocyte populations such as Langerhans cells, dermal dendritic cells, and/or γδ-T cells via local administration of vitamin D3 or analogs thereof and/or local inhibition of TNFR1 and TNFR1-mediated pathways, and d) the sustained local supply of therapeutics capable of mediating the desired effects for a period of two or more days.

In one specific embodiment, PS-containing liposomes with encapsulated autoantigens are used to promote autoantigen-specific tolerance by macrophage-mediated phagocytosis in the presence of one or more 'find me' signals and, optionally, one or more 'eat me' signals. The tolerance-promoting effect of PS-containing liposomes is supported by several animal studies. For example, PS-containing liposomes have been demonstrated to inhibit responses in mice to antigens as determined by decreased draining lymph node tissue mass, reduced numbers of total leukocytes and antigen-specific CD4+ T cells and decreased levels of antigen-specific IgG in blood. TGF-β appears to play a critical role in this inhibition, as the inhibitory effects of PS-containing liposomes were reversed by in vivo administration of anti-TGF-β antibodies (Hoffmann et al., 2005).

In another specific embodiment, low molecular weight agents capable of inhibiting locally synthesized complement component C3 are used for the method of the present invention. One preferred low molecular weight inhibitor targeting complement component C3 is the 13-residue cyclic peptide (H-I[CVVQDWGHHRC]T-$NH_2$) which is able to bind selectively to primate C3 and its C3b and C3c fragments, and to inhibit cleavage of C3 by C3 convertases of both the classical and the alternative pathway. In animal studies, immune cell-derived C3, C3a receptors and C5a receptors have been demonstrated to be essential for the development of T cell-dependent type 1 diabetes induced by multiple low doses of streptozotocin (Lin et al., 2010). Although the results of this study have been questioned (Ostergard et al., 2011), another recent study in mice has confirmed that complement C3 deficiency prevents against the onset of streptozotocin-induced autoimmune diabetes involving expansion of regulatory T cells (Gao et al., 2011). Higher numbers of CD4+CD25+Treg cells with characteristics of expressing Foxp3 were observed in C3−/− mice. The central role of Tregs was further evidenced by that depleting these cells using anti-CD25 antibody dramatically abrogated the preventive effects of C3 deficiency on streptozotocin-induced autoimmune diabetes. Importantly, transforming growth factor beta (TGF-β) proved to be a key factor for Treg-mediated immune suppression (Gao et al., 2011).

In another specific embodiment, the vitamin D3 analogue calcipotriol capable of inducing CD4+CD25+ Tregs and abolishing antigen-specific CD8+ T cell priming (Ghoreishi et al., 2009), is used to inhibit the production of proinflammatory cytokines. Strong evidence of a vitamin D3 effect on type I diabetes risk comes from experiments in the non-obese diabetic (NOD) mouse which exhibits a disease pathogenesis similar to that of humans including autoimmune destruction of beta cells. When 1,25-(OH)$_2$D3 was administered to NOD mice in pharmacological doses, it prevented the development of diabetes (Mathieu et al., 1994). The same observation was also made in a later animal study (Zella et al., 2003). Another recent study demonstrated that NOD mice raised in a vitamin D deficient state developed diabetes at an earlier age than non-deficient NOD controls (Giulietti et al., 2004).

In still another specific embodiment, thermo-sensitive copolymeric hydrogels composed of PLGA-PEG-PLGA are employed for sustained local delivery of therapeutics capable of mediating the desired effects.

IX.4. Treatment of Rheumatoid Arthritis (RA)

Anti-TNF therapy with TNF-alpha blockers (e.g., Infliximab, Adalimumab, Etanercept) has been shown to ameliorate clinical symptoms and laboratory parameters of inflammation in the majority of RA patients. However, despite the beneficial therapeutic effects of TNF-alpha blockers for RA patients, long-term use of these inhibitors can cause serious side effects including an increased incidence of infections. For example, in a retrospective analysis of 709 patients treated with at least one TNF-alpha blocker, 34.5% of patients reported infectious complications during the treatment period, with 6.2% falling under the category of serious infections (for a review, see Ichim et al., 2008).

Furthermore, clinical inhibition of inflammatory cytokines does not lead to a long-term cure. Therefore, various approaches for the induction of autoantigen-specific tolerance have been tested (for a review, see Ichim et al., 2008). In animal models, immune suppressive epitopes of collagen II have been identified that induce protection from disease. However, the majority of clinical work has been performed targeting the autoantigen hsp60. For example, a clinical trial using hsp60 peptides demonstrated clinical remission in patients with juvenile RA (Kamphuis et al., 2005). Recently, a multicentre, double-blind, placebo-controlled, autoantigen-specific immuno-therapy study was performed using the human cartilage glycoprotein-39 (HCgp-39) (Landewe et al., 2010). HCgp-39 was administered via the intranasal route since the nasal mucosa is currently regarded as the most powerful route for induction of immunological tolerance (Higuchi et al., 2000). However, the used treatment protocol did not result in more clinical improvement than in placebo-controlled patients, although HCgp-39 has been identified as a key autoantigen in RA. Based on these examples it becomes clear that autoantigen-specific immunotherapy appears to be feasible, but in its present state the antigen-specific suppression is too weak for widespread clinical implementation. In order to develop more potent protocols, there is a need for concomitant inhibition of effector T cells and the induction of regulatory T cells along with autoantigen presentation. The present invention provides methods that are capable to reconstitute regulatory responses in combination with autoantigen-specific immunotherapy.

The present invention discloses methods for restoring lasting immunological tolerance by autoantigen-specific immunotherapy in combination with adjuvant therapeutic approaches which include various combinations of a) PS-containing liposomes (selected from those listed in section I), which optionally contain encapsulated autoantigens or fragments thereof and optionally one or more mediators of macrophage-induced immune suppression (selected from those listed in section V), and which optionally display one or more tolerance supporting liposomal surface ligands (selected from those listed in section IV), b) optionally one or more 'find me' signals (selected from those listed in section II), c) optionally one or more 'eat me' signals (selected from those listed in section III), d) individual combinations of Treg-modulating therapeutics capable of inhibiting unwanted local immune reactions at the site of allergen presentation (selected from those listed in section VI), e) optionally one or more adjuvant molecules (selected from those listed in section VII), and f) matrices for sustained local delivery of the embedded therapeutics (selected from those listed in section VIII).

Most important for the adjuvant therapeutic approaches appears to be at the site of autoantigen presentation the combination of a) local production of the anti-inflammatory cytokines TGF-β and IL-10 by macrophages upon phagocytosis of PS-containing liposomes, b) local inhibition of TNFR1 and TNFR1-mediated pathways, c) local inhibition of the production of proinflammatory cytokines by activated resident leukocyte populations such as Langerhans cells, dermal dendritic cells, and/or γδ-T cells via local administration of vitamin D3 or analogs thereof (in addition to local administration of inhibitors of TNFR1 and TNFR1-mediated pathways), d) inhibition of C5aR-dependent auto-reactive T cell responses, and e) the sustained local supply of therapeutics capable of mediating the desired effects for a period of two or more days.

In one specific embodiment, PS-containing liposomes with encapsulated autoantigens or fragments thereof are used to promote autoantigen-specific tolerance by macrophage-mediated phagocytosis in the presence of one or more 'find me' signals and, optionally, one or more 'eat me' signals. The tolerance-promoting effect of PS-containing liposomes is supported by several animal studies. For example, PS-containing liposomes have been demonstrated to inhibit responses in mice to antigens as determined by decreased draining lymph node tissue mass, reduced numbers of total leukocytes and antigen-specific CD4+ T cells and decreased levels of antigen-specific IgG in blood. TGF-β appears to play a critical role in this inhibition, as the inhibitory effects of PS-containing liposomes were reversed by in vivo administration of anti-TGF-β antibodies (Hoffmann et al., 2005).

In another specific embodiment, low molecular weight agents capable of inhibiting TNFR1 and TNFR1-mediated pathways are used to inhibit inflammatory immune reactions. Important evidence for the involvement of TNF-alpha in RA came from studies with mice over-expressing human TNF-alpha and spontaneously developing polyarthritis. Successful treatment of these mice with an anti-TNF-alpha antibody demonstrated the detrimental role of TNF-alpha in this model. Currently, different mouse models are used to study arthritis. One model of TNF-alpha-induced arthritis is the TNFdARE mouse. In this mouse, deletion of the ARE region in the 3'UTR of the TNF-alpha mRNA stabilizes the mRNA and, thereby, causes continuous production of TNF-alpha. These animals develop spontaneous polyarthritis and small bowel inflammation resembling Crohn's disease. When crossed with TNFR1 deficient mice, TNFdARE mice do not develop arthritis, but crossing with TNFR2 KO mice leads to exacerbation of disease progression. This indicates that TNFR1-mediated signaling is pathologic, whereas TNFR2-mediated signaling induces anti-inflammatory effects. In a preferred specific embodiment, SA and related salicylates are used for the method of the present invention. In another preferred specific embodiment, TNFR1-specific antisense oligonucleotides are used for the method of the present invention. Although synovial fibroblasts have been identified as the primary targets for TNF-alpha in the development of arthritis, the site for selective inhibition of TNFR1-mediated functions does not appear to be critical for the therapeutic effect. As demonstrated in a recent study, systemic treatment with an adenoviral vector containing a short hairpin RNA directed against TNFR1 ameliorated collagen-induced arthritis (CIA) in mice almost to the same extent as local treatment (Arntz et al., 2010).

In another specific embodiment, the vitamin D3 analogue calcipotriol, capable of inducing CD4+CD25+ Tregs and abolishing antigen-specific CD8+ T cell priming (Ghoreishi et al., 2009) is used, in addition to inhibitors of TNFR1 and TNFR1-mediated pathways, to inhibit the production of proinflammatory cytokines. Strong evidence for an inhibitory effect of vitamin D3 on the progression of autoimmune arthritis comes from two different animal models of arthritis, namely murine Lyme arthritis and collagen-induced arthritis (Cantorna et al., 1998). Infection of mice with *Borrelia burgdorferi*, the causative agent of human Lyme arthritis, produced arthritic lesions including footpad and ankle swelling. Supplementation with 1,25-dihydroxycholecalciferol of an adequate diet fed to mice infected with *B. burgdorferi* minimized or prevented these symptoms. Mice immunized with type II collagen also developed arthritis. The symptoms of this disease were also prevented by dietary supplementation with 1,25-dihydroxycholecalciferol (calcitriol).

In another specific embodiment, low molecular weight immune modulators targeting complement-mediated pathways are used to inhibit C5aR-dependent auto-reactive T cell responses. Inhibition of locally produced complement appears to be beneficial, since a recent study has demonstrated that the interaction of serum-derived C5a with immune cell-expressed C5aR is an essential mediator in an IL-17-dependent model of autoimmune arthritis (Hashimoto et al., 2010).

In still another specific embodiment, thermo-sensitive copolymeric hydrogels composed of PLGA-PEG-PLGA are employed for sustained local delivery of therapeutics capable of mediating the desired effects.

IX.5. Treatment of Multiple Sclerosis (MS)

Several attempts have been made to apply self-antigen-specific immunotherapy in MS patients including DNA vaccines encoding myelin proteins (e.g., Garren et al., 2008), myelin proteins and myelin protein-derived peptides (for a review, see Steinman and Zamvil, 2010). Key autoantigens in MS include myelin basic protein (MBP), proteolipid protein (PLP) and myelin oligodendrocyte glycoprotein (MOG). In clinical trials, oral application of myelin proteins (Faria and Weiner, 2005) and intravenous application of MBP (Warren et al., 2006) showed no or only modest effects on MS disease course. However, a recent clinical trial in 30 relapsing-remitting MS patients with transdermally applied peptides derived from three myelin proteins (MBP, PLP, MOG) induced immune tolerogenic effects (Jurynczyk et al., 2010). The transdermally applied peptides activated dendritic Langerhans cells in the skin at the site of immunization, induced a unique population of granular dendritic cells in local lymph nodes, and generated type 1, IL-10-producing Tregs in the periphery. Repeated transdermal application of these peptides (weekly in the first month and then monthly for the remainder of the year) resulted in suppression of specific autoreactive proliferative responses and suppression of IFN-γ and TGF-β production.

A random copolymer of alanine, lysine, glutamic acid and tyrosine (glatiramer acetate, known also as Copaxone or Copolymer 1) has also been shown to slow the progression of disability and to reduce relapse rate (for reviews, see Amon and Aharoni, 2004; Arnon, 1996). The mode of action of glatiramer is by strong promiscuous binding to MHC molecules and consequent competition with various myelin antigens for their presentation to T cells. A further aspect of its action is potent induction of specific suppressor cells of the Th2 type that migrate to the brain and lead to in situ bystander suppression. Furthermore, the glatiramer-specific cells in the brain express the anti-inflammatory cytokines IL-10 and TGF-β, whereas they do not express IFN-γ (for a review, see Amon and Aharoni, 2004).

Application of fusion proteins containing GM-CSF coupled to myelin autoantigens for immunotherapy of EAE in mice (Abbott et al., 2011) have demonstrated that autoantigen-based vaccination approaches can be optimized by combining auto-antigen presentation with immune response-modulating agents. GM-CSF is recognized as a potent regulatory cytokine able to ameliorate disease in several mouse models of autoimmunity. For example, GM-CSF drives differentiation of dendritic cells (DCs), including tolerogenic DC subsets that in turn facilitate Treg differentiation and antigen-specific tolerance. In mice with EAE, a fusion protein of GM-CSF and the encephalitogenic MOG35-55 peptide facilitated tolerance rather than immunity to dominant self-epitopes of myelin (Abbott et al., 2011). In patients, however, therapeutic applications of GM-CSF can be associated with serious side effects such as the vascular leak syndrome. Therefore, alternative approaches are needed that employ more suitable enhancers of autoantigen-specific immunotherapy.

The present invention discloses methods for restoring lasting immunological tolerance by autoantigen-specific immunotherapy in combination with adjuvant therapeutic approaches which include various combinations of a) PS-containing liposomes (selected from those listed in section I), which optionally contain encapsulated autoantigens or fragments thereof and optionally one or more mediators of macrophage-induced immune suppression (selected from those listed in section V), and which optionally display one or more tolerance supporting liposomal surface ligands (selected from those listed in section IV), b) optionally one or more 'find me' signals (selected from those listed in section II), c) optionally one or more 'eat me' signals (selected from those listed in section III), d) individual combinations of Treg-modulating therapeutics capable of inhibiting unwanted local immune reactions at the site of allergen presentation (selected from those listed in section VI), e) optionally one or more adjuvant molecules (selected from those listed in section VII), and f) matrices for sustained local delivery of the embedded therapeutics (selected from those listed in section VIII).

Most important for the adjuvant therapeutic approaches appears to be at the site of autoantigen presentation the combination of a) local production of the anti-inflammatory cytokines TGF-β and IL-10 by macrophages upon phagocytosis of PS-containing liposomes, b) local administration of vitamin D3 or analogs thereof, c) local inhibition of the production of proinflammatory cytokines by activated resident leukocyte populations such as Langerhans cells, dermal dendritic cells, and/or γδ-T cells via local inhibition of TNFR1 and TNFR1-mediated pathways (in addition local administration of vitamin D3 or analogs thereof), d) inhibition of C3aR- and C5aR-dependent auto-reactive T cell responses, and e) the sustained local supply of therapeutics capable of mediating the desired effects for a period of two or more days.

In one specific embodiment, PS-containing liposomes with encapsulated autoantigens are used to promote autoantigen-specific tolerance by macrophage-mediated phagocytosis in the presence of one or more 'find me' signals and, optionally, one or more 'eat me' signals. Liposomes containing PS have the potential to mimic the anti-inflammatory effect of apoptotic cells. For example, intraperitoneal injection of PS-containing liposomes has been shown to ameliorate the course of extrinsic allergic encephalitis induced in mice by immunization with myelin basic protein (Monastra et al., 1993).

In another specific embodiment, the vitamin D3 analogue calcipotriol capable of inducing CD4+CD25+ Tregs and abolishing antigen-specific CD8+ T cell priming (Ghoreishi et al., 2009), is used. The role of vitamin D in experimental autoimmune encephalomyelitis (EAE) has been investigated in several studies (for a review, see Fletcher et al., 2012). The data indicate that the role of vitamin D is complex and point to a dual role of vitamin D at different concentrations in vivo. A basic level appears to be necessary for normal immune activation, whereas administration of higher levels of vitamin D can exert immunomodulatory functions. For example, prophylactic feeding of mice with relatively high doses of 1,25-$(OH)_2$D3 has been demonstrated to suppress the development of EAE (for a review, see Plum and DeLuca, 2010). High doses of 1,25-$(OH)_2$D3 are known to be associated with adverse side effects and the required dose of 1,25$(OH)_2$D3 for complete prevention of EAE has been shown to induce hypercalcemia. However, in contrast to systemic administrations of vitamin D3 via feeding, the present invention allows application of lower doses to achieve suppressive immunomodulatory functions. According to the method of the present invention, vitamin D3 or analogs thereof are embedded in a hydrogel together with the auto-antigen. Upon release from the hydrogel, even lower doses of vitamin D3 generate relatively high local concentration of vitamin D3 or analogs in close proximity of the auto-antigen during presentation by APCs to T cells. Upon diffusion away from the site of auto-antigen presentation, the concentration of vitamin D3 or analogs thereof decreases rapidly, thereby minimizing potential side effects. Furthermore, application of calcipotriol reduces the risk of potential side effects to a minimized level. As compared to 1,25-$(OH)_2$D3, calcipotriol has 100-200 times less effect on calcium metabolism including activation of calcium absorption and bone calcium mobilization (Kissmeyer and Binderup, 1991), and the half-life of calcipotriol in circulation is measured in minutes (Kragballe, 1995).

In another specific embodiment, low molecular weight agents capable of inhibiting TNFR1 and TNFR1-mediated pathways are used to inhibit inflammatory immune reactions. In one preferred specific embodiment, TNFR1-specific antisense oligonucleotides and/or SA and related salicylates are used for the method of the present invention. Of interest for a therapeutic design is that the two opposing functions of TNF-alpha diverge at the level of TNF receptors. In the murine EAE model, TNFR1 was found to be responsible for the detrimental signals, whereas TNFR2 was found to be essential for resolving inflammation and initiating repair (Kassiotis and Kollias, 2001). Accordingly, EAE was exacerbated in TNFR2-KO mice and reduced in TNFR1-KO mice (Suvannavejh et al., 2000). Interestingly, mutant mice expressing uncleavable transmembrane TNF-alpha (mTNF-alpha) were protected against autoimmunity, indicating that sTNF-alpha/TNFR1 interactions are responsible for the pathology (Alexopoulou et al., 2006). In agreement with these data, specific inhibition of TNFR1 by a pegylated mutant TNF molecule (PEG-R1antTNF) was shown to ameliorate the clinical symptoms in the EAE model (Nomura et al., 2011).

In another specific embodiment, low molecular weight immune modulators targeting complement-mediated pathways are used to inhibit C3aR- and C5aR-dependent auto-reactive T cell responses. Animal studies have provided strong evidence that complement may have an important role in MS. Using a murine model of experimental allergic encephalomyelitis (T cell-mediated autoimmunity that mimics aspects of human multiple sclerosis), $DAF^{-/-}$ mice developed more severe paralysis (associated with enhanced IL-17 production) upon immunization with myelin oligodendrocyte glycoprotein than wild-type mice (Liu et al., 2008). The stronger auto-reactive T cell response in $DAF^{-/-}$ mice is C3aR- and C5aR-dependent since mice deficient in either or both of these receptors develop weaker auto-reactive T cell responses and are resistant to the development of experimental allergic encephalomyelitis, regardless of DAF expression (Strainic et al., 2008).

In still another specific embodiment, thermo-sensitive copolymeric hydrogels composed of PLGA-PEG-PLGA are employed for sustained local delivery of therapeutics capable of mediating the desired effects.

X. Compositions for the Treatment of Allergic and Autoimmune Diseases

In one embodiment, the present invention discloses compositions for the treatment of allergic and autoimmune diseases suitable for one-step and two-step immunotherapeutic procedures.

X.1. One-Step Administration Procedures for Locally Restricted Treatment

In one embodiment, the present invention discloses compositions for one-step administration procedures for locally restricted treatment comprising a) one or more allergens/autoantigens or one or more fragments thereof, b) PS-containing liposomes (selected from those listed in section I), which optionally contain one or more mediators of macrophage-induced immune suppression (selected from those listed in section V), and which optionally display one or more tolerance supporting liposomal surface ligands (selected from those listed in section IV), c) optionally one or more 'find me' signals (selected from those listed in section II), d) optionally one or more 'eat me' signals (selected from those listed in section III), e) individual combinations of Treg-modulating therapeutics capable of inhibiting unwanted local immune reactions at the site of allergen presentation (selected from those listed in section VI), f) optionally one or more adjuvant molecules (selected from those listed in section VII), and g) matrices for sustained local delivery of the embedded components (selected from those listed in section VIII).

In a specific embodiment, a biodegradable thermogelling polymer solution is used for sustained delivery of the components (selected from those listed in section VIII). The quantity of each component in the biodegradable thermogelling polymer is balanced in a way that a) upon injection into the body the polymer forms a non-flowing gel in which the other components are embedded, and b) upon gelation of the polymer composite at body temperature the amount of released components is sufficient for the therapeutic aims of the method of the present invention.

In another specific embodiment, allergens/autoantigens or fragments thereof are encapsulated in PS-containing liposomes.

In another specific embodiment, allergens/autoantigens or fragments thereof are attached to the surface of PS-containing liposomes.

In another specific embodiment, allergens/autoantigens or fragments thereof are embedded in a suitable matrix in the presence or absence of one or more suitable adjuvants.

In another specific embodiment, equimolar quantities of ATP and UTP at a concentration of about 100 nM are embedded in a suitable matrix as 'find me' signals.

In another specific embodiment, annexin I (annexin A1, ANXA1), a 38 kDa protein, are embedded in a suitable matrix as additional 'eat me' signal. ANXA1 binds to PS on PS-containing liposomes in a calcium-dependent manner.

In another specific embodiment, one or more Treg-modulating therapeutics are embedded in a suitable matrix. Preferred individual combinations for allergic and autoimmune diseases are listed in section IX.

X.2. One-Step Administration Procedures for Systemic Treatment

In another embodiment, the present invention discloses compositions for systemic administrations of one or more allergens or antigens, or fragments thereof, or one or more allergen extracts embedded in PS-containing liposomes (selected from those listed in section I). Optionally, these liposomes may display one or more surface-attached 'eat me' signals (selected from those listed in section III) and one or more mediators of macrophage-induced immune suppression (selected from those listed in section V).

In another embodiment, the present invention discloses compositions for systemic administrations of one or more allergens or antigens, or fragments thereof, covalently attached to the surface of PS-containing liposomes (selected from those listed in section I). Optionally, these liposomes may also display one or more suitable surface-attached 'eat me' signals (selected from those listed in section III) and one or more mediators of macrophage-induced immune suppression (selected from those listed in section V).

X.3. Two-Step Administration Procedures for Locally Restricted Treatment

In another embodiment, the present invention discloses compositions for two-step administration procedures for locally restricted treatment including administration of composition A comprising one or more allergens/autoantigens or one or more fragments thereof, and a) optionally one or more adjuvants (selected from those listed in section VI), followed by administration of composition B at the site of administered composition A, comprising tolerance-promoting PS-containing liposomes (selected from those listed in section I), which b) optionally contain one or more mediators of macrophage-induced immune suppression (selected from those listed in section V), and which optionally display one or more tolerance supporting liposomal surface ligands (selected from those listed in section IV), c) optionally one or more 'find me' signals (selected from those listed in section II), d) optionally one or more 'eat me' signals (selected from those listed in section III), e) individual combinations of Treg-modulating therapeutics capable of inhibiting unwanted local immune reactions at the site of allergen presentation (selected from those listed in section VI), and f) matrices for sustained local delivery of the embedded components (selected from those listed in section VIII).

In a specific embodiment, composition A comprises aluminum-containing adjuvants, typically aluminum phosphate or aluminum hydroxide gels (generally referred to as alum) for prolonged presentation of allergens/autoantigens or fragments thereof.

In another specific embodiment, composition B comprises a biodegradable thermogelling polymer solution for sustained delivery of the low molecular weight immune modulators. The quantity of each component in the biodegradable thermogelling polymer is balanced in a way that a) upon injection into the body the polymer forms a non-flowing gel in which the other components are embedded, and b) upon gelation of the polymer composite at body temperature the amount of released immune modulators is sufficient for the therapeutic aims of the method of the present invention.

In another specific embodiment, equimolar quantities of ATP and UTP at a concentration of about 100 nM are embedded in a suitable matrix as 'find me' signals.

In another specific embodiment, annexin I (annexin A1, ANXA1), a 38 kDa protein, are embedded in a suitable matrix as additional 'eat me' signal. ANXA1 binds to PS on PS-containing liposomes in a calcium-dependent manner.

In another specific embodiment, one or more Treg-modulating therapeutics are embedded in a suitable matrix. Preferred individual combinations for allergic and autoimmune diseases are listed in section IX.

X.4. Two-Step Administration Procedures for Systemic Treatment

In another embodiment, the present invention discloses compositions for two-step systemic administration procedures including administration of composition A comprising one or more allergens/autoantigens or one or more fragments thereof, either embedded in PS-containing liposomes (selected from those listed in section I), or covalently attached to the surface of PS-containing liposomes (selected from those listed in section I) Optionally, these liposomes may also expose one or more surface-attached 'eat me' signals (selected from those listed in section III) and/or one or more mediators of macrophage-induced immune suppression (selected from those listed in section V). Composition B comprises one or more therapeutics capable of supporting the establishment of tolerance. For example, for patients suffering from allergy or allergic asthma preferred therapeutics for this purpose include but are not limited to systemic anti-IgE therapeutics. For patients with type I diabetes preferred therapeutics for this purpose include but are not limited to anti-CD3 therapeutics which are one of the most promising approaches for increasing the number of CD4+ CD25− regulatory T cells in these patients.

XI. Pharmaceutical Formulations

In one embodiment, the therapeutic compositions of the present invention are incorporated into pharmaceutical compositions suitable for administration. Such compositions typically comprise the therapeutic compositions of the present invention and a pharmaceutically acceptable carrier. As used herein, a 'pharmaceutically acceptable carrier' is intended to include any and all solvents, dispersion media, coatings, antibacterial and antifungal agents, isotonic systems, and the like, compatible with the components of the therapeutic compositions of the present invention and pharmaceutical administration. The use of such media and agents for pharmaceutically active substances is well known in the art. Supplementary active compounds can also be incorporated into the composition.

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents, antioxidants such as ascorbic acid or sodium bisulfite, chelating agents such as ethylenediaminetetraacetic acid, buffers such as acetates, citrates or phosphates and agents for the adjustment of toxicity such as sodium chloride or dextrose. The pH can be adjusted with acids or bases, such as hydrochloric acid or sodium hydroxide. In many cases, it will be preferable to include isotonic agents, for example, sugars, polyalcohols such as mannitol, sorbitol, sodium chloride in the composition. The composition should be fluid to the extent that easy syringability exists. The proper fluidity can be maintained, for example, by the use of a coating such as lecithin, by the maintenance of the required particle size in the case dispersion and by use of surfactants. The composition must be stable under the conditions of manufacture and storage and must be preserved against the contaminating action of microorganisms such as bacteria and fungi. Prevention of the action of microorganisms can be achieved by various antibacterial and antifungal agents such as parabens, chlorobutanol, phenol, ascorbic acid, thimoseral, and the like. In all cases, the composition must be sterile. Sterile injectable solutions can be prepared by filtered sterilization. The preparation can be enclosed in ampoules, disposable syringes or multiple dose vials made of glass or plastic. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. For practical purposes it should be kept in mind that aluminum-adsorbed vaccines are frost sensitive and therefore not lyophilizable.

XII. Therapeutic Methods

In one embodiment, the present invention discloses therapeutic methods including information about suitable therapeutically effective doses of PS-containing liposomes (listed in section I), 'find me' signals (selected from those listed in section II), 'eat me' signals (selected from those listed in section III), mediators of macrophage-induced immune suppression (selected from those listed in section V), low molecular weight immune modulators (listed in section VI), and modes of administration for the induction of allergen or autoantigen tolerance using the compositions of the present invention.

Determination of a therapeutically effective dose is well within the capability of those skilled in the art. The therapeutically effective dose can be estimated initially in animal models, usually mice, rats, rabbits, dogs, pigs, or non-human primates. The animal model also can be used to determine the appropriate concentration range and route of administration. Such information can then be used to determine useful doses and routes for administration in humans.

XII.1. Therapeutic Effective Doses of PS-Containing Liposomes

PS-containing liposomes have been studied in a variety of animal models in the recent past. Results obtained from these studies provide useful information for the application of PS-containing liposomes in humans.

For example, using BALB/cAnN mice, the effect of subcutaneously (s.c.) administered PS-containing liposomes on immune responses upon subsequent injection of ovalbumin (OVA) or heyhole limpet hemocyanine (KLH) in complete Freund's adjuvant (CFA) has been investigated (Hoffman et al., 2005). In this study, PS-containing liposomes comprising a 30:30:40 molar ratio of PS to PC to cholesterol, were first injected s.c. in one flank of 6-8 weeks old BALB/cAnN mice (100 µl, corresponding to 0.5 mg of total lipid), followed after one hour by another s.c. injection of 150 µl of emulsion containing 50 µg of OVA or 150 µg of KLH in CFA in the same region. As evident from the data, subcutaneously administered PS-containing liposomes specifically inhibited responses to antigens. Numbers of total leukocytes and antigen-specific CD4+ T cells were reduced as well as the level of antigen-specific IgG in blood. There was also a decrease of draining lymph node tissue mass and the size of germinal centers in spleen and lymph nodes (Hoffman et al., 2005).

Using a rat model of acute myocardial infarction (MI) in another study, the effects of intravenously (i.v.) administered PS-containing liposomes on cardiac macrophages has been investigated (Harel-Adar et al., 2011). In this study, PS-containing liposomes comprising a 30:30:40 (1:1:1.33) molar ratio of PS to PC to cholesterol, were injected i.v. through the femoral vein of female Sprague-Dawley rats (150 µl of a 0.03 M saline solution of PS liposomes) 48 hours after MI induction. As evident from the data, i.v. administered PS-containing liposomes promoted angiogenesis, the preservation of small scars, and prevented ventricular dilatation and remodeling. Following uptake of PS-containing liposomes by macrophages, the cells secreted high levels of the anti-inflammatory cytokines TGF-β and IL-10 and upregulated the expression of the mannose receptor CD206, concomitant with downregulation of proinflammatory markers such as TNF-α and the surface marker CD86 (Harel-Adar et al., 2011).

In one embodiment, PS-containing liposomes are also used as carriers of encapsulated allergens/autoantigens or fragments thereof. Methods for encapsulation of proteins or fragments thereof to lipids are known to the person skilled in the art. Various formulations of liposomes containing encapsulated allergens (including allergen extracts), autoantigens or fragments thereof have been prepared and studied in a variety of animal models (e.g., Ishii et al., 2010; Meechan et al., 2012; Belogurov et al., 2013) and in clinical trials (e.g., Basomba et al., 2002). Furthermore, clinical trials have demonstrated that the safety of subcutaneously administered liposomes containing encapsulated allergen extracts is well tolerated (e.g., Galvain et al., 1999; Basomba et al., 2002).

In another embodiment, PS-containing liposomes are also used as carriers of surface-coupled allergens/autoantigens or fragments thereof. Methods for covalent coupling of proteins or fragments thereof to lipids are known to the person skilled in the art. For example, liposomes displaying surface-coupled protein antigen and glycan ligands of the inhibitory coreceptor CD22 have been prepared and applied recently to induce antigen-specific tolerance to protein antigens in mice (Macauley et al., 2013). In this study, protein antigens were coupled to phosphatidylethanolamine using the maleimide chemistry, and for sugar-lipid conjugation amine-derivatives of carbohydrates were coupled to NHS-derivatized lipid molecules.

XI.2. Therapeutic Effective Doses of Complement Inhibitors

Low molecular weight inhibitors of complement protein C3 and the receptors of C3a and c5a have been studied in a variety of animal models in the recent past. Results obtained from these studies provide useful information for the application of these inhibitors in humans. Furthermore, some of these inhibitors have entered clinical trials.

Inhibitors of Complement Protein C3

One preferred low molecular weight inhibitor targeting complement component C3 is the 13-residue cyclic peptide (H-I[CVVQDWGHHRC]T-NH$_2$) (termed compstatin) which is able to bind selectively to primate C3 and its C3b and C3c fragments, and to inhibit cleavage of C3 by C3 convertases of both the classical and the alternative pathway (Sahu et al., 1996; Ricklin and Lambris, 2008). compstatin exhibits exclusive specificity for primate C3 proteins and does not bind either to C3 proteins from lower mammalian species or to the structural C3 homologs C4 and C5 (Sahu et al., 2003). The concentration of compstatin causing 50% inhibition (IC$_{50}$) of the haemolytic activity (lysis of rabbit erythrocytes in serum by the alternative pathway) is 12 M for human sera and 10 M for sera from cynomolgus monkeys, whereas the IC$_{50}$ values for sera from mice, rats, and guinea pigs is >600 µM (Sahu et al., 2003).

In a recent animal study, administration of compstatin as a 10 mg/kg intravenous bolus injection followed by 60 µg/kg/min continuous infusion has been demonstrated to decrease the procoagulant response and to confer organ protection in a baboon model of *Escherichia coli* sepsis (Silasi-Mansat et al., 2010).

Recently, a phase I clinical study with the compstatin derivative POT-4 (Potentia Pharmaceuticals, Inc.) for the treatment of age-related macular degeneration has been completed successfully (Francois et al., 2009).

Inhibitors of C5a-C5aR Interactions

One preferred low molecular weight inhibitor targeting the C5a receptor (C5aR) is the peptidomimetic C5aR antagonist PMX53, a cyclic analog of the linear NMeFKPd-ChaWdR. PMX53 has a short half-life of 70 min and is susceptible to proteolytic cleavage (for a review, see Wagner and Frank, 2010), which is favorable for the method of the present invention.

The in vivo therapeutic efficacy of PMX53 has been demonstrated in several disease models (for reviews, see Qu et al, 2009; Monk et al., 2007). Relevant studies include antigen-induced monoarticular arthritis in rats (Woodruff et al., 2002), sepsis in mice (Huber-Lang et al., 2002), renal ischaemia/reperfusion injury in rats (Arumugam et al., 2003), hepatic ischaemia/reperfusion injury in rats (Arumugam et al., 2004), intestinal ischaemia/reperfusion injury in rats (Proctor et al., 2004), ruptured abdominal aortic aneurysm in rats (Harkin et al., 2004), inflammatory bowel disease in rats (Woodruff et al., 2005), lupus nephritis in mice (Bao et al., 2005b), 3-nitropropionic acid-induced Huntington's disease in rats (Woodruff et al., 2006), abdominal pain in mice and rats (Ting et al., 2008), and tumor growth in mice (Markiewski et al., 2008). The dosis of PMX53 in theses studies varied from 1-3 mg/kg/day p.o. in arthritis models, 1 mg/kg i.v and 10 mg/kg p.o. in reperfusion injury models, and up to 3 mg/kg i.v. in sepsis models (for a review, see Monk et al., 2007).

In humans, PMX53 has been shown to be safe and well tolerated in Phase 1 clinical studies for rheumatoid arthritis and psoriasis (Kohl, 2006).

Inhibitors of C3a-C3aR Interactions

One preferred low molecular weight inhibitor targeting the C3a receptor (C3aR) is the arginine derivative SB290157. SB290157 has a short in vivo half-life which is favorable for the method of the present invention.

The in vivo therapeutic efficacy of SB290157 has been demonstrated in several disease models including lung inflammation in guinea pigs (Ames et al., 2001), arthritis in rats (Ames et al., 2001), intestinal ischaemia/reperfusion injury in rats (Proctor et al., 2004), lupus nephritis in mice (Bao et al., 2005a), and allergic asthma in mice (Baelder et al., 2005). The dosis of SB290157 in theses studies varied from up to 30 mg/kg i.p. twice a day in the guinea pig neutrophilia model and in the adjuvant-induced arthritis model (Ames et al., 2001), and 0.1 to 1 mg/kg i.v. in the intestinal ischaemia/reperfusion injury model (Proctor et al., 2004). In the latter study, 10 mg/kg i.v. caused a rapid and transient hypertension. For treatment of allergic asthma in mice, 0.2 mg of SB290157 was administered intra nasal and 0.5 mg i.p. (Baelder et al., 2005).

XI.3. Therapeutic Effective Doses of Vitamin D3

Preferred vitamin D3 molecules include 25-OH-D3 (calcidiol), its biologically active metabolite 1,25-(OH)$_2$D3 (calcitriol), and vitamin D3 analog calcipotriol. These molecules have been studied in a variety of animal models and evaluated in clinical trials (for reviews, see Plum and DeLuca, 2010; Fletcher et al., 2012).

Current indications for clinical treatment with 25-OH-D3 or 1,25-(OH)$_2$D3 include renal osteodystrophy and osteoporosis. Toxicity occurs when serum levels of 25-OH-D3 rise to 500 ng/ml or above (Shephard and DeLuca, 1980). Based on experiments in the rat, serum levels of 25-OH-D3 should be kept below 250 ng/ml to avoid toxicity (Shephard and DeLuca, 1980).

The vitamin D3 analog calcipotriol has a very short half-life in circulation (Kragballe, 1995) and due to this property calcipotriol has been used clinically for more than 10 years for topical treatment of psoriasis without systemic toxicity (for a review, see Plum and DeLuca, 2010).

In animal studies, vitamin D molecules and analogs thereof have been used for the treatment of OVA-induced allergy in mice (Ghoreishi et al., 2009), OVA-induced allergic asthma in mice (Taher et al., 2008), insulin-dependent diabetes mellitus in NOD mice (Zella et al., 2003), Lyme arthritis and collagen-induced arthritis in mice (Cantorna et al., 1998), and experimental autoimmune encephalomyelitis (EAE) in mice (Branisteanu et al., 1995). In the allergy model, mice were treated on their shaved dorsal skin with 30 mg/day of calcipotriol ointment (50 µg/g) (Donovex, Leo Pharma) for three days followed by transcutaneous immunization with OVA in the presence of CpG adjuvant. This treatment abolished antigen-specific CD8+ T cell priming and induced CD4+CD5+ Tregs, thereby promoting antigen-specific tolerance (Ghoreishi et al., 2009). In the allergic asthma mode, OVA-sensitized mice were subjected to allergen-specific immunotherapy by three s.c. injections of 100 µg OVA in the presence of 10 ng 1,25-(OH)$_2$D3. This treatment significantly inhibited airway hyper-responsiveness and caused a significant reduction of serum OVA-specific IgE levels (Taher et al., 2008). In the murine model of type 1 diabetes, a diet containing 50 ng 1,25-(OH)$_2$D3/mouse/day was administered three times/week. This treatment prevented diabetes onset in NOD mice as of 200 days (Zella et al., 2003). In the arthritis models, mice received a daily diet supplemented with 20 ng 1,25-(OH)$_2$D3/mouse/day. This dose was found to be effective in inhibiting the progression of arthritis without producing hypercalcemia (Cantorna et al., 1998). In the EAE model, i.p. injection of 5 µg of 1,25-(OH)$_2$D3/kg body weight every 2 days prevented the appearance of paralysis in 70% of the treated mice (Branisteanu et al., 1995).

Evaluation of vitamin D supplementation in clinical trials support some observations made in animal models. It should be noted, however, that only low doses of vitamin D3 or analogs thereof were administered to avoid adverse side effects such as hypercalcemia.

A recent prospective randomized, double-blind study including 48 children from 5 to 18 years of age with newly diagnosed asthma (only sensitive to house dust mites) has demonstrated that after six months of treatment with the glucocorticoid budesonide (800 µg/d, administered as dry powder) and cholecalciferol (500 IU) a significantly lower number of children experienced asthma exacerbation (17%) as compared to the group receiving only glucocorticoids (46%) (Majak et al., 2011).

For the prevention of type 1 diabetes, vitamin D supplementation in infants with 10 g/day (400 IU/d) does not appear to be sufficient, but doses of 50 g/day (2000 IU/d) and higher may have a strong protective effect (for a review, see Harris, 2005). A prospective study of vitamin D supplementation in infants and type 1 diabetes including 12,055 pregnant women in Northern Finland showed that regular vitamin D supplements during infancy at doses of over 50 µg/day (2000 IU/d) reduced the relative risk of type 1 diabetes over the subsequent 30 years to 0.14, and at doses of exactly 50 µg/day to 0.22 (Hypponen et al., 2001). Current U.S. recommendations are in the range of 5-25 µg/day (200-1000 IU/d).

In one open label study, 19 patients with rheumatoid arthritis on methotrexate therapy were treated with 2 g/day of alfacalcidiol (1(OH)D3) for a period of 3 months. After three months of therapy, 89% of patients experienced an improvement of disease activity, with 45% (9/19) going into remission (Andjelkovic et al., 1999).

Until 2012 seven vitamin D intervention studies have been performed in patients with multiple sclerosis, six of them being performed with inactive 25-OH-D3 and one with active 1,25-(OH)$_2$D3 (for a review, see Fletcher et al., 2012). Some of these explorative trials did show a trend to improvement, but significant clinical effects were not reported. For example, after oral administration of 4,000-40,000 IU/day of 25-OH-D3 for 28 weeks, a significant decrease in the number of new lesions as assessed by magnetic resonance imaging (MRI) was observed, but disease progression and relapse activity were not affected (Kimball et al., 2007). However, despite the limited clinical efficacy of published vitamin D intervention studies, the studies indicate that systemic vitamin D therapy is well tolerated since the trials (most of which administered doses of 1,000 to 40,000 IU/day of 25-OH-D3) recorded no adverse effects (for a review, see Fletcher et al., 2012). Only the study performed with active 1,25-(OH)$_2$D3 reported hypercalcemia in those individuals who did not adhere to the recommended dietary restriction of 2.5 µg/day (Wingerchuk et al., 2005).

XI.4. Therapeutic Effective Doses of IL-4/IL-13 Inhibitors

Preferred inhibitors of IL-4/IL-13-mediated effects include the human IL-4 double mutant R121D/Y124D (Grunewald et al., 1998; Tony et al., 1994). This double mutant has been evaluated in clinical trials (Wenzel et al., 2007). For animal experiments, an analogous murine double mutant (Q116D/Y119D) has been developed capable of inhibiting IL-4/IL-13-mediated effects in mice.

In a murine model of allergy, the analogous double mutant (Q116D/Y119D) has been administered 2 hours pre- and post-OVA immunization as a 50 µg dose each. Thereafter, treatment was continued from day 1 to 8 with 30 µg double mutant Q116D/Y119D per injection twice a day. This treatment completely abrogated humoral immune responses to OVA and development of allergic symptoms (Grunewald et al., 1998).

In a murine model of OVA-induced allergic airway inflammation, immunotherapeutic treatment (SIT) of the mice was performed by intranasal administration of 10 µg of the double mutant (Q116D/Y119D) together with increasing amounts of OVA (1 µg-1 mg) every fourth day over a 3-week period. However, mice treated with the IL-4/IL-13 inhibitor during SIT did not produce significantly different results as compared to those treated with increasing amounts of OVA only (Gogishvili et al., 2006).

XI.5. Therapeutic Effective Doses of TNFR1-Inhibitors

Preferred low molecular weight inhibitors of TNFR1-mediated functions include N-acetyl-L-cysteine (NAC) and other glutathione (GSH) prodrugs, salicylates, and TNFR1-specific antisense oligo-nucleotides. Preferred moderate molecular weight inhibitors of TNFR1-mediated functions include TNFR1-selective antagonistic TNF mutants and dominant-negative sTNF mutants, which leave the mTNF-TNFR1 and mTNF-TNFR2 interactions intact (for a review, see Van Hauwermeiren et al., 2011). Such molecules have been studied in varies animal models and some of them have been evaluated in clinical studies.

N-Acetyl-L-Cysteine (NAC) and Other Glutathione Prodrugs

S-Methylglutathione (GSM; MW 321.35) is a glutathione donor and NAC (MW 163.20) a glutathione precursor. NAC is readily deacetylated in the body to form cysteine which efficiently supports glutathione (GSH) synthesis.

In cultures of peripheral blood T cells, 10 mM NAC proved to be an effective enhancer of T cell function and enhancer of growth (Eylar et al., 1993). Cytotoxicity studies with resting T cells from seven donors over a 3 day period in the absence and presence of NAC ranging from 1 mM (163.2 µg/ml) to 20 mM (3.26 mg/ml) revealed that NAC is nontoxic even at 20 mM (Eylar et al., 1993).

In isolated rat cardiomyocytes, exogenously added S-methylglutathione (GSM) has been demonstrated to reproduce the effects of in vivo NAC treatment (Cailleret et al., 2004). After preincubation for 2-3 hours in a medium containing 50 M GSM, cardiomyocytes isolated from control rats were protected against the deleterious effects of TNF-alpha on contraction to the same extent as cardiomyocytes isolated from rats treated by two i.p. injections of 100 mg NAC, 48 and 24 hours before anesthesia. Cardiomyocytes isolated from control rats were not protected by exogenously added NAC under these experimental conditions, pointing to the necessity of a long-term preincubation (at least 2-3 days) in case of NAC administration and a short-term pre-incubation (at least 2-3 hours) in case of GSM administration.

Mice sensitized to ovalbumin have been treated for 8 days with drinking water containing 0.5 g/liter up to 2 g/liter NAC adjusted to pH 7.5 and changed every 2 days (Jeannine et al., 1995). Using 1.0 g/liter NAC, both ovalbumin-specific IgE and IgG1 (the murine isotype equivalent to human IgG4) responses were decreased by more than 70%. Even at 0.5 g/liter NAC the decrease of ovalbumin-specific IgE and IgG1 was still in the range of 30%. On the basis of the volume of water drunk in one day, the quantity of NAC swallowed by a mouse could be estimated at 50 mg/kg/day, comparable to 9 mg/kg per day given in humans as a mucolytic or 300 mg/kg per day as an antidote against acetaminophen-induced hepatotoxicity (Jeannine et al., 1995). This suggests that NAC acts in the range of doses that are already used in human therapeutics.

In patients, NAC has been administered orally at high doses in clinical studies for the treatment of idiopathic pulmonary fibrosis (Demedts et al., 2005) and cystic fibrosis (Tirouvanziam et al., 2006). Evaluation of NAC for the treatment of idiopathic pulmonary fibrosis was performed over one year in a double-blind, randomized, placebo-controlled multicenter study with a total of 182 patients. In this study, NAC was administered at a total oral dose of 1800 mg/day in addition to the standard therapy with prednisone and azathioprine. Although this NAC dose is three to nine times the usual approved dose of NAC when it is administered as an antioxidant and mucolytic agent in chronic obstructive pulmonary disease, the NAC and placebo groups had similar overall rates of side effects. The primary end points including vital capacity proved to be better in the group receiving NAC in addition to the standard therapy (Demedts et al., 2005).

For the treatment of cystic fibrosis, high NAC doses in excess of 1800 mg/day (600 mg to 1000 mg NAC three times daily) were administered orally for 4 weeks in a phase 1 study with 18 cystic fibrosis patients (Tirouvanziam et al., 2006). The high doses proved to be safe and effective in augmenting the GSH level in blood neutrophils and decreasing the airway neutrophil count and elastase activity.

The data of both studies confirm the proven safety record of long-term use of high doses of NAC (Kelly, 1998).

Salicylates

The various inhibitory effects of acetylsalicylic acid (ASA; MW 180.2) and related salicylates (e.g., sodium salicylate; SA; MW 160.11) are concentration dependent. A 50% inhibition by ASA requires a concentration of approx. $2 \times 10^{-6}$ M for COX-1, approx. $3 \times 10^{-4}$ M for COX-2, approx. $1 \times 10^{-3}$ M for IL-4 gene transcription, and approx. $3 \times 10^{-3}$ M for NF-kappa B translocation (Cianferoni et al., 2001). Selective inhibition of TNFR1-mediated activation of NF-kappa B requires even higher doses of salicylates in the range of $1-2 \times 10^{-2}$ M (Thommesen and Laegreid, 2005).

The therapeutic range for ASA and SA has been restricted to $0.8-1.7 \times 10^{-3}$ M, corresponding to a serum salicylate concentration of 150-300 mg/liter. Restriction of the therapeutic range is necessary to avoid salicylate-related toxicity such as tinnitus. It should be mentioned, however, that tinnitus may occur also occasionally at levels as low as 95 mg/liter (Furst et al., 1987).

Salicylate kinetics are complex, involving 2 capacity limited and 3 first order processes (Furst et al., 1987). Capacity limited processes mean that the enzyme(s) acting to metabolize a drug become saturated and are working at their maximum capacity, even at relatively low drug doses. Therefore, small increases in dose can result in a disproportionate increase in serum levels. First order processes are those which metabolize increasing amounts of drug as more drug is presented to them. Therefore, an increase in dose results in a directly proportional increase in serum concentration. Further complications of salicylate kinetics include the facts that protein binding is not linear, that urinary excretion of un-metabolized salicylate is urine pH dependent, and that there is inherent genetic variability.

Using choline magnesium trisalicylate (CMS) for the treatment of patients with rheumatoid arthritis (RA), a strategy for reaching therapeutic salicylate levels has been developed (Furst et al., 1987). Despite the complex salicylate kinetics, the authors used a simplified weight adjusted dose of 45 mg CMS/kg/day as an initial dose. After one to two weeks of 45 mg CMS/kg/day in two divided doses, 51 of 71 patients with RA had steady state serum salicylate levels between 150 and 300 mg/liter (mean value: 213±10 mg/L). Seventeen patients required dose adjustment using the formula: dosing rate=total clearance×concentration. Since all salicylate preparations are metabolized similarly once they are adsorbed and broken down to the parent salicylate molecule, the results of this study apply to all salicylates.

TNFR1-Specific Antisense Oligonucleotides

In mice, TNR1-specific antisense oligonucleotides have been administered as 2'-O-(2-methoxy)ethyl-modified antisense oligonucleotides (ASO). After i.p. injection of 25 mg/kg ASO every other day for a total of four times, mice were protected against subsequent radiation-induced liver damage (Huang et al., 2006).

In a preferred embodiment of the present invention, non-modified TNR1-specific antisense oligonucleotides are complexed with cationic liposomes to enhance cellular uptake and protect the oligonucleotides against enzymatic degradation in serum.

In one specific embodiment of the present invention, ultradeformable cationic liposomes (UCL) containing sodium cholate in addition to DOTAP (Kim et al., 2004) are used for complexing non-modified TNR1-specific antisense oligonucleotides. Sodium cholate is an edge activator and responsible for rendering flexibility in liposomes. The addition of sodium cholate provides an additional advantage in that instead of toxic organic solvents such as chloroform phosphate-buffered saline (PBS) can be used for the preparation of UCLs. PBS is not capable of dissolving DOTAP, but as soon as sodium cholate is added at a ratio of 1:6 (w/w) to the mixture of DOTAP and PBS (10 mg DOTAB/ml PBS), DOTAB is dissolved. Furthermore, sodium cholate inhibits the tendency of DOTAP for aggregation. The average particle size of this formulation is approximately 80 nm. Assessment of the in vitro transfection efficiency of plasmid DNA revealed an optimal ratio of 1:14 DNA/UCL (Kim et al., 2004). Recently, such liposomes have been used for transdermal delivery of non-modified IL-13-specific antisense oligonucleotides (IL-13 ASO) for the treatment of mice with atopic dermatitis (Kim et al., 2009). At a ratio of 6:1 (IL-13 ASO/UCL), maximum inhibition of IL-13 secretion was observed (Kim et al., 2004).

In a preferred specific embodiment of the present invention, multilammelar vesicles (MHLVs) containing the cationic lipid 1,2-dioleoyl-3-trimethylammonium-propane (DOTAP) are used for complexing non-modified TNR1-specific antisense oligonucleotides. Such MLV lipoplexes have been shown to mediate efficient cellular association and uptake (Ross et al., 1998). The cellular uptake is believed to occur mainly through endocytosis with escape of the DNA into the cytoplasm of the cell by fusion of the liposomes with, or rupture of the endosomal membrane. In the presence of serum, multilammelar vesicles (>300 nm) are more efficient vectors for DNA transfer than small unilammelar vesicles (SUVs; <300 nm), which interact to higher extent with serum proteins (Ross et al., 1998). Serum proteins are thought to destabilize the bilayer membranes of liposomes, which may alter the lipoplex and prevent its ability to associate with cells, thus decreasing the uptake of DNA. A number of variables have been identified to influence the effectiveness of lipoplexes as vector including the charge ratio of cationic lipid to DNA. Using DOTAP-containing MLVs, optimal charge ratios of cationic lipid to DNA are below and up to about 1:1 (Ross et al., 1998). For example, for the preparation of lipoplexes with a ratio of 1:2 (cationic lipid to DNA) according to the method of Ross et al. (1998), 12 µg of DNA is added to 300 µl of a DOTAP-containing MLV suspension with a concentration of 0.133 mole/ml.

In another preferred embodiment of the present invention, non-modified TNR1-specific antisense oligonucleotides complexed with cationic liposomes are embedded into hydrogels. Preferred hydrogels include those listed in section II.

Dominant-Negative sTNF Mutants

Several sTNF-alpha variants have been designed by exchange of one or two amino acid residues, which are capable of sequestering native TNF-alpha homotrimers from TNF receptors by formation of inactive native:variant heterotrimers (Steed et al., 2003). At concentrations as low as two-fold that of native TNF-alpha, variants A145R/Y87H and A145R/I97T attenuated TNF-induced caspase activity by 50% and at 20-fold excess, activity was reduced to baseline. At 10-fold excess over native TNF-alpha, variant A145R/Y87H blocked TNF-induced translocation of the NF-kappa B p-65-RelA subunit in HeLa cells. Several dominant-negative sTNF-alpha variants neutralize TNF-induced caspase and NF-kappa B-mediated transcriptional activity over a wide range of native TNF-alpha concentrations, including the clinically relevant range of 100 to 200 μg/ml found in the synovial fluid of rheumatoid arthritis patients (Steed et al., 2003).

Furthermore, variant A145R/Y87H proved to be non-toxic. Dosed as high as 30 mg/kg of mouse body weight (along with 30 μg/kg native TNF-alpha), A145R/Y87H did not induce mortality or hepatotoxicity. In a murine model of collagen-induced arthritis, variant A145R/Y87H reduced joint swelling when dosed once daily at 2 mg/kg subcutaneously with an intravenous loading dose of 2 mg/kg on the first treatment day (Steed et al., 2003).

TNFR1-Specific TNF Mutants

Useful TNFR1-specific sTNF-alpha mutants include but are not limited to R1antTNF containing mutations A84S, V85T, S86T, Y87H, Q88N, and T89Q (Shibata et al., 2008). R1antTNF neutralizes TNFR1-mediated responses without affecting TNFR2-mediated bioactivity. Like wild-type TNF-alpha, R1antTNF has a very short half-life of approximately 10 min in plasma of mice. By site-specific PEGylation of R1antTNF at its N-terminus, the plasma half-life of R1antTNF could be increased significantly (Shibata et al., 2009).

Administration of R1antTNF or PEG-R1antTNF at 1 μg or 3 μg/mouse twice a day for 3 weeks in mice with collagen-induced arthritis (the treatment was started 2 days after the second immunization) significantly decreased the severity of arthritis (Shibata et al., 2009). Only R1antTNF at 1 μg/mouse had no therapeutic effect, most likely due to the short plasma half-life of R1antTNF, since 1 μg/mouse of PEG-R1antTNF was effective.

XI.6. General Considerations

Dosage regimens may be adjusted to provide the optimum therapeutic response. The quantity of the polymer-embedded components depends on the release kinetics of the biodegradable thermo-gelling polymer and is adjusted to a level that guarantees the continuous release of therapeutically effective doses over a period of 3 to 5 days. The quantity of embedded components will vary according to factors such as the weight and the age of the individual, and the ability of the composition to induce an effective immune response in the individual.

In summary, these data provide useful guidelines for the determination of a therapeutically effective dose for those skilled in the art.

XI.7. Therapeutic Applications of Suitable Compositions

In one embodiment of the present invention, methods for local enhancement of the suppressive functions of regulatory T cells at the site of allergen or auto-antigen presentation as adjuvant therapy prior and during allergen- or autoantigen-specific immunotherapy in patients with allergy, allergic asthma or autoimmune diseases are disclosed using suitable compositions of the present invention.

In a specific embodiment of the present invention, a suitable combination of PS-containing liposomes (optionally containing one or more mediators of macrophage-induced immune suppression and optionally displaying one or more tolerance supporting liposomal surface ligands), optionally one or more ‘find me’ signals, optionally one or more ‘eat me’ signals, and individual combinations of Treg-modulating therapeutics capable of inhibiting unwanted local immune reactions at the site of allergen presentation is administered subcutaneously or intradermally in a depot-mediating matrix for sustained delivery of the components. After a period of time, sufficient for exerting their biological effects, one or more allergens or auto-antigens, optionally in the presence of alum or another adjuvant, are injected at the same site. Dependent on the properties of the therapeutics embedded in the depot-mediating matrix, additional injection(s) of embedded therapeutics at the site of allergen presentation may be performed to support the local enhancement of the suppressive functions of regulatory T cells within the period of allergen or auto-antigen presentation to T cells.

In another specific embodiment of the present invention, a suitable combination of one or more allergens or auto-antigens (optionally in the presence of alum or another adjuvant), PS-containing liposomes (optionally containing one or more mediators of macrophage-induced immune suppression and optionally displaying one or more tolerance supporting liposomal surface ligands), optionally one or more ‘find me’ signals, optionally one or more ‘eat me’ signals, and individual combinations of Treg-modulating therapeutics capable of inhibiting unwanted local immune reactions at the site of allergen presentation, all of them embedded in a depot-mediating matrix for sustained delivery, are administered subcutaneously or intradermally. Dependent on the properties of the therapeutics embedded in the depot-mediating matrix, additional injection(s) of embedded therapeutics at the site of allergen or auto-antigen presentation may be performed to support local enhancement of the suppressive functions of regulatory T cells within the period of allergen or auto-antigen presentation to T cells.

In another specific embodiment of the present invention, a suitable combination of one or more allergens or auto-antigens encapsulated in PS-containing liposomes (optionally containing also one or more mediators of macrophage-induced immune suppression and optionally displaying one or more tolerance supporting liposomal surface ligands), optionally one or more ‘find me’ signals, optionally one or more ‘eat me’ signals, and individual combinations of Treg-modulating therapeutics capable of inhibiting unwanted local immune reactions at the site of allergen presentation, all of them embedded in a depot-mediating matrix for sustained delivery, are administered subcutaneously or intradermally. Dependent on the properties of the therapeutics embedded in the depot-mediating matrix, additional injection(s) of embedded therapeutics at the site of allergen or auto-antigen presentation may be performed to support local enhancement of the suppressive functions of regulatory T cells within the period of allergen or auto-antigen presentation to T cells XI.8. Modes of Administration of Therapeutic Compositions Routes of administration of the compositions of the present invention by injection or by implantation include but are not limited to subcutaneous, intradermal, intramuscular, nasal, transbucal, transmucosal, sublingual, rectal, vaginal, intraocular, or topical administration. Preferred examples of routes of administration of the compositions of the present invention include but are not limited to intradermal, subcutaneous, and intramuscular administration.

For mucosal immunization, the physicochemical characteristics of the administered components and the delivery vehicle have to be adjusted to stimulate their uptake through the various mucosal routes. For example, alum salts are ineffective when administered by the oral or nasal route. In contrast, cationic chitosan derivatives are of special interest in nasal delivery because of their excellent biocompatibility and mucoadhesive nature (Hagenaars et al., 2010). For example, a thermal-sensitive hydrogel which was formulated as intranasal vaccine with N[(2-hydroxy-3-trimethylammonium)propyl] chitosan chloride (HTCC) and α,β-glycerophosphate, was shown to significantly prolong the antigen residence time in the nasal cavity and to enhance the transepithelial transport via the paracellular routes (Wu et al., 2012).

EXAMPLES

The following examples are intended to illustrate but not limit the present invention.

Example 1: Thermo-Gelling PLGA-PEG-PLGA Hydrogels

This example describes the synthesis and cauterization of thermogelling PLGA-PEG-PLGA hydrogels.

1.1. Synthesis of Thermogelling PLGA-PEG-PLGA Hydrogels

The biodegradable triblock polymer described in this example has a PLG/PEG weight ratio of 2.3 (70/30), and a lactide/glycolide molar ratio of approx. 15/1. Synthesis of the triblock copolymer is performed according to published protocols (Qiao et al., 2005).

1.1.1. Copolymer Synthesis

Polyethylene glycol (PEG 1000) was purchased from Fluka, poly(DL-lactide) from Sigma, glycolide (1,4-Dioxane-2,5-dione) from Sigma, and stannous 2-ethylhexanoate from Aldrich.

A total of 25 g of DL-lactide, glycolide and PEG are used for polymerization (16.6 g DL-lactide, 0.9 g glycolide, 7.5 g PEG 1000). Under nitrogen atmosphere, PEG 1000 is dried under vacuum and stirring at 120° C. for 2 h in a vigorously dried Erlenmeyer reaction flask. Then the reaction flask is filled with dry argon. DL-lactide and glycolide monomers are added under stirring followed by the addition of Stannous 2-ethylhexanoate (0.2% w/w). Then the tube is sealed under argon. The sealed flask was immersed and kept in an oil bath thermostated at 150° C. After 8 h the flask was cooled to room temperature, and the product was dissolved in cold water. After completely dissolved, the copolymer solution is heated to 80° C. to precipitate the copolymer and to remove the water-soluble low molecular weight copolymers and unreacted monomers. The supernatant is decanted, the precipitated copolymer is again dissolved in cold water followed by heating to induce precipitation. This process of dissolution followed by precipitation is repeated three times. Finally, the copolymer is dried under vacuum at room temperature until constant weight.

1.1.2. Molecular Weight Determination

The molecular weight of the copolymer is determined by gel permeation chromatography using polystyrene standards as described by Qiao et al. (2005).

1.1.3. Measurement of Gelation Temperature

The gelation temperature is determined as described by Qiao et al. (2005). A 2 ml transparent vial is filled with 200 µl water solution of the copolymer (20% w/w and 25% w/w), is placed in a water bath. The solution is heated in 1° C. steps beginning at 26° C. in a thermomixing device (Eppendorf). At each temperature step the gelation is checked by careful inversion of the tube. When the solution is not free-flowing, gelation of the solution occurred, the temperature read from the thermometer is determined as gelation temperature.

1.2. In Vitro Degradation of PLGA-PEG-PLGA Hydrogels

The in vitro degradation behavior of the copolymer of Example 1.1 is evaluated by the mass loss and/or the molecular weight reduction with time upon incubation in phosphate-buffered saline.

Samples (0.5 ml) are incubated in phosphate-buffered saline pH 7.4 at 37° C. under mild agitation in a water bath. The solid residues are removed from the incubation medium at scheduled time intervals and lyophilized. The samples are weighted and the weight loss is calculated. For determination of the molecular weight reduction, the solid residues are solved in cold water and analyzed by gel permeation chromatography using polystyrene standards as described by Qiao et al. (2005).

1.3. In Vivo Gelation of PLGA-PEG-PLGA Hydrogels

To test the in vivo gel formation behavior of PLGA-PEG-PLGA hydrogels of Example 1.1., the hydrogel is injected subcutaneously into mice.

240 µl of a 18% PLGA-PEG-PLGA blockpolymer solution in water is mixed with 30 µl of 10× PBS (pH 7.4) buffer and 30 µl of 30 mM morpholino ethanesulfonic acid (MES) buffered solution (pH 6.0) at room temperature.

The gel sol solution is injected subcutaneously into hairless mouse (strain SKH1), euthanized by cervical dislocation and kept in 37° C. pad, at two sites in amounts of 50 and 100 µl (see FIG. 1A).

After 2 hours the gels are analyzed in the mouse by magnetic resonance imaging (MRI), using a Bruker BioSpec 9421 instrument. The position and gelled status of the hydrogel is further confirmed by chirurgical examination of the implanted hydrogel (see FIGS. 1B and 1C).

1.4. Biodegradation of PLGA-PEG-PLGA Hydrogels

To test the in vivo degradation characteristics of PLGA-PEG-PLGA hydrogels of Example 1.1., the hydrogel is injected subcutaneously into mice that have been anesthetized with ethyl ether. The resulting gel implants are then allowed to develop in vivo over the experimental period. At each of the post-injection sampling points, the mice are sacrificed, the gel implants are removed from the subcutaneous injection site, and the removed gel implants are analyzed as described in Example 1.2.

Example 2: PLGA-PEG-PLGA/PS-Liposome Composites

This example describes the synthesis and cauterization of thermogelling PLGA-PEG-PLGA hydrogels containing phosphatidylserine (PS)-liposomes.

2.1. Synthesis of Thermogelling PLGA-PEG-PLGA Hydrogels

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

2.2. Synthesis of PS-Liposomes

This example describes the synthesis of unilamellar PS-liposomes from a lipid mixture of phosphatidyldserine (PS), either 1,2-Dipalmitoyl-sn-glycero-3-phospho-L-serine sodium salt (Sigma-Aldrich), 1-palmitoyl-2-oleoyl-sn-3-glycerophospho-L-serine (POP-L-S) or bovine brain phosphatidyldserin (Avanti Polar Lipids), phosphatidylcholine (PC), either 1,2-Dipalmitoyl-sn-glycero-3-phosphocholine (Sigma-Aldrich), 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 22.7 mg), mol PC (approx. 22.0 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) is added and multilamellar vesicles are generated by intense vortex dispersion. For the preparation of unilamellar vesicles, the multilamellar preparation is extruded 10 times through a 1 µm pore polycarbonate membrane (Nucleopore, USA). PS-liposomes with a particle size of approx. 1 µm are suitable for efficient uptake by macrophages (Harel-Adar et al., 2011). The liposome suspension is centrifuged at 5000×g for 5 minutes and the supernatant is discarded by pipetting and replaced by the same volume of fresh buffer and vortexed to resuspend the liposomes. The final liposomal suspension contains approx. 66.6 µmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS.

2.3. Gelation Characteristics of Hydrogel/PS-Liposome Composites

The gelation temperature of hydrogel/PS-liposome composites of Example 2.3. is determined as described by Qiao et al. (2005).

Transparent vials are filled with 200 µl water containing different concentrations of the copolymer of Example 2.1. (22.5% w/w, and 30% w/w), cooled to 4° C. and mixed with 100 µl PBS containing liposomes of Example 2.2 (6.7 µmol lipid) or 100 µl PBS containing no liposomes. The final concentrations of the copolymer are 15% w/w and 20% w/w containing liposomes at a concentration of 22.3 µmol lipid/ml (13.1 mg/ml). The vials are placed in a water bath and each solution is heated in 1° C. steps beginning at 26° C. in a thermomixing device (Eppendorf). At each temperature step the gelation is checked by careful inversion of the tube. When the solution is not free-flowing, gelation of the solution occurred, the temperature read from the thermometer is determined as gelation temperature.

2.4. In Vitro Degradation of Hydrogel/PS-Liposome Composites

The in vitro degradation behavior of hydrogel/PS-liposome composites of Example 2.3. is evaluated by the mass loss and/or the molecular weight reduction with time upon incubation in phosphate-buffered saline.

Samples (0.2 ml) are incubated in phosphate-buffered saline pH 7.4 at 37° C. under mild agitation in a water bath. The solid residues are removed from the incubation medium at scheduled time intervals and lyophilized. The samples are weighted and the weight loss is calculated. For determination of the molecular weight reduction, the solid residues are solved in cold water and analyzed by gel permeation chromatography using polystyrene standards as described by Qiao et al. (2005).

Example 3: PLGA-PEG-PLGA/PS-MAN-Liposome Composites

This example describes the synthesis and cauterization of thermogelling PLGA-PEG-PLGA hydrogels containing liposomes with phosphatidylserine (PS) and mannose (MAN) or oligomannose (e.g. Man3) on their surface.

3.1. Synthesis of Thermogelling PLGA-PEG-PLGA Hydrogels

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

3.2. Conjugation of Mannose Residues to Lipid Molecules

This example describes the synthesis of three types of mannosylated lipids including conjugates of mannotriose and phosphatidylethanolamine ($Man_3$-PE), conjugates of mannose and N-glutaryl-phosphatidylethanolamine (Man-NGPE), and conjugates of mannose and cholesterol via a butyl spacer (Man-C4-Chol).

3.2.1. Conjugation of Mannotriose to Phosphatidylethanolamine

A mixture of 5 mg of mannotriose (Man3; Manα1-6(Manα1-3)Man) (Sigma-Aldrich; MW 504.4) in 0.6 ml of distilled water, 9.4 ml of dipalmitoylphosphatidylethanolamine (DPPE; MW 691.9) dissolved in a mixture of chloroform/methanol (1:1 v/v) to a concentration of 5 mg/ml, and 1 ml of sodium cyanoborohydride ($NaBH_3CN$) dissolved in methanol to a concentration of 10 mg/ml, is sonicated in a sonic bath (10 min) and then incubated at 60° C. for 16 hours (with continuous stirring) as described in EP0677295B1. After removal of the solvent under a stream of $N_2$ the residues are suspended in chloroform/methanol/water (4:50:50 v/v/v) and applied on a C18 reverse phase column equilibrated with the same solvent. After washing with 50 ml of this solvent, the lipids are eluted from the column with 30 ml chloroform/methanol/water (10:10:3 v/v/v). Purification of the neoglycolipid is done by HPLC on a silica column with a linear gradient of chloroform/methanol/water (65:30:5 v/v/v) and chloroform/methanol/water (50:55:18 v/v/v) as described (Ikehara et al., 2006). The purified neoglycolipid is quantified by determination of phosphate and hexose.

3.2.2. Conjugation of Mannose to N-Glutaryl-PE (Man-NGPE)

Several studies have demonstrated that a spacer which extends the mannose residue at least 3-4 carbons away from the surface of the liposome enhances liposome-ligand cellsurface-receptor binding. The N-glutaryl-phosphatidylethanolamine (NGPE) with its 4 carbon equivalent spacer arm, commonly used in its unsaturated (e.g. DOPE) and monounsaturated form (e.g. POPE), provides sufficient extension.

Following the method of U.S. Pat. No. 6,045,821, N-glutaryl-phosphatidyl-ethanolamine (0.1 mmol) (Avanti Polar Lipids, USA) in 5 ml of chloroform is treated with N-hydroxysuccinimide (0.2 mmol) and dicyclohexylcarbodiimide (20 mmol). The reaction mixture is stirred at ambient temperature overnight and filtered to remove the urea. p-Aminophenyl-α-D-mannopyranoside (0.15 mmol) (Sigma-Aldrich) in 1 ml of methanol is added and the reaction is stirred at ambient temperature for 6 hours, and then evaporated to dryness. The residue is dissolved in 10 ml of chloroform and dialysed against sodium acetate buffer (1 L, 50 mM, pH 5.5, 12 hours), Tris buffer (1 L, pH 8, 50 mM, 5 hours), and deionized water (1 L, 5 hours). A small amount of precipitate formed in the chloroform layer is dissolved by the addition of methanol. The solution is dried and evaporated to yield the product as a white, waxy solid.

Alternatively, mannosyl residues can be coupled to phospatidylethanolamine (PE) using a polyethylene glycol spacer (Engel et al., 2003).

3.2.3. Conjugation of Mannose to Cholesterol (Man-C4-Chol)

Following the method of Kawakami et al. (2000), cholesteryl chloroformate is first reacted with N-(4-aminobutyl) carbamic acid tert-butyl ester. After deprotection of the amino group with trifluoroacetic acid, N-(4-aminobutyl)-(cholesten-5-yloxyl) formamide is obtained. The solvents are then evaporated under vacuum and the resulting syrup is dissolved in hexane. In a second step, 2-imino-2-methoxy-ethyl-1-thiomannoside (IME-thiomannoside) is prepared according to method of Lee et al. (1976) by reaction of cyanomethyl-1-thiomannoside with methoxide methanolic solution. After vacuum drying, the resulting syrup is dissolved in pyridine containing triethylamine. Finally, N-(4-aminobutyl)-(cholesten-5-yloxyl) formamide and IME-thiomannoside are reacted to produce cholesten-5-yloxy-(N-(4-((1-imino-2-β-thiomannosyl-ethyl)amino)butyl)formamide (termed Man-C4-Chol), which is vacuum dried, dialyzed (12 kDa cut-off), and lyophilized.

3.3. Synthesis of Liposomes with Surface-Coupled PS and $MAN_3$

This example describes the preparation of liposomes containing phosphatidyerine (PS) and mannotriose ($Man_3$)-phosphatidyl-ethanolamine conjugates (Man3-PE) at a ratio of 20:10:30:40 PS to $Man_3$-PE to PC to CH.

A chloroform/methanol (2:1, v/v) solution containing 20 µmol 1-palmitoyl-2-oleoyl-sn-3-glycerophospho-L-serine (POP-L-S) (Avanti Polar Lipids; approx. 16.3 mg), 10 µmol Man3-dipalmitoyl-PE of Example 3.2.1. (Man3-DPPE; approx. 11.9 mg), 30 µmol 1-palmitoyl-2-oleoyl-sn-3-glycerophosphocholine (POPC) (Avanti Polar Lipids; approx. 22.8 mg) and 40 µmol cholesterol (CH) (Avanti Polar Lipids; approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) is added and multilamellar vesicles are generated by intense vortex dispersion. For the preparation of unilamellar vesicles, the multilamellar preparation is extruded 10 times through a 1 µm pore polycarbonate membrane (Nucleopore, USA). The final liposomal suspension contains approx. 66.6 µmol (44.3 mg) of lipid/ 1.0 ml.

The degree of PS exposure on liposomes is assessed by binding of FITC-annexin V to surface-exposed PS and analysis by FACS. The presence of mannotriose on the liposomal surface is confirmed by their agglutination by concanavalin A (Fukasawa et al., 1998).

3.4. Gelation Characteristics of Hydrogel/PS-$MAN_3$-Liposome Composites

The gelation temperature of hydrogel/PS-Man3-liposome composites is determined as described by Qiao et al. (2005).

Transparent vials are filled with 200 µl water containing different concentrations of the copolymer of Example 3.1. (22.5% w/w, and 30% w/w), cooled to 4° C. and mixed with 100 µl PBS-Man3-liposomes of Example 3.3. (6.7 µmol lipid) or 100 µl PBS containing no liposomes. The final concentrations of the copolymer are 15% w/w and 20% w/w containing liposomes at a concentration of 22.3 µmol lipid/ ml (14.8 mg/ml). The vials are placed in a water bath and each solution is heated in 1° C. steps beginning at 26° C. in a thermomixing device (Eppendorf). At each temperature step the gelation is checked by careful inversion of the tube. When the solution is not free-flowing, gelation of the solution occurred, the temperature read from the thermometer is determined as gelation temperature.

3.5. Degradation of Hydrogel/PS-$MAN_3$-Liposome Composites

The in vitro degradation behavior of hydrogel/PS-Man3-liposome composites is evaluated by the mass loss and/or the molecular weight reduction with time upon incubation in phosphate-buffered saline.

Samples (0.2 ml) are incubated in phosphate-buffered saline pH 7.4 at 37° C. under mild agitation in a water bath. The solid residues are removed from the incubation medium at scheduled time intervals and lyophilized. The samples are weighted and the weight loss is calculated. For determination of the molecular weight reduction, the solid residues are solved in cold water and analyzed by gel permeation chromatography using polystyrene standards as described by Qiao et al. (2005).

Example 4: Release of PS-Liposomes from Hydrogels

This example describes the in vitro release characteristics of PS-Liposomes with encapsulated FITC-BSA from thermogelling PLGA-PEG-PLGA hydrogels.

4.1. Synthesis of Thermogelling PLGA-PEG-PLGA Hydrogels

The biodegradable triblock polymer described in this example has a PLG/PEG weight ratio of 2.3 (70/30), and a lactide/glycolide molar ratio of approx. 15/1. Synthesis of the triblock copolymer is performed as described in Example 1.1.

4.2. Synthesis of FITC-BSA-Containing PS-Liposomes

This example describes the synthesis of unilamellar PS-liposomes containing fluorescein isothiocyanate (FITC)-labeled BSA, from a lipid mixture of phosphatidyldserine (PS), either 1,2-Dipalmitoyl-sn-glycero-3-phospho-L-serine sodium salt (Sigma-Aldrich), 1-palmitoyl-2-oleoyl-sn-3-glycerophospho-L-serine (POP-L-S) or bovine brain phosphatidyldserine (Avanti Polar Lipids), phosphatidylcholine (PC), either 1,2-Dipalmitoyl-sn-glycero-3-phosphocholine (Sigma-Aldrich), 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 24.4 mg), mol PC (approx. 22.8 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing FITC-labeled bovine serum albumin (BSA, 1.0 mg/ml, Sigma-Aldrich) is added and multilamellar vesicles are generated by intense vortex dispersion. For the preparation of unilamellar vesicles, the multilamellar preparation is extruded 10 times through a 1 µm pore polycarbonate membrane (Nucleopore, USA). The final liposomal suspension contains approx. 66.6 µmol (39.2 mg) of lipid/1.0 ml.

The amount of encapsulated FITC-BSA in liposomes is determined by dissolving the lipid vesicles with 1% (v/v) Triton X-100 and monitoring the absorbance of FITC-BSA at 495 nm (Cohen et al., 1991).

4.3. In Vitro Release of FITC-BSA-Containing PS-Liposomes from Hydrogel/PS-Liposome Composites The in vitro release of FITC-BSA-containing PS-liposomes from hydrogel/PS-liposome composites is determined after gelling of the hydrogel/PS-liposome composites at 37° C. by monitoring the supernatant for the development of absorbance at 495 nm in the presence of Triton X-100.

Vials are filled with 200 µl water containing different concentrations of the copolymer of Example 2.1. (22.5% w/w, and 30% w/w), cooled to 4° C. and mixed with 100 µl PBS containing liposomes of Example 4.2 (6.7 µmol lipid). The final concentrations of the copolymer are 15% w/w and 20% w/w containing liposomes with encapsulated FITC-BSA at a concentration of 22.3 µmol lipid/ml (13.1 mg/ml). The reaction mixtures are incubated at 37° C. under mild agitation in a water bath until gelling. Thereafter, 1.7 ml of phosphate-buffered saline (PBS) pH 7.4 is added to each sample and incubation at 37° C. is continued. At specified sample collection times 0.5 ml aliquots of the supernatant are withdrawn and replaced by an identical volume of PBS pH 7.4 to maintain release conditions. The amount of released PS-liposomes is determined by measuring encapsulated FITC-BSA via absorbance at 495 nm in the supernatant after dissolving the lipid vesicles with 1% (v/v) Triton X-100 (Cohen et al., 1991) or with fluorescence detection in suitable detection systems.

Example 5: Release of Immune Modula TORS from Hydrogel

This example describes the release characteristics of selected hydrogel-embedded low to moderate molecular weight immune-modulators suitable for enhancing the suppressive function of regulatory T cells and for enhancing phagocytosis of PS-liposomes.

5.1. Release of TNFR1 Inhibitor NAC From PLGA-PEG-PLGA Hydrogels

The PLGA-PEG-PLGA triblock copolymer of Example 1.1 is dissolved at room temperature in phosphate buffered saline (PBS) at pH 7.4, containing 25% or 20% w/v polymer. Varying volumes (10 μl, 20 μl, 40 μl, 80 μl) of N-acetyl-L-cysteine (NAC, ACC) (50 mg/ml PBS (0.3 M) at pH 7.4,) are added to 200 μl gel solution. Then the formulation is placed in a 2 ml vial, incubated at 37° C. for 2 min until gelling, and 1.8 ml of PBS pH 7.4 is added. The vial is incubated at 37° C. At specified sample collection times, the supernatant is withdrawn and replaced by an identical volume of PBS pH 7.4 to maintain release conditions.

The amount of released NAC is determined by an assay for sulfhydryl groups using the reaction of 4,4'-dithiopyridine (4-PDS) with thiols, which gives the corresponding 4-thiopyridone (4-TP) (Grassetti and Murray, 1967). Using this assay, 15 nmol-0.5 μmol NAC is dissolved in 1.5 ml PBS pH 7.2 and mixed with 1.5 ml 2 mM 4-PDS in PBS pH 7.2. UV absorbance of 4-TP is determined at 324 nm (molar extinction coefficient $1.198\times10^4$) immediately after mixing. The method permits determination of less then 0.5 μg SH (Grassetti and Murray, 1967).

For the determination of NAC concentrations below 15 nmol/1.5 ml (10 μM), a more sensitive spectrophotometric assay is used which is based on a coupled two-step redox and complexation procedure (Kukoc-Modun and Radic, 2011). In the first step, Fe(III) is reduced by the sulfhydryl group of NAC to Fe(II). Subsequently, Fe(II) is complexed with 2,4,6-tripyridyl-S-triazine (TPTZ). Acetate buffer (0.5 M), pH 3.6 (2.0 ml) is mixed with 125 μl 10 mM $FeCl_3$, 125 μl 10 mM TPTZ in 0.12 M HCl, and 100 μl NAC solution. After incubation for 60 min at room temperature, the absorbance of the produced Fe(II)-TPTZ complex, which remains constant for 24 hours, is measured at 593 nm. The detection limit of this method for NAC is 0.14 μM.

5.2. Release of TNFR1 Inhibitor GSH from PLGA-PEG-PLGA Hydrogels

In this example, non-methylated glutathione (GSH) is used to study the release characteristics of glutathione and derivatives thereof including S-methylglutathione (GSM) from PLGA-PEG-PLGA hydrogels.

The PLGA-PEG-PLGA triblock copolymer of Example 1.1 is dissolved at room temperature in phosphate buffered saline (PBS) at pH 7.4, containing 25% or 20% w/v polymer. Varying volumes (20 μl, 40 μl, 80 μl) of 10 mM GSH in PBS, pH 7.4, are added to 200 μl gel solution. Then the formulation is placed in a 2 ml vial, incubated at 37° C. for 2 min until gelling, and 1.8 ml of PBS pH 7.4 is added. The vial is incubated at 37° C. At specified sample collection times, the supernatant is withdrawn and replaced by an identical volume of PBS pH 7.4 to maintain release conditions.

The amount of released GSH is determined by an assay for sulfhydryl groups using the reaction of 4,4'-dithiopyridine (4-PDS) with thiols, which gives the corresponding 4-thiopyridone (4-TP). Using this assay, 15 nmol-0.5 μmol GSH is dissolved in 1.5 ml PBS pH 7.2 and mixed with 1.5 ml 2 mM 4-PDS in PBS pH 7.2. UV absorbance of 4-TP is determined at 324 nm (molar extinction coefficient $1.198\times10^4$) immediately after mixing. The method permits determination of less then 0.5 μg SH (Grassetti and Murray, 1967).

For the determination of GSH concentrations below 15 nmol/1.5 ml (10 μM), a more sensitive spectrophotometric assay is used which is based on a coupled two-step redox and complexation procedure (Kukoc-Modun and Radic, 2011). In the first step, Fe(III) is reduced by the sulfhydryl group of GSH to Fe(II). Subsequently, Fe(II) is complexed with 2,4,6-tripyridyl-S-triazine (TPTZ). Acetate buffer (0.5 M), pH 3.6 (2.0 ml) is mixed with 125 μl 10 mM $FeCl_3$, 125 μl 10 mM TPTZ in 0.12 M HCl, and 100 μl GSH solution. After incubation for 60 min at room temperature, the absorbance of the produced Fe(II)-TPTZ complex, which remains constant for 24 hours, is measured at 593 nm.

5.3. Release of TNFR1 Inhibitor SA from PLGA-PEG-PLGA Hydrogels

The PLGA-PEG-PLGA triblock copolymer of Example 1.1 is dissolved at room temperature in phosphate buffered saline (PBS) at pH 7.4, containing 25% or 20% w/v polymer. Varying volumes (10 μl, 20 μl, 40 μl, 80 μl) of 10 mM sodium salicylate (SA) in PBS, pH 7.4, are added to 200 µl gel solution. The solubility of SA in water is 2 g/liter at 20° C. (14.5 mM). Then the formulation is placed in a 2 ml vial, incubated at 37° C. for 2 min until gelling, and 1.8 ml of PBS pH 7.4 is added. The vial is incubated at 37° C. At specified sample collection times, the supernatant is withdrawn and replaced by an identical volume of PBS pH 7.4 to maintain release conditions.

The amount of released SA is determined by derivatization with Fe(III) and quantification of the violet coloured tetraaquosalicylatroiron (III) complex at 530 nm (www.jenway.com (Application note A09-009A; The quantitative determination of the aspirin content of tablets using UV and visible wavelength spectroscopy).

5.4. Release of TNFR1-Specific Antisense ODN from PLGA-PEG-PLGA Hydrogels

First, TNFR1-specific antisense oligonucleotides (ODN) are synthesized using partial phosphorothioate linkages (pPT) to confer nuclease resistance and to reduce nonspecific side effects associated with ODNs having a sulfur moiety at every internucleoside linkage. The Beaucage reagent (Iyer et al., 1990) is used for the synthesis of the TNFR1-specific antisense pPT ODN.

```
Sequence of a suitable 22 mer pPT TNFR1-
specific antisense ODN
a* g* a* a* t t t t a* g* t* g* t* a t g t a* c*
a* a
(asterics indicate phosphorothioate linkages)
```

Purification by anion exchange chromatography, desalting and analysis for purity is performed as described (Ojwang and Rando, 1999). Using the purified 22mer pPT antisense ODN, melting temperature evaluations revealed a Tm of 36.6° C. for a DNA:DNA duplex and a Tm of 3.1° C. for a DNA:RNA duplex (Ojwang and Rando, 1999).

Thereafter, 35 µl of a 1.0 µM solution of the purified 22mer pPT antisense oligodeoxynucleotides (TNFR1-pPT ODN) in PBS, 7.4, are complexed with 3.5 µl of a cationic liposomal preparation (Cellfectin; Life Technologies, USA) in PBS, pH 7.4 (1 mg/ml) containing the cationic lipid tetramethyltetra-palmitylspermine and the phospholipid dioleoylphosphatidyl-ethanolamine, and incubated for 15 min incubation at room temperature.

The PLGA-PEG-PLGA triblock copolymer of Example 1.1 is dissolved at room temperature in PBS at pH 7.4, containing 25% or 20% w/v polymer. Varying volumes (10 µl, 20 µl, 40 µl, 80 µl) of TNFR1-ODN/Cellfectin complexes of Example 1.3. are added to 200 µl gel solution. The formulation is placed in a 2 ml vial, incubated at 37° C. for 2 min until gelling, and 1.8 ml of PBS, pH 7.4, is added. The vial is incubated at 37° C. At specified sample collection times, the supernatant is withdrawn and replaced by an identical volume of PBS pH 7.4 to maintain release conditions.

Released TNFR1-ODNs are liberated from the liposomal complex by the addition of 200 µl 100 mM Tris-HCl, pH 8.0, 5 mM EDTA, 10% Triton X-100 to the supernatant (1.8 ml). Thereafter, the amount of released TNFR1-ODN is determined in 100 µl aliquots of the supernatants by a one-step hybridization ELISA (Wei et al., 2006). Capture and detection of TNFR1-ODN is accomplished on a one-strand capture probe, which is complementary to the TNFR1-ODN without an overhang and contains biotin at the 3'-end and digoxigenin at the 5'-end. For TNFR1-ODN capture probe hybridization 200 nM capture probe in hybridization buffer solution (capture ODN concentration of 200 nM ensures highest hybridization with analytes) is first heated to 95° C. for 5 min in a heating block to disrupt possible secondary structures. Then 100 µl of the capture probe solution is added to 100 µl of the TNFR1-ODN solution in a polystyrene 96-well plate. The mixture is incubated at 42° C. for 2.5 hours. After TNFR1-ODN capture probe hybridization, 150 µl of the solution is transferred to 96-well Reacti-Bind NeutrAvidin-coated polystyrene plates (Pierce, USA) and incubated for 30 min at 37° C. to allow attachment of the biotin-labeled duplex to the coated plates. The plates are washed 6 times with washing buffer, followed by the addition of 150 µl S1 nuclease (60 U in 100 mM NaCl), After incubation for 2 hours at 37° C., the plates are washed 6 times with washing buffer, followed by the addition of 150 µl anti-digoxigenin-alkaline phosphatase (AP) (Roche, USA) diluted 1:2500 with bovine serum albumin blocking buffer (Superblock buffer in Tris-buffered saline, TBS; Pierce, USA) and subsequent incubation for further 30 min at 37° C. with gentle shaking. Thereafter, the plates are washed again 6 times with washing buffer, followed by the addition of 150 µl Attophos (Promega, USA) substrate solution (36 mg Attophos in 60 ml diethanolamine buffer). After 30 min at 37° C. the generated fluorescence is measured at Ex430/Em 560 (filter 550 nm) using a fluorescence microtiter plate reader.

Buffers used for the determination of TNFR1-ODNs include the hybridization buffer (60 mM Na phosphate, pH 7.4, 1.0 M NaCl, 5 mM EDTA, and 0.2% Tween 20), the washing buffer (25 mM Tris-HCl, pH 7.2, 0.15 M NaCl, and 0.2% Tween 20), and the dilution buffer for ODN standards (10 mM Tris-HCl, pH 8.0, 1 mM EDTA).

According to Wei et al. (2006) the one-step hybridization ELISA is linear from 0.025 to 50 nM ODN including phosphorothioate oligonucleotides. Using 60 U S1 nuclease per well, a cutting efficiency of 99.3-99.7% is achieved.

5.5. Release of Calcitriol from PLGA-PEG-PLGA Hydrogels

This example describes the release of calcitriol (1α,25-dihydroxyvitamin D3; 1,25-$(OH)_2$D3) from the hydrogel of Example 1.1. Calcitriol (MW 416,65; solubility: approx. 50 mg/ml of ethanol or approx. 0.15 mg/ml in a 1:5 solution of ethanol:PBS, pH 7.2) is purchased from BioVision Inc.

The PLGA-PEG-PLGA triblock copolymer of Example 1.1. is dissolved at room temperature in 200 µl PBS pH 7.4 containing different concentrations of calcitriol (10 50 µg) to make a 20% w/w or 25% w/w solution. Then the formulation is placed in a 2 ml vial, incubated at 37° C. for 2 min until gelling, and 1.8 ml of PBS pH 7.4 is added. The vial is incubated at 37° C. At specified sample collection times, a sample is withdrawn and replaced by an identical volume of PBS pH 7.4 to maintain release conditions.

The amount of released calcitriol is determined by solid-phase ELISA (Life Science Market)

5.6. Release of Complement Inhibitor Compstatin from PLGA-PEG-PLGA Hydrogels

This example describes the release of the 13-residue cyclic peptide (H-I[CVVQDWGHHRC]T-$NH_2$) (termed compstatin) from the hydrogel of Example 1.1. Compstatin (MW 1550.8 Da; soluble up to 2 mg/ml in 30% acetonitril/water) is purchased from R&D Systems.

The PLGA-PEG-PLGA triblock copolymer of Example 1.1. is dissolved at room temperature in 200 µl PBS pH 7.4 containing different concentrations of compstatin (up to 1 mg) to make a 20% w/w or 25% w/w solution. Then the formulation is placed in a 2 ml vial, incubated at 37° C. for 2 min until gelling, and 0.2 ml of PBS pH 7.4 is added. The vial is incubated at 37° C. At specified sample collection times, a sample is withdrawn and replaced by an identical volume of PBS pH 7.4 to maintain release conditions.

The amount of released compstatin is determined by bicinchoninc acid (BCA) assay using BCA™ Protein Assay Kit (Pierce, USA). The structural and functional integrity of released compstatin is determined by inhibition of the alternative pathway of complement activation using rabbit erythrocytes.

The inhibitory effect of released compstatin on the alternative pathway is determined by measuring the lysis of rabbit erythrocytes (Er) in normal human serum (NHS). A sample of 80 µl containing either released compstatin or different standard concentrations of compstatin is mixed with 7.5 µl NHS, 7.5 µl MgEGTA (0.1 M $MgCl_2$ and 0.1 M EGTA), 15 µl of Er ($1\times10^9$/ml), and 40 µl GVB (5 mM barbital and 145 mM NaCl, pH 7.4). The reaction mixture is incubated at 37° C. for 20 min and stopped by adding 200 µl GVBE (GVB with 10 mM EDTA). After centrifugation, hemolysis is determined at 414 nm. The percentage of lysis is normalized by considering 100% lysis to be equal to lysis occurring in the absence of compstatin. The concentration of compstatin for 50% inhibition of the lysis of rabbit erythrocytes in normal human serum under these conditions is 12 M (Sahu et al., 1996).

5.7. Release of IL-4 Antagonist QY from PLGA-PEG-PLGA Hydrogels

This example describes the release of murine IL-4 antagonist QY (Q116D/Y119D) from the hydrogel of Example 1.1.

5.7.1. Cloning and Expression of Murine IL-4 Antagonist QY.

First, the sequence of the native mature murine IL-4 protein is modified to include a thrombin cleavable N-terminal 6×His-tag and the QY (Q116D/Y119D) mutations. Then the protein sequence is translated into DNA using codon optimization for expression in prokaryotic *E. coli* cells. The resulting sequence is synthesized and amplified using PCR with Pfu polymerase according to the manufacture and annealing temperatures rising from initial 5 cycles at 50° C. to 60° C. and 30 cycles total. The resulting PCF fragment is gel-purified in 1% agarose (GeneJET Gel Extraction Kit, Fermentas) and transferred to a restriction enzyme double digest containing Nde I and Xho I (Fermentas). The restriction digest is again gel-purified and the fragment is ligated into Nde I and Xho I cut pET-22b (Novagen) expression vector.

Recombinant His-tagged murine IL-4 antagonist QY (Q116D/Y119D) is expressed in *E. coli* (BL21(DE3)pLysS; Novagen) at 37° C. Cultures are grown in 1-L batches in minimal medium containing 100 µg/ml ampicillin and 34 µg/ml chloramphenicol. The minimal medium contains the following components: 0.1 M phosphate buffer, pH 7.0, 2 mM $MgSO_4$, 17 mM NaCl, 0.1 mM $CaCl_2$, 5 mg/L $FeSO_4$, 0.2 mg/L $(NH_4)MO_7O_{24}$, 1 mg/L $H_3BO_3$, 0.2 mg/L $CoCl_2$, 0.2 mg/L $CuSO_4$, 2 mg/L $MnSO_4$, and 2 mg/L $ZnSO_4$, supplemented with thymidine, biotin, folic acid, pantothenic acid, niacinamide, pyroxidine phosphate, and thiamine (1 mg/L each). The expression is induced by the addition of isopropyl-D-thiogalactopyranoside to a final concentration of 1 mM after the culture reaches an $OD_{600}$ of approximately 0.6. The cells are allowed to grow for 4 h and then harvested by centrifugation at 5000×g for 10 min at 4° C. The pellet is stored at −20° C.

The insoluble His-tagged murine IL-4 antagonist QY (Q116D/Y119D) is refolded according to patent application EP 11075261.5. The *E. coli* pellet containing the recombinant IL-4 antagonist QY is resuspended in 15 ml of 50 mM Tris-HCl, pH 8.0, and 5 mM EDTA (lysis buffer) containing 2 mg lysozyme and incubated at room temperature for 20 min. The cell lysate is diluted with 60 ml lysis buffer and sonicated. It is then centrifuged at 11,000 rpm for 30 min at 4° C. to collect the pellet containing inclusion bodies. The pellet is washed twice with 60 ml with 2 M urea in lysis buffer and collected by centrifugation as described above. Finally, the pellet is resuspended in 25 ml of 6 M GdnHCl, 50 mM potassium phosphate, pH 8.0, and 1 mM reduced glutathione (extraction buffer) and stirred at room temperature for 10 min. The solution is centrifuged to remove the insoluble portion. The guanidine-extracted IL-4 antagonist QY is loaded onto 15 ml of Ni-charged HisTrap™ FF columns (GE Healthcare) equilibrated with the extraction buffer. The beads are washed with 8 column volumes of 7 M urea and 50 mM potassium phosphate, pH 6.8, to remove the cellular proteins. The His-tagged IL-4 antagonist QY is refolded on the column by the gradual removal of urea through a linear gradient expanding from 100% unfolding buffer to 100% refolding buffer (380 ml at a flow rate of 1 ml/min) using a fast protein liquid chromatography ÄKTA™ system (Pharmacia). The unfolding buffer is composed of 7 M urea, 100 mM NaCl, 50 mM potassium phosphate, pH 6.8, 1 mM reduced glutathione, and 1 mM oxidized glutathione; the refolding buffer has the same composition but without urea. After washing the column with 40 ml refolding buffer, the refolded His-tagged IL-4 antagonist QY is eluted from the column with 100 mM EDTA and 10 mM Tris-HCl, pH 8.0. EDTA is used to chelate divalent cations that can potentially cause protein aggregation during dialysis. The His-tagged IL-4 antagonist QY is then dialyzed against 50 mM TrisHCl, pH 8.0, 5 mM $CaCl_2$), and 100 mM NaCl to remove EDTA. The protein is concentrated to approximately 2 mg/ml.

The His-tag is cleaved overnight by incubation of each mg fusion protein with 10 U thrombin (Sigma) in PBS buffer. The mix is incubated at room temperature overnight. The reaction can be stopped with 1 mM PMSF. Cleavage products are separated by chromatography. Residual thrombin can be removed with pAminonezamidine-Agarose (Sigma) either by batch or chromatographic methods. The cleavage specificity is confirmed by N-terminus sequencing of blotted IL-4 antagonist QY. The His-tag is removed by passing the cleaved protein through Ni-fractogel beads. The purified samples are dialyzed in a desired buffer and kept at 4° C. for short term storage or stored at −70° C. in the presence of 25% glycerol.

The concentration of murine IL-4 or murine IL-4 mutants is determined by ELISA (Mouse IL-4 ELISA MAX™ Deluxe, BioLegend GmbH, Fell) according to the manufacturers instructions.

5.7.2. Release of Murine IL-4 Antagonist QY from Hydrogels.

The PLGA-PEG-PLGA triblock copolymer of Example 1.1. is dissolved at room temperature in PBS pH 7.4 containing different concentrations of the murine IL-4 antagonist QY (0.5 mg/ml up to 1.0 mg/ml) to make a 20% w/w or 25% w/w solution. Then 200 µl of the formulation is placed in a 2 ml vial, incubated at 37° C. for 2 min until gelling, and 1.8 ml of PBS pH 7.4 is added. The vial is incubated at 37° C. At specified sample collection times, a sample is withdrawn and replaced by an identical volume of PBS pH 7.4 to maintain release conditions.

The amount of released murine IL-4 antagonist QY is determined by bicinchoninc acid (BCA) assay using BCA™ Protein Assay Kit (Pierce, USA) and by an ELISA-type assay as described above.

The structural integrity of released murine IL-4 antagonist QY is determined by a cellular binding assay.

The functionality of released murine IL-4 antagonist QY is determined by different in vitro assays. The first assay uses mouse spleen B cells and the determination of their proliferation behavior and cytokine secretion pattern after stimulation with IL-4 in the absence or presence of different concentrations of the mutein. The second assay uses the mouse T cell line CTLL-2 which can be used for the quantification of mouse as well as of human IL-4 activity and thereby of the blocking effect of the mutein. The blocking activity of the mutein will be determined by a proliferation assay, the quantification of the activation of IL-4 regulated genes by RT-PCR, as well as by quantification of IL-4-regulated marker proteins by FACS analyses. The third assay uses immune cells from a reporter mouse that is available in the lab. Stimulation of the cells with IL-4 induces the expression of green fluorescent protein (GFP) which can be used as an activation marker that can be quantified. For all assays an anti-IL-4 blocking antibody serves as positive control.

5.8. Release of Immune Modulator of Phagocytosis ATP from PLGA-PEG-PLGA Hydrogels This example describes the release of the immune modulator of phagocytosis ATP from the hydrogel of Example 1.1.

The PLGA-PEG-PLGA triblock copolymer of Example 1.1 is dissolved at room temperature in phosphate buffered saline (PBS) at pH 7.4, containing 25% or 20% w/v polymer. Varying volumes (10 μl, 20 μl, 40 μl, 80 μl) of ATP (10 mM in PBS, pH 7.4,) are added to 200 μl gel solution. Then the formulation is placed in a 2 ml vial, incubated at 37° C. for 2 min until gelling, and 1.8 ml of PBS pH 7.4 is added. The vial is incubated at 37° C. At specified sample collection times, the supernatant is withdrawn and replaced by an identical volume of PBS pH 7.4 to maintain release conditions.

After 48 hours the samples are measured spectrometrically at 260 nm and the amount of released ATP is calculated as percentage of a reference sample containing a concentration of ATP equaling 100% release.

Example 6: Immunotherapy of OVA-Allergic Mice with Vitamin D3-Derivative Calcipotriol and PS-Liposome-Encapsulated OVA This example investigates the efficacy of allergen-specific immunotherapy of OVA-allergic mice with a) increasing doses of alum-adsorbed OVA and b) with hydrogel-embedded PS-liposomes containing encapsulated OVA and polymer-embedded calcipotriol.

6.1. Animals and Materials

Female wild-type C57BL/6 mice 6 to 10 weeks of age are purchased from Charles River (Sulzfeld, Germany). The animals are kept under specific pathogen-free conditions and maintained on OVA-free diets. Ovalbumin (OVA) Grade V is purchased from Sigma, Imject Alum from Pierce/KMF, rat monoclonal antibodies against murine IgE and IgG1, and goat antisera against murine IgG2a, IgG2b, and IgG3 from BD Pharmigen. Calcipotriol (synonyms: MC 903, calcipotriene; MW 412.62; solubility approx. 50 mg/ml of ethanol or approx. 0.15 mg/ml in a 1:5 solution of ethanol/PBS, pH 7.2) is purchased from MedChemExpress.

6.2. Preparation of Alum-Adsorbed Ovalbumin (OVA)

For immunization, 100 μg of OVA are solved in 0.3 ml of PBS, pH 7.4, and mixed with 0.70 ml Imject Alum (Pierce/KMF). For immunotherapy, 10 mg of OVA are solved in 3.0 ml of PBS, pH 7.4, and mixed with 7.0 ml Imject Alum (Pierce/KMF). From this mixture containing 100 μg alum-adsorbed OVA in 0.3 ml, dilutions are prepared containing in 0.3 ml 90 μg, 60 μg, 30 μg, 15 μg, and 7.5 μg alum-adsorbed OVA.

6.3. Preparation of PS-Liposomes Containing Encapsulated OVA

This example describes the synthesis of unilamellar PS-liposomes containing different quantities of encapsulated OVA from a lipid mixture of phosphatidyldserine (PS), either 1-palmitoyl-2-oleoyl-sn-3-glycerophospho-L-serine (POP-L-S) or bovine brain phosphatidyldserin (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 μmol PS (approx. 24.4 mg), mol PC (approx. 22.8 mg) and 40 μmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing varying concentrations of OVA (0.6 mg/ml, 0.9 mg/ml, 1.2 mg/ml, 1.5 mg/ml, 1.8 mg/ml, and 2.1 mg/ml) is added and multilamellar vesicles are generated by intense vortex dispersion. For the preparation of unilamellar vesicles, the multilamellar preparation is extruded 10 times through a 1 μm pore polycarbonate membrane (Nucleopore, USA). PS-liposomes with a particle size of approx. 1 μm are suitable for efficient uptake by macrophages (Harel-Adar et al., 2011). The final liposomal suspension contains approx. 66.6 μmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated OVA is determined by the micro BCA protein assay (Pierce) after dissolving the liposomes in 0.05 M NaOH/1% SDS.

6.4. Preparation of Hydrogel Solutions Containing Calcipotriol and OVA Encapsulated in PS-Liposomes This example describes the synthesis of different composites comprising hydrogel-embedded calcipotriol and unilamellar PS-liposomes containing different quantities of encapsulated OVA.

First, the PLGA-PEG-PLGA triblock copolymer of Example 1.1., dried under vacuum at room temperature until constant weight, is dissolved in 150 μl PBS, pH 7.4, and 50 μl of calcipotriol in a 1:5 solution of ethanol/PBS, pH 7.4 (150 μg/ml corresponding to 7.5 μg/50 μl) to a concentration of 30% w/v polymer. After cooling to 4° C., the hydrogel-calcipotriol composite is mixed with 100 μl PS-liposomes of Example 6.3 (6.7 μmol lipid) containing different quantities of encapsulated OVA (approx. 40 μg, 60 μg, 80 μg, 100 μg, 120 μg, and 140 μg OVA). The final concentration of the hydrogel is 20% w/v polymer containing 3.3%. ethanol.

6.5 Allergic Sensitization Procedure

Mice are immunized three times by i.p. injection of 100 μl alum-adsorbed OVA (10 μg OVA in 100 μl of PBS/Imject Alum). The second i.p. injection is performed 7 days after the first injection and the third injection 14 days after the first injection.

6.6. Immunotherapy

One week after the third immunization with OVA, mice are subjected to two different modalities of immunotherapy, one based on conventional treatment with increasing doses of alum-adsorbed OVA, the other based on treatment with hydrogel-embedded PS-liposomes containing increasing amounts of OVA in the presence of hydrogel-embedded calcipotriol.

Three groups of wild-type C57BL/6 mice (each group: 10 mice) are subjected to immunotherapy. Group 1: immunization (3× alum-OVA), therapy with increasing doses of alum-OVA only; group 2: immunization (3× alum-OVA), therapy with hydrogel containing increasing doses of OVA encapsulated in PS-liposomes in the presence of hydrogel-embedded calcipotriol; and group 3: immunization (3× alum-OVA), therapy with non-loaded hydrogel (control).

Conventional immunotherapeutic treatment: subcutaneous administration of 0.3 ml PBS (150 µl at two different sites) containing increasing doses of alum-adsorbed OVA (7.5 µg, 15 µg, 30 µg, 60 µg, and 90 µg), performed at 9-day intervals.

Immunotherapeutic approach based on PS-liposomes and calcipotriol: subcutaneous administration of 0.3 ml of a 20% w/v hydrogel (150 µl at two different sites) containing 7.5 µg calcipotriol and increasing doses of PS-liposome-encapsulated OVA (approx. 40 µg, 60 µg, 80 µg, 100 µg, 120 µg, and 140 µg), performed at 9-day intervals.

Control: subcutaneous administration of 0.3 ml of a 20% w/v non-loaded hydrogel (150 µl at two different sites), performed at 9-day intervals.

6.7. Analyses

Mice are bled at day 0 before immunization with OVA, at day 7 after immunization with OVA (before starting immunotherapy), and at day 9 after the last immunotherapeutic treatment. Analyses include the determination of serum levels of OVA-specific antibodies, immediate hypersensitivity in skin responses upon challenge via intradermal injection of OVA and the development of anaphylactic shock upon i.v. injection of OVA.

6.7.1. Analysis of Serum Levels of OVA-Specific Antibodies

Murine anti-OVA IgE and IgG subclasses are determined by ELISA. Plates are coated with 10 µg OVA in 100 µl 0.1 M NaHCO$_3$ for 6 h at 37° C., followed by blocking with 200 µl 3% BSA in PBS, pH 7.4, for 2 h at 37° C. After washing, 100 µl of 1:40 serum dilutions with PBS, pH 7.4, containing 1% BSA are incubated overnight at 4° C. The amount of bound antibody is analyzed using horseradish peroxidise-conjugated antibodies with specificity for murine heavy chain classes (IgE, IgG1, IgG2a, IgG2b, IgG3). Analysis is performed at 405 nm in a microplate autoreader.

6.7.2. Analysis of Serum Levels of Cytokines

The cytokine supernatant is profiled using a panel of 27 cytokines including the Th2 cytokines IL-4, IL-5 and IL-13.

6.7.3. Analysis of FOXP3 and GATA3 mRNA Expression

The read-out for T cell differentiation is FOXP3 and GATA3 mRNA expression, which are inversely regulated. In addition the release is followed in realtime using STAT6 responsive Luciferase systems reporter systems.

6.7.4. Analysis of Immediate Cutaneous Hypersensitivity

Active cutaneous anaphylaxis is tested by skin test after i.v. injection of 200 µl of 0.5% Evans Blue dye in PBS, pH 7.4. Thereafter, the skin of the belly is shaved and four injection sites are marked with a felt tip pen on the skin. Two of the marked sites are injected intradermally with 50 µl PBS, pH 7.4, containing 50 µg OVA, and the other two sites with protein-free PBS, pH 7.4. After 15 min, the mice were killed by cervical dislocation and the skin is stripped off for inspection of the injection sites. The intensity of blue patch formation on the dorsal side of the skin, resulting from fluid extravasation into the injection site upon mast cell degranulation, is scored by two independent observers. Reactions are rated as positive when the diameter of the blue patch exceeds 5 mm, which is pre-marked on the mouse skin. The intensity of bluing is rated in the following manner: 0=no blue patch formation; 1=slight bluing; 2=marked bluing; 3=strong bluing.

6.7.5. Analysis of Anaphylactic Shock Symptoms

Mice are injected i.v. 500 µg OVA in 200 µl 0.5% Evans Blue solution. After 15 min, symptoms of an anaphylactic shock are assessed including bluing (no=0; slight=1; strong=2), pilo erection (no=0; slight=1; strong=2), spontaneous activity (running around =0; sitting passively=1; lying=2), and responsiveness to external stimuli (running away upon touching=0; slight reaction=1; no reaction=2). The animals are considered to be in a state of shock if at least three of the four indicated symptoms are observed by two independent observers who are unaware of the sensitization status of each animal.

6.7.6. Analysis of T Cell Phenotype in Inguinal Lymphnodes

Right and left inguinal lymph nodes are removed and T cell phenotype is tested by in vitro re-stimulation with allergen (ELISPOT/Luminex).

Example 7: Immunotherapy of OVA-Allergic Mice with Murine IL-4/IL-13-Antagonist QY and PS-Liposome-Encapsulated OVA This example investigates the efficacy of allergen-specific immunotherapy of OVA-allergic mice with a) increasing doses of alum-adsorbed OVA and b) with hydrogel-embedded PS-liposomes containing encapsulated OVA and polymer-embedded murine IL-4/IL-13 antagonist QY.

7.1. Animals and Materials

Female wild-type C57BL/6 mice 6 to 10 weeks of age are purchased from Charles River (Sulzfeld, Germany). The animals are kept under specific pathogen-free conditions and maintained on OVA-free diets. Ovalbumin (OVA) Grade V is purchased from Sigma, Imject Alum from Pierce/KMF, rat monoclonal antibodies against murine IgE and IgG1, and goat antisera against murine IgG2a, IgG2b, and IgG3 from BD Pharmigen. The murine IL-4 mutant Q116D/Y119D (the murine equivalent of the human IL-4 double mutant R121D/Y124D) is prepared as described in Example 5.7.

7.2. Preparation of Alum-Adsorbed Ovalbumin (OVA)

For immunization, 100 µg of OVA are solved in 0.3 ml of PBS, pH 7.4, and mixed with 0.70 ml Imject Alum (Pierce/KMF). For immunotherapy, 10 mg of OVA are solved in 3.0 ml of PBS, pH 7.4, and mixed with 7.0 ml Imject Alum (Pierce/KMF). From this mixture containing 100 µg alum-adsorbed OVA in 0.3 ml, dilutions are prepared containing in 0.3 ml 90 µg, 60 µg, 30 µg, 15 µg, and 7.5 µg alum-adsorbed OVA.

7.3. Preparation of PS-Liposomes Containing Encapsulated OVA

This example describes the synthesis of unilamellar PS-liposomes containing different quantities of encapsulated OVA from a lipid mixture of phosphatidyldserine (PS), either 1-palmitoyl-2-oleoyl-sn-3-glycerophospho-L-serine (POP-L-S) or bovine brain phosphatidyldserin (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 24.4 mg), mol PC (approx. 22.8 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing varying concentrations of OVA (0.6 mg/ml, 0.9 mg/ml, 1.2 mg/ml, 1.5 mg/ml, 1.8 mg/ml, and 2.1 mg/ml) is added and multilamellar vesicles are generated by intense vortex dispersion. For the preparation of unilamellar vesicles, the multilamellar preparation is extruded 10 times through a 1 µm pore polycarbonate membrane (Nucleopore, USA). PS-liposomes with a particle size of approx. 1 µm are suitable for efficient uptake by macrophages (Harel-Adar et al., 2011). The final liposomal suspension contains approx. 66.6 µmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated OVA is determined by the micro BCA protein assay (Pierce) after dissolving the liposomes in 0.05 M NaOH/1% SDS.

7.4. Preparation of Hydrogel Solutions Containing Murine IL-4/IL-13 Antagonist QY and OVA Encapsulated in PS-Liposomes This example describes the synthesis of different composites comprising hydrogel-embedded murine IL-4/IL-13 antagonist QY and unilamellar PS-liposomes containing different quantities of encapsulated OVA.

First, the PLGA-PEG-PLGA triblock copolymer of Example 1.1., dried under vacuum at room temperature until constant weight, is dissolved in 150 µl PBS, pH 7.4, and 50 µl of murine IL-4/IL-13 antagonist QY in PBS, pH 7.4 (1.0 mg/ml, corresponding to 50 µg) to a concentration of 30% w/v polymer. After cooling to 4° C., the hydrogel-murine IL-4/IL-13 antagonist QY composite is mixed with 100 µl PS-liposomes of Example 7.3 (6.7 µmol lipid) containing different quantities of encapsulated OVA (approx. 40 µg, 60 µg, 80 µg, 100 µg, 120 µg, and 140 µg OVA). The final concentration of the hydrogel is 20% w/v polymer.

7.5 Allergic Sensitization Procedure

Mice are immunized three times by i.p. injection of 100 µl alum-adsorbed OVA (10 g OVA in 100 µl of PBS/Imject Alum). The second i.p. injection is performed 7 days after the first injection and the third injection 14 days after the first injection.

7.6. Immunotherapy

One week after the third immunization with OVA, mice are subjected to two different modalities of immunotherapy, one based on conventional treatment with increasing doses of alum-adsorbed OVA, the other based on treatment with hydrogel-embedded PS-liposomes containing increasing amounts of OVA in the presence of hydrogel-embedded murine IL-4/IL-13 antagonist QY.

Three groups of wild-type C57BL/6 mice (each group: 10 mice) are subjected to immunotherapy. Group 1: immunization (3× alum-OVA), therapy with increasing doses of alum-OVA only; group 2: immunization (3× alum-OVA), therapy with hydrogel containing increasing doses of OVA encapsulated in PS-liposomes in the presence of hydrogel-embedded murine IL-4/IL-13 antagonist QY; and group 3: immunization (3× alum-OVA), therapy with non-loaded hydrogel (control).

Conventional immunotherapeutic treatment: subcutaneous administration of 0.3 ml PBS (150 µl at two different sites) containing increasing doses of alum-adsorbed OVA (7.5 g, 15 µg, 30 µg, 60 µg, and 90 µg), performed at 9-day intervals.

Immunotherapeutic approach based on PS-liposomes and murine IL-4/IL-13 antagonist QY: subcutaneous administration of 0.3 ml of a 20% w/v hydrogel (150 µl at two different sites) containing 50 µg murine IL-4/IL-13 antagonist QY and increasing doses of PS-liposome-encapsulated OVA (approx. 40 µg, 60 µg, 80 µg, 100 µg, 120 µg, and 140 µg), performed at 9-day intervals.

Control: subcutaneous administration of 0.3 ml of a 20% w/v non-loaded hydrogel (150 µl at two different sites), performed at 9-day intervals.

7.7. Analyses

Mice are bled at day 0 before immunization with OVA, at day 7 after immunization with OVA (before starting immunotherapy), and at day 9 after the last immunotherapeutic treatment. Analyses include the determination of serum levels of OVA-specific antibodies, immediate hypersensitivity in skin responses upon challenge via intradermal injection of OVA and the development of anaphylactic shock upon i.v. injection of OVA.

7.7.1. Analysis of Serum Levels of OVA-Specific Antibodies.

Murine anti-OVA IgE and IgG subclasses are determined by ELISA. Plates are coated with 10 µg OVA in 100 µl 0.1 M NaHCO$_3$ for 6 h at 37° C., followed by blocking with 200 µl 3% BSA in PBS, pH 7.4, for 2 h at 37° C. After washing, 100 µl of 1:40 serum dilutions with PBS, pH 7.4, containing 1% BSA are incubated overnight at 4° C. The amount of bound antibody is analyzed using horseradish peroxidise-conjugated antibodies with specificity for murine heavy chain classes (IgE, IgG1, IgG2a, IgG2b, IgG3). Analysis is performed at 405 nm in a microplate autoreader.

7.7.2. Analysis of Serum Levels of Cytokines

The cytokine supernatant is profiled using a panel of 27 cytokines including the Th2 cytokines IL-4, IL-5 and IL-13.

7.7.3. Analysis of FOXP3 and GATA3 mRNA Expression

The read-out for T cell differentiation is FOXP3 and GATA3 mRNA expression, which are inversely regulated. In addition the release is followed in realtime using STAT6 responsive Luciferase systems reporter systems.

7.7.4. Analysis of Immediate Cutaneous Hypersensitivity

Active cutaneous anaphylaxis is tested by skin test after i.v. injection of 200 µl of 0.5% Evans Blue dye in PBS, pH 7.4. Thereafter, the skin of the belly is shaved and four injection sites are marked with a felt tip pen on the skin. Two of the marked sites are injected intradermally with 50 µl PBS, pH 7.4, containing 50 µg OVA, and the other two sites with protein-free PBS, pH 7.4. After 15 min, the mice were killed by cervical dislocation and the skin is stripped off for inspection of the injection sites. The intensity of blue patch formation on the dorsal side of the skin, resulting from fluid extravasation into the injection site upon mast cell degranulation, is scored by two independent observers. Reactions are rated as positive when the diameter of the blue patch exceeds 5 mm, which is pre-marked on the mouse skin. The intensity of bluing is rated in the following manner: 0=no blue patch formation; 1=slight bluing; 2=marked bluing; 3=strong bluing.

7.7.5. Analysis of Anaphylactic Shock Symptoms

Mice are injected i.v. 500 µg OVA in 200 µl 0.5% Evans Blue solution. After 15 min, symptoms of an anaphylactic shock are assessed including bluing (no=0; slight=1; strong=2), pilo erection (no=0; slight=1; strong=2), spontaneous activity (running around =0; sitting passively=1; lying=2), and responsiveness to external stimuli (running away upon touching=0; slight reaction=1; no reaction=2). The animals are considered to be in a state of shock if at least three of the four indicated symptoms are observed by two independent observers who are unaware of the sensitization status of each animal.

7.7.6. Analysis of T Cell Phenotype in Inguinal Lymphnodes

Right and left inguinal lymph nodes are removed and T cell phenotype is tested by in vitro re-stimulation with allergen (ELISPOT/Luminex).

Example 8: Immunotherapy of OVA-Induced Allergic Airway Inflammation in Mice with Calcipotriol and PS-Liposome-Encapsulated OVA This example investigates the efficacy of allergen-specific immunotherapy of OVA-induced allergic airway inflammation in mice with a) increasing doses of alum-adsorbed OVA and b) with hydrogel-embedded PS-liposomes containing encapsulated OVA and polymer-embedded calcipotriol.

8.1. Animals and Materials

Female wild-type C57BL/6 mice 6 to 10 weeks of age are purchased from Charles River (Sulzfeld, Germany). The animals are kept under specific pathogen-free conditions and maintained on OVA-free diets. Ovalbumin (OVA) Grade V is purchased from Sigma, Imject Alum from Pierce/KMF, rat monoclonal antibodies against murine IgE and IgG1, and goat antisera against murine IgG2a, IgG2b, and IgG3 from BD Pharmigen. Calcipotriol (synonyms: MC 903, calcipotriene; MW 412,62; solubility: approx. 50 mg/ml of ethanol or approx. 0.15 mg/ml in a 1:5 solution of ethanol/PBS, pH 7.2) is purchased from Cayman Chemical Company.

8.2. Preparation of Alum-Adsorbed Ovalbumin (OVA)

For immunization, 100 µg of OVA are solved in 0.3 ml of PBS, pH 7.4, and mixed with 0.70 ml Imject Alum (Pierce/KMF). For immunotherapy, 10 mg of OVA are solved in 3.0 ml of PBS, pH 7.4, and mixed with 7.0 ml Imject Alum (Pierce/KMF). From this mixture containing 100 µg alum-adsorbed OVA in 0.3 ml, dilutions are prepared containing in 0.3 ml 90 µg, 60 µg, 30 µg, 15 µg, and 7.5 µg alum-adsorbed OVA.

8.3. Preparation of PS-Liposomes Containing Encapsulated OVA

This example describes the synthesis of unilamellar PS-liposomes containing different quantities of encapsulated OVA from a lipid mixture of phosphatidyldserine (PS), either 1-palmitoyl-2-oleoyl-sn-3-glycerophospho-L-serine (POP-L-S) or bovine brain phosphatidyldsein (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 24.4 mg), mol PC (approx. 22.8 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing varying concentrations of OVA (0.6 mg/ml, 0.9 mg/ml, 1.2 mg/ml, 1.5 mg/ml, 1.8 mg/ml, and 2.1 mg/ml) is added and multilamellar vesicles are generated by intense vortex dispersion. For the preparation of unilamellar vesicles, the multilamellar preparation is extruded 10 times through a 1 µm pore polycarbonate membrane (Nucleopore, USA). PS-liposomes with a particle size of approx. 1 µm are suitable for efficient uptake by macrophages (Harel-Adar et al., 2011). The final liposomal suspension contains approx. 66.6 µmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated OVA is determined by the micro BCA protein assay (Pierce) after dissolving the liposomes in 0.05 M NaOH/1% SDS.

8.4. Preparation of Hydrogel Solutions Containing Calcipotriol and OVA Encapsulated in PS-Liposomes This example describes the synthesis of different composites comprising hydrogel-embedded calcipotriol and unilamellar PS-liposomes containing different quantities of encapsulated OVA.

First, the PLGA-PEG-PLGA triblock copolymer of Example 1.1., dried under vacuum at room temperature until constant weight, is dissolved in 150 µl PBS, pH 7.4, and 50 µl of calcipotriol in a 1:5 solution of ethanol/PBS, pH 7.4 (150 µg/ml corresponding to 7.5 µg/50 µl) to a concentration of 30% w/v polymer. After cooling to 4° C., the hydrogel-calcipotriol composite is mixed with 100 µl PS-liposomes of Example 6.3 (6.7 µmol lipid) containing different quantities of encapsulated OVA (approx. 40 µg, 60 µg, 80 µg, 100 µg, 120 µg, and 140 µg OVA). The final concentration of the hydrogel is 20% w/v polymer containing 3.3%. ethanol.

8.5. Allergic Sensitization Procedure

Mice are immunized three times by i.p. injection of 100 µl alum-adsorbed OVA (10 µg OVA in 100 µl of PBS/Imject Alum). The second i.p. injection is performed 7 days after the first injection and the third injection 14 days after the first injection.

One week after the last injection the mice are exposed in a Plexiglas chamber (approx. 10×15×25 cm) to 1% (wt/vol) aerosolized OVA in 0.9% saline (using a nebulizer with an airflow rate of 10 L/min), 30 min/day for 10 days.

8.6. Immunotherapy

One week after the final aerosol exposure, mice are subjected to two different modalities of immunotherapy, one based on conventional treatment with increasing doses of alum-adsorbed OVA, the other based on treatment with hydrogel-embedded PS-liposomes containing increasing amounts of OVA in the presence of hydrogel-embedded calcipotriol.

Three groups of wild-type C57BL/6 mice (each group: 10 mice) are subjected to immunotherapy. Group 1: immunization (3× alum-OVA), therapy with increasing doses of alum-OVA only; group 2: immunization (3× alum-OVA), therapy with hydrogel containing increasing doses of OVA encapsulated in PS-liposomes in the presence of hydrogel-embedded calcipotriol; and group 3: immunization (3× alum-OVA), therapy with non-loaded hydrogel (control).

Conventional immunotherapeutic treatment: subcutaneous administration of 0.3 ml PBS (150 µl at two different sites) containing increasing doses of alum-adsorbed OVA (7.5 µg, 15 µg, 30 µg, 60 µg, and 90 µg), performed at 9-day intervals.

Immunotherapeutic approach based on PS-liposomes and calcipotriol: subcutaneous administration of 0.3 ml of a 20% w/v hydrogel (150 µl at two different sites) containing 7.5 µg calcipotriol and increasing doses of PS-liposome-encapsulated OVA (approx. 40 µg, 60 µg, 80 µg, 100 µg, 120 µg, and 140 µg), performed at 9-day intervals.

Control: subcutaneous administration of 0.3 ml of a 20% w/v non-loaded hydrogel (150 µl at two different sites), performed at 9-day intervals.

8.7. Challenge Procedure

One week after completed immune-therapeutic treatment, mice are challenged with 1% aerosolized OVA (as described above), 30 min/day for 3 consecutive days.

8.8. Measurement of AHR: Lung Resistance

Measurement of airway hyperreactivity (AHR), defined as bronchoconstriction in response to methacholine, is performed in two animals of each group. Three days after the final aerosol exposure, the mice are sacrificed by exsanguination after i.p. injection of a ketamine/xylazine overdose, and analyses of bronchoalveolar lavage (BAL), lung tissue, and blood samples are performed.

8.9. Measurements of Pulmonary Resistance

Measurements of pulmonary resistance ($R_L$) are performed in anesthetized, mechanically ventilated mice (Yiamouyiannis et al., 1999). After anesthetizing the animals with pentobarbital (75 mg/kg i.p. injection), the abdominal inferior vena cava is cannulated, and a tracheostomy catheter is placed. The chest is opened by a small anterior incision, and the animal is placed in a whole-body plethysmograph. Mechanical ventilation is established with a small rodent respirator delivering a 10 ml/kg tidal volume at 140 breaths/minute, with a positive end-expiratory pressure (PEEP) of 3 cm $H_2O$. Values for $R_L$ are calculated by analysis of electrical signals proportional to lung volume, airflow, and transpulmonary pressure. Changes in lung volume are determined from the measured changes in plethysmographic pressure and are differentiated over time to obtain flow measurements. Transpulmonary pressure is obtained from the difference between measured pressures at the airway opening and within the plethysmograph. After the establishment of baseline lung function, the animal receives sequentially increasing intravenous doses of methacholine (Sigma; 3 to 3000 μg/ml in 1 ml/kg body weight increments). Maximal $R_L$ responses are determined from measurements averaged over 6-second intervals. Pulmonary function is allowed to return to baseline values before each subsequent dose.

8.10. Bronchoalveolar Lavage (BAL) Analysis

The lungs from five animals of each group are lavaged in situ with five 1 ml aliquots of sterile saline, with 3 to 4 ml BAL fluid recovered from each animal. The BAL is centrifuged and resulting cell pellets are suspended in 250 μl saline. BAL protein concentrations are measured in the supernatants by the bicinchoninc acid (BCA) assay using the BCA™ Protein Assay Kit (Pierce, USA) and bovine serum albumin as standard. Total leukocytes are counted in a hemocytometer using trypan blue dye exclusion as a measure of viability. Cytospin slides are made and stained with May-Grunwald/Giemsa to determine the BAL cell differential. The remaining cells are analyzed by fluorescence flow cytometry. For these analyses, BAL samples are washed in phosphate-buffered saline (PBS) containing 0.2% bovine serum albumin and 0.1% $NaN_3$. Aliquots containing $10^4$ to $10^5$ cells are incubated with 100 μl of appropriately diluted antibodies for 30 min at 4° C. After staining, the cells are washed twice with the above PBS solution, and relative fluorescence intensities are determined on a 4-decade log scale by flow cytometric analysis using a FACScan (Becton Dickinson). Fluorescent monoclonal antibodies used for the fluorescence flow cytometric analyses are directed against B cell and T cell antigens including CD3ε, TCRβ, TCRδ, CD4, CD8, and CD45.

8.11. Analysis of Serum Levels of OVA-Specific Antibodies

Mice are bled at day 0 before immunization with OVA, one week after immunization with OVA (before starting immunotherapy), and two weeks after the last immunotherapeutic treatment. Analyses include the determination of serum levels of OVA-specific antibodies and cytokines.

Murine anti-OVA IgE and IgG subclasses are determined by ELISA. Plates are coated with 10 μg OVA in 100 μl 0.1 M $NaHCO_3$ for 6 h at 37° C., followed by blocking with 200 μl 3% BSA in PBS, pH 7.4, for 2 h at 37° C. After washing, 100 μl of 1:40 serum dilutions with PBS, pH 7.4, containing 1% BSA are incubated overnight at 4° C. The amount of bound antibody is analyzed using horseradish peroxidise-conjugated antibodies with specificity for murine heavy chain classes (IgE, IgG1, IgG2a, IgG2b, IgG3). Analysis is performed at 405 nm in a microplate autoreader.

8.12. Analysis of Serum Levels of Cytokines

The cytokine supernatant is profiled using a panel of 27 cytokines including the TH2 cytokines IL-4, IL-5 and IL-13.

8.13. Tissue Analysis

For tissue immunofluorescence, unmanipulated lungs (not exposed to BAL or methacholine) are excised, cut into small pieces, and are rapidly frozen in optimal cutting temperature embedding media. The pieces are then cut into 5 μm frozen sections using a Hacker cryostat, mounted onto microscope slides, and stored at −20° C. For immunofluorescence staining, the slides are fixed in acetone (−20° C.) for 5 minutes, dried, and blocked with 1% ChromPure IgG solution (Jackson ImmunoResearch) for 30 min at room temperature. After two washes with PBS containing 1% $NaN_3$, specific fluorescent monoclonal antibodies are added to the tissue and incubated for 60 min in a humidity chamber. Slides are then washed twice with PBS containing 1% $NaN_3$, and then analyzed by fluorescence microscopy.

For staining with hematoxylin and eosin (H&E), unmanipulated lungs (not exposed to BAL or methacholine) are excised, fixed with 10% buffered formalin, and stained with H&E according to standard protocols.

Example 9: Immunotherapy of OVA-Induced Allergic Airway Inflammation in Mice with Murine IL-4/IL-13 Antagonist QY and PS-Liposome-Encapsulated Ova This example investigates the efficacy of allergen-specific immunotherapy of OVA-induced allergic airway inflammation in mice with a) increasing doses of alum-adsorbed OVA and b) with hydrogel-embedded PS-liposomes containing encapsulated OVA and polymer-embedded murine IL-4/IL-13 antagonist QY.

9.1. Animals and Materials

Female wild-type C57BL/6 mice 6 to 10 weeks of age are purchased from Charles River (Sulzfeld, Germany). The animals are kept under specific pathogen-free conditions and maintained on OVA-free diets. Ovalbumin (OVA) Grade V is purchased from Sigma, Imject Alum from Pierce/KMF, rat monoclonal antibodies against murine IgE and IgG1, and goat antisera against murine IgG2a, IgG2b, and IgG3 from BD Pharmigen. The murine IL-4 mutant Q116D/Y119D (the murine equivalent of the human IL-4 double mutant R121D/Y124D) is prepared as described in Example 5.7.

9.2. Preparation of Alum-Adsorbed Ovalbumin (OVA)

For immunization, 100 μg of OVA are solved in 0.3 ml of PBS, pH 7.4, and mixed with 0.70 ml Imject Alum (Pierce/KMF). For immunotherapy, 10 mg of OVA are solved in 3.0 ml of PBS, pH 7.4, and mixed with 7.0 ml Imject Alum (Pierce/KMF). From this mixture containing 100 μg alum-adsorbed OVA in 0.3 ml, dilutions are prepared containing in 0.3 ml 90 μg, 60 μg, 30 μg, 15 μg, and 7.5 μg alum-adsorbed OVA.

9.3. Preparation of PS-Liposomes Containing Encapsulated OVA

This example describes the synthesis of unilamellar PS-liposomes containing different quantities of encapsulated OVA from a lipid mixture of phosphatidyldserine (PS), either 1-palmitoyl-2-oleoyl-sn-3-glycerophospho-L-serine (POP-L-S) or bovine brain phosphatidyldserin (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 24.4 mg), mol PC (approx. 22.8 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing varying concentrations of OVA (0.6 mg/ml, 0.9 mg/ml, 1.2 mg/ml, 1.5 mg/ml, 1.8 mg/ml, and 2.1 mg/ml) is added and multilamellar vesicles are generated by intense vortex dispersion. For the preparation of unilamellar vesicles, the multilamellar preparation is extruded 10 times through a 1 µm pore polycarbonate membrane (Nucleopore, USA). PS-liposomes with a particle size of approx. 1 µm are suitable for efficient uptake by macrophages (Harel-Adar et al., 2011). The final liposomal suspension contains approx. 66.6 µmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated OVA is determined by the micro BCA protein assay (Pierce) after dissolving the liposomes in 0.05 M NaOH/1% SDS.

9.4. Preparation of Hydrogel Solutions Containing the Murine IL-4/IL-13 Antagonist QY and OVA Encapsulated in PS-Liposomes This example describes the synthesis of different composites comprising hydrogel-embedded murine IL-4/IL-13 antagonist QY and unilamellar PS-liposomes containing different quantities of encapsulated OVA.

First, the PLGA-PEG-PLGA triblock copolymer of Example 1.1., dried under vacuum at room temperature until constant weight, is dissolved in 150 µl PBS, pH 7.4, and 50 µl of murine IL-4/IL-13 antagonist QY in PBS, pH 7.4 (1.0 mg/ml, corresponding to 50 µg) to a concentration of 30% w/v polymer. After cooling to 4° C., the hydrogel-murine IL-4/IL-13 antagonist QY composite is mixed with 100 µl PS-liposomes of Example 7.3 (6.7 µmol lipid) containing different quantities of encapsulated OVA (approx. 40 µg, 60 µg, 80 µg, 100 µg, 120 µg, and 140 µg OVA). The final concentration of the hydrogel is 20% w/v polymer.

9.5. Allergic Sensitization Procedure

Mice are immunized three times by i.p. injection of 100 µl alum-adsorbed OVA (10 g OVA in 100 µl of PBS/Imject Alum). The second i.p. injection is performed 7 days after the first injection and the third injection 14 days after the first injection.

One week after the last injection the mice are exposed in a Plexiglas chamber (approx. 10×15×25 cm) to 1% (wt/vol) aerosolized OVA in 0.9% saline (using a nebulizer with an airflow rate of 10 L/min), 30 min/day for 10 days.

9.6. Immunotherapy

One week after the final aerosol exposure, mice are subjected to two different modalities of immunotherapy, one based on conventional treatment with increasing doses of alum-adsorbed OVA, the other based on treatment with hydrogel-embedded PS-liposomes containing increasing amounts of OVA in the presence of hydrogel-embedded murine IL-4/IL-13 antagonist QY.

Three groups of wild-type C57BL/6 mice (each group: 10 mice) are subjected to immunotherapy. Group 1: immunization (3× alum-OVA), therapy with increasing doses of alum-OVA only; group 2: immunization (3× alum-OVA), therapy with hydrogel containing increasing doses of OVA encapsulated in PS-liposomes in the presence of hydrogel-embedded murine IL-4/IL-13 antagonist QY; and group 3: immunization (3× alum-OVA), therapy with non-loaded hydrogel (control).

Conventional immunotherapeutic treatment: subcutaneous administration of 0.3 ml PBS (150 µl at two different sites) containing increasing doses of alum-adsorbed OVA (7.5 µg, 15 µg, 30 µg, 60 µg, and 90 µg), performed at 9-day intervals.

Immunotherapeutic approach based on PS-liposomes and murine IL-4/IL-13 antagonist QY: subcutaneous administration of 0.3 ml of a 20% w/v hydrogel (150 µl at two different sites) containing 50 µg murine IL-4/IL-13 antagonist QY and increasing doses of PS-liposome-encapsulated OVA (approx. 40 µg, 60 µg, 80 µg, 100 µg, 120 µg, and 140 µg), performed at 9-day intervals.

Control: subcutaneous administration of 0.3 ml of a 20% w/v non-loaded hydrogel (150 µl at two different sites), performed at 9-day intervals.

9.7. Challenge Procedure

One week after completed immune-therapeutic treatment, mice are challenged with 1% aerosolized OVA (as described above), 30 min/day for 3 consecutive days.

9.8. Measurement of AHR: Lung Resistance

Measurement of airway hyperreactivity (AHR), defined as bronchoconstriction in response to methacholine, is performed in two animals of each group. Three days after the final aerosol exposure, the mice are sacrificed by exsanguination after i.p. injection of a ketamine/xylazine overdose, and analyses of bronchoalveolar lavage (BAL), lung tissue, and blood samples are performed.

9.9. Measurements of Pulmonary Resistance

Measurements of pulmonary resistance ($R_L$) are performed in anesthetized, mechanically ventilated mice (Yiamouyiannis et al., 1999). After anesthetizing the animals with pentobarbital (75 mg/kg i.p. injection), the abdominal inferior vena cava is cannulated, and a tracheostomy catheter is placed. The chest is opened by a small anterior incision, and the animal is placed in a whole-body plethysmograph. Mechanical ventilation is established with a small rodent respirator delivering a 10 ml/kg tidal volume at 140 breaths/minute, with a positive end-expiratory pressure (PEEP) of 3 cm $H_2O$. Values for $R_L$ are calculated by analysis of electrical signals proportional to lung volume, airflow, and transpulmonary pressure. Changes in lung volume are determined from the measured changes in plethysmographic pressure and are differentiated over time to obtain flow measurements. Transpulmonary pressure is obtained from the difference between measured pressures at the airway opening and within the plethysmograph. After the establishment of baseline lung function, the animal receives sequentially increasing intravenous doses of methacholine (Sigma; 3 to 3000 µg/ml in 1 ml/kg body weight increments). Maximal $R_L$ responses are determined from measurements averaged over 6-second intervals. Pulmonary function is allowed to return to baseline values before each subsequent dose.

9.10. Bronchoalveolar Lavage (BAL) Analysis

The lungs from five animals of each group are lavaged in situ with five 1 ml aliquots of sterile saline, with 3 to 4 ml BAL fluid recovered from each animal. The BAL is centrifuged and resulting cell pellets are suspended in 250 µl saline. BAL protein concentrations are measured in the supernatants by the bicinchoninc acid (BCA) assay using the BCA™ Protein Assay Kit (Pierce, USA) and bovine serum albumin as standard. Total leukocytes are counted in a hemocytometer using trypan blue dye exclusion as a measure of viability. Cytospin slides are made and stained with May-Grunwald/Giemsa to determine the BAL cell differential. The remaining cells are analyzed by fluorescence flow cytometry. For these analyses, BAL samples are washed in phosphate-buffered saline (PBS) containing 0.2% bovine serum albumin and 0.1% $NaN_3$. Aliquots containing $10^4$ to $10^5$ cells are incubated with 100 µl of appropriately diluted antibodies for 30 min at 4° C. After staining, the cells are washed twice with the above PBS solution, and relative fluorescence intensities are determined on a 4-decade log scale by flow cytometric analysis using a FACScan (Becton Dickinson). Fluorescent monoclonal antibodies used for the fluorescence flow cytometric analyses are directed against B cell and T cell antigens including CD3ε, TCRβ, TCRδ, CD4, CD8, and CD45.

9.11. Analysis of Serum Levels of OVA-Specific Antibodies

Mice are bled at day 0 before immunization with OVA, one week after immunization with OVA (before starting immunotherapy), and two weeks after the last immunotherapeutic treatment. Analyses include the determination of serum levels of OVA-specific antibodies and cytokines.

Murine anti-OVA IgE and IgG subclasses are determined by ELISA. Plates are coated with 10 µg OVA in 100 µl 0.1 M $NaHCO_3$ for 6 h at 37° C., followed by blocking with 200 µl 3% BSA in PBS, pH 7.4, for 2 h at 37° C. After washing, 100 µl of 1:40 serum dilutions with PBS, pH 7.4, containing 1% BSA are incubated overnight at 4° C. The amount of bound antibody is analyzed using horseradish peroxidise-conjugated antibodies with specificity for murine heavy chain classes (IgE, IgG1, IgG2a, IgG2b, IgG3). Analysis is performed at 405 nm in a microplate autoreader.

9.12. Analysis of Serum Levels of Cytokines

The cytokine supernatant is profiled using a panel of 27 cytokines including the TH2 cytokines IL-4, IL-5 and IL-13.

9.13. Tissue Analysis

For tissue immunofluorescence, unmanipulated lungs (not exposed to BAL or methacholine) are excised, cut into small pieces, and are rapidly frozen in optimal cutting temperature embedding media. The pieces are then cut into 5 µm frozen sections using a Hacker cryostat, mounted onto microscope slides, and stored at –20° C. For immunofluorescence staining, the slides are fixed in acetone (–20° C.) for 5 minutes, dried, and blocked with 1% ChromPure IgG solution (Jackson ImmunoResearch) for 30 min at room temperature. After two washes with PBS containing 1% $NaN_3$, specific fluorescent monoclonal antibodies are added to the tissue and incubated for 60 min in a humidity chamber. Slides are then washed twice with PBS containing 1% $NaN_3$, and then analyzed by fluorescence microscopy.

For staining with hematoxylin and eosin (H&E), unmanipulated lungs (not exposed to BAL or methacholine) are excised, fixed with 10% buffered formalin, and stained with H&E according to standard protocols.

Example 10: Immunotherapy of Autoimmune Diabetes in Mice with Vitamin D3-Derivative Calcipotriol and PS-Liposome-Encapsulated MT-HSP65-Derived Peptide 277

This example investigates the efficacy of peptide immunotherapy of spontaneous autoimmune diabetes (IDDM; insulin-dependent diabetes mellitus) in non-obese diabetic (NOD/Lt) mice using respective subcutaneous injections of alum-adsorbed MT-hsp65-derived peptide p277 or hydrogel-embedded calcipotriol and hydrol-embedded PS-liposomes containing encapsulated MT-hsp65-derived peptide p277.

The 65 kDa heat shock protein of *Mycobacterium tuberculosis* (MT-hsp65) contains a peptide sequence that is cross-reactive with a beta-cell target antigen (termed hsp65 cross-reactive; hsp65-CR) in non-obese diabetic (NOD/Lt) mice (Elias et al., 1990). The onset of beta-cell destruction is associated with the spontaneous development of anti-hsp65 T lymphocytes. Subsequently hsp65-CR becomes detectable in the sera of prediabetic mice (72.5±8.3 days before IDDM) and some weeks later anti-hsp65 antibodies (44±4.3 days before IDDM), anti-insulin antibodies (29±5.5 days before IDDM), and anti-idiotypic antibodies to insulin (19±2.7 days before IDDM) become detectable. The hsp65-CR, the autoantibodies, and the T cell reactivity then decline with the development of overt insulin-dependent diabetes mellitus. The mean age of onset of spontaneous IDDM for 14 out of 18 female NOD/Lt mice (77.8%) is 150±8.3 days (Elias et al., 1990).

In young prediabetic NOD/Lt mice, MT-hsp65 can be used either to induce diabetes or to vaccinate against diabetes, depending on its form of administration. Four- to 5-week old female NOD/Lt mice treated with a single intraperitoneal (i.p.) injection of MT-hsp65 (50 µg) emulsified in incomplete Freund's adjuvans (IFA), developed within 30 days after the treatment diabetes, although the induced diabetes was transient and mice recovered at the age of 6-8 months. In contrast, treatment with a single i.p. injection of MT-hsp65 (50 g) in PBS (non-immunogenic treatment) did not cause the development of diabetes within the period of 30 days and reduced the development of IDDM at later ages (6-8 months) to a significantly extent (Elias et al., 1990).

A 23-mer peptide (VLGGG CALLRC IPALD SLTPA NED; termed p277, SEQ ID NO.: 6) derived from MT-hsp65 was also shown to be protective (Elias et al., 1991). None of 10 one month old female NOD/Lt mice treated with a single i.p. injection of 50 µg of p277 emulsified in IFA, followed two weeks later by another i.p. injection of MT-hsp65 (50 µg) emulsified in IFA, developed diabetes within a period of 30 days. Furthermore, the incidence of spontaneous IDDM in these mice at the age of 8 months was reduced to approximately 30% (Elias et al., 1991).

Important for immunotherapeutic purposes is the fact that p277 is not diabetogenic. None of 7 one month old female prediabetic NOD/Lt mice treated with a single i.p. injection of 50 µg of p277 emulsified in IFA, developed blood glucose levels higher than 130 mg/dl within a period of 3 weeks (Elias et al., 1991). Due to the non-diabetogenic nature of p277, immunotherapy does not require the application of increasing doses of p277. Instead, the immunotherapy is performed with repetitive doses of 100 µg of alum-absorbed p277 and 120 µg of PS-liposome-encapsulated p277.

10.1. Animals

Female NOD/Lt mice 4 weeks of age are purchased from Jackson Laboratory. The animals are kept under specific pathogen-free conditions.

Diabetes development in NOD mice is characterized by insulitis, a leukocytic infiltrate of the pancreatic islets. Marked decreases in pancreatic insulin content occur in females at about 12 weeks of age (Gaskins et al., 1992) and several weeks later in males. Onset of diabetes is marked by moderate glycosuria (1+ reading on Lilly Tes-Tape™) and a non-fasting plasma glucose higher than 250 mg/dl. It is best to begin monitoring for development of glycosuria at weekly intervals starting at 10 weeks of age.

10.2. Materials

Imject Alum is obtained from Pierce/KMF. Calcipotriol (synonyms: MC 903, calcipotriene; MW 412,62; solubility: approx. 50 mg/ml of ethanol or approx. 0.15 mg/ml in a 1:5 solution of ethanol:PBS, pH 7.2) is purchased from Cayman Chemical Company. The MT-hsp65-derived 23-mer peptide (VLGGG CALLRC IPALD SLTPA NED; termed p277) is synthesized by solid-phase peptide synthesis and purified by HPLC according to standard procedures.

10.3. Cloning, Expression and Purification of MT-hsp65

The 65 kDa heat shock protein of *Mycobacterium tuberculosis* (MT-hsp65) and control antigen from *E. coli* transfected without the MT-hsp65 gene are prepared as described (Thole et al., 1987; van Eden et al., 1988).

10.4. Preparation of Alum-Adsorbed Peptide p277

Ten mg of p277 are solved in 3.0 ml of PBS, pH 7.4, and added to 7.0 ml Imject Alum (Pierce/KMF), giving a concentration of 100 µg alum-adsorbed p277 in 0.1 ml alum suspension. For immunotherapy with alum-adsorbed p277, a 3-fold diluted alum suspension in PBS, pH 7.4. is used containing 100 µg alum-adsorbed p277 in 0.3 ml.

10.5. Preparation of PS-Liposomes Containing Encapsulated p277

This example describes the synthesis of unilamellar PS-liposomes containing encapsulated peptide p277 from a lipid mixture of phosphatidyldserine (PS), either 1-palmitoyl-2-oleoyl-sn-3-glycerophospho-L-serine (POP-L-S) or bovine brain phosphatidyldserin (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 24.4 mg), mol PC (approx. 22.8 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing 1.8 µg MT-hsp65-derived 23-mer peptide p277 (VLGGG CALLRC IPALD SLTPA NED, SEQ ID NO.: 6) is added and multilamellar vesicles are generated by intense vortex dispersion. For the preparation of unilamellar vesicles, the multilamellar preparation is extruded 10 times through a 1 µm pore polycarbonate membrane (Nucleopore, USA). PS-liposomes with a particle size of approx. 1 µm are suitable for efficient uptake by macrophages (Harel-Adar et al., 2011). The final liposomal suspension contains approx. 66.6 µmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated peptide p277 is determined by the micro BCA protein assay (Pierce) after dissolving the liposomes in 0.05 M NaOH/1% SDS.

10.6. Preparation of Hydrogel Solutions Containing Calcipotriol and p277 Encapsulated in PS-Liposomes This example describes the synthesis of composites comprising hydrogel-embedded calcipotriol and unilamellar PS-liposomes containing encapsulated peptide p277.

First, the PLGA-PEG-PLGA triblock copolymer of Example 1.1., dried under vacuum at room temperature until constant weight, is dissolved in 150 µl PBS, pH 7.4, and 50 µl of calcipotriol in a 1:5 solution of ethanol/PBS, pH 7.4 (150 µg/ml corresponding to 7.5 µg/50 µl) to a concentration of 30% w/v polymer. After cooling to 4° C., the hydrogel-calcipotriol composite is mixed with 100 µl PS-liposomes of Example 10.5. (6.7 µmol lipid) containing approx. 120 µg peptide p277. The final concentration of the hydrogel is 20% w/v polymer containing 3.3%. ethanol.

10.7. Methods to Identify Autoimmune Diabetes (IDDM)

Detection of serum anti-hsp65 antibodies (44±4.3 days before overt IDDM) and serum anti-insulin antibodies (29±5.5 days before overt IDDM) are used to analyze the development of autoimmune diabetes. Overt IDDM is identified by elevated blood glucose levels of approx. 200 mg/dl or greater.

For the analysis of serum anti-hsp65 antibodies and serum anti-insulin antibodies, microtiter plates are coated with 5 µg MT-hsp65 in 100 µl 0.1 M NaHCO$_3$ or 5 µg insulin in 100 µl 0.1 M NaHCO$_3$ for 6 h at 37° C., followed by blocking with 200 µl 13% BSA in PBS, pH 7.4, for 2 h at 37° C. After washing, 100 µl of 1:50 serum dilutions with PBS, pH 7.4, containing 1% BSA are incubated overnight at 4° C. The amount of bound antibody is analyzed using horseradish peroxidise-conjugated goat anti-mouse immunoglobulin (Becton Dickinson). Analysis is performed at 405 nm in a microplate autoreader.

For the determination of blood glucose, blood is removed from the tail vein of individual mice and the concentration of glucose is measured using a glucose meter (Bayer Diagnostics). A mouse is considered to be diabetic if the blood glucose is >3 standard deviations above the mean of that measured in nondiabetic or prediabetic control mice without insulitis, approx. 200 mg/dl or greater.

10.8. Immunotherapy

Three sets of female NOD/Lt mice are subjected to immunotherapy, the first at the age of 110-120 days characterized by the detection of serum anti-hsp65 antibodies (approx. 6 weeks before overt IDDM), the second at the age of 130-140 days characterized by the detection of serum anti-hsp65 antibodies and serum anti-insulin antibodies (approx. 3 weeks before overt IDDM), the third at the age of 180-200 days with overt IDDM characterized by blood glucose levels of approx. 200 mg/dl or greater.

Each set of mice is subjected to three different modalities of immunotherapy (groups of 10 mice for each treatment modality). Treatment of group 1 is based on conventional treatment with of alum-adsorbed MT-hsp65-derived 23-mer peptide (VLGGG CALLRC IPALD SLTPA NED; SEQ ID NO.: 6, termed p277). For the treatment of group 2, hydrogel-embedded calcipotriol and hydrogel-embedded PS-liposomes containing encapsulated peptide p277 is employed. For the treatment of group 3, non-loaded hydrogel (control) is used.

Conventional immunotherapeutic treatment: subcutaneous administration of 0.3 ml PBS (150 μl at two different sites) containing 100 μg alum-adsorbed p277 OVA, performed eight times at 5-day intervals.

Immunotherapeutic approach based on PS-liposomes and calcipotriol: subcutaneous administration of 0.3 ml of a 20% w/v hydrogel (150 μl at two different sites) containing 7.5 μg calcipotriol and 120 μg of PS-liposome-encapsulated peptide p277, performed eight times at 5-day intervals.

Control: subcutaneous administration of 0.3 ml of a 20% w/v non-loaded hydrogel (150 μl at two different sites), performed eight times at 5-day intervals.

10.9. Analyses During and after Immunotherapy

Analyses include the determination of serum anti-hsp65 antibodies, serum anti-insulin antibodies, and blood glucose levels by methods described above. Analyses are performed at day 8, 18, 28 and 38 after the start of immunotherapy and two weeks after completion of immunotherapy (49 days after the start of immunotherapy). A final analysis is performed five weeks after completion of immunotherapy (corresponding to 70 days after the start of immunotherapy) to evaluate the incidence of IDDM.

Example 11: Immunotherapy of Experimental Autoimmune Encephalomyelitis (EAE) in Mice with Calcipotriol and PS-Liposome-Encapsulated Peptide $PLP_{139-151}$ This example investigates the efficacy of peptide immunotherapy of remitting-relapsing EAE in SJL mice induced by proteolipid protein fragment 139-151 ($PLP_{139-151}$) emulsified in complete Freund's adjuvant (CFA), with a) alum-adsorbed $PLP_{139-151}$ and b) with hydrogel-embedded PS-liposomes containing encapsulated $PLP_{139-151}$ and polymer-embedded calcipotriol. This model is used for testing the efficacy of therapy on the development of EAE relapses.

$PLP_{139-151}$/CFA-induced remitting-relapsing EAE in SJL mice most strongly resembles the remitting-relapsing form of MS, the most common form of MS. Mice develop a first episode of paralysis 11-15 days after immunization. The first wave of EAE lasts several days (peak of disease: 1-3 days) and, similar to most MS patients, most mice fully or almost fully recover from this first wave of paralysis within 7-10 days. After a disease-free period, which can last from one day to several months, 50-80% of the mice develop a second wave of paralysis (relapse) during the first 5-7 weeks after immunization. After several months, almost all mice will have relapsed. As mice are cobserved longer, more relapses will occur and less recovery will occur. Each individual mouse will have a different course of EAE after the first relapse.

Concomitant injection of pertussis toxin (PTX) in PBS on the day of immunization enhances the development of EAE (first episode 9-13 days after immunization) and increases the severity of the first wave, but reduces the incidence (40-60% during the first 5-7 weeks after immunization) and severity of relapses in SJL mice.

The ability of T cell epitope-containing peptides to downregulate the disease course of EAE is well documented (for a review, see Badawi and Siahaan, 2012). For example, EAE induced with a combination of myelin basic protein (MBP) and myelin oligodendrocyte glycoprotein (MOG) has been ameliorated by i.v. administration of a combination of MBP- and MOG-derived peptides (125 nmol each) every other day from day 7 to day 19 after EAE induction (Leadbetter et al., 1998).

11.1. Materials $PLP_{139-151}$ peptide emulsified in complete Freund's adjuvant is obtained from Hooke Laboratories, Inc., USA (Hooke Kit EK-0120), Imject Alum from Pierce/KMF. Calcipotriol (synonyms: MC 903, calcipotriene; MW 412,62; solubility: approx. 50 mg/ml of ethanol or approx. 0.15 mg/ml in a 1:5 solution of ethanol:PBS, pH 7.2) is purchased from Cayman Chemical Company.

11.2. Synthesis of $PLP_{139-151}$ Peptide

The 13-mer peptide HSLGKWLGHPDKF (MW 1521.73) corresponding to amino acid residues 139-151 of proteolipid protein (PLP) is synthesized by solid-phase peptide synthesis and purified by HPLC according to standard procedures.

11.3. Preparation of Alum-Adsorbed $PLP_{139-151}$ Peptide

Twenty mg of $PLP_{139-151}$ peptide is solved in 3.0 ml of PBS, pH 7.4, and added to 7.0 ml Imject Alum (Pierce/KMF), giving a mixture containing 200 μg (approx. 130 nmol) alum-adsorbed $PLP_{139-151}$ peptide in 0.1 ml suspension. For immunotherapy with alum-adsorbed $PLP_{139-151}$ peptide, a 3-fold diluted alum suspension in PBS, pH 7.4. is used containing 100 μg alum-adsorbed $PLP_{139-151}$ peptide in 0.3 ml.

11.4. Preparation of PS-Liposomes Containing Encapsulated $PLP_{139-151}$ Peptide This example describes the synthesis of unilamellar PS-liposomes containing encapsulated $PLP_{139-151}$ peptide from a lipid mixture of phosphatidyldserine (PS), either 1-palmitoyl-2-oleoyl-sn-3-glycerophospho-L-serine (POP-L-S) or bovine brain phosphatidyldserin (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 μmol PS (approx. 24.4 mg), mol PC (approx. 22.8 mg) and 40 μmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing 3.3 mg $PLP_{139-151}$ peptide is added and multilamellar vesicles are generated by intense vortex dispersion. For the preparation of unilamellar vesicles, the multilamellar preparation is extruded 10 times through a 1 μm pore polycarbonate membrane (Nucleopore, USA). PS-liposomes with a particle size of approx. 1 m are suitable for efficient uptake by macrophages (Harel-Adar et al., 2011). The final liposomal suspension contains approx. 66.6 μmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated $PLP_{139-151}$ peptide is determined by the micro BCA protein assay (Pierce) after dissolving the liposomes in 0.05 M NaOH/1% SDS.

11.5. Preparation of Hydrogel Solutions Containing Calcipotriol and PS-Liposome-Encapsulated $PLP_{139-151}$ Peptide This example describes the synthesis of composites comprising hydrogel-embedded calcipotriol and unilamellar PS-liposomes containing encapsulated $PLP_{139-151}$ peptide.

First, the PLGA-PEG-PLGA triblock copolymer of Example 1.1., dried under vacuum at room temperature until constant weight, is dissolved in 150 μl PBS, pH 7.4, and 50 μl of calcipotriol in a 1:5 solution of ethanol/PBS, pH 7.4

(150 µg/ml corresponding to 7.5 µg/50 µl) to a concentration of 30% w/v polymer. After cooling to 4° C., the hydrogel-calcipotriol composite is mixed with 100 µl PS-liposomes of Example 11.4. (6.7 µmol lipid) containing approx. 220 µg $PLP_{139-151}$ peptide. The final concentration of the hydrogel is 20% w/v polymer containing 3.3%. ethanol.

11.6. Animals

Female SJL/J mice (9-10 weeks of age) are obtained from the Jackson Laboratory. For most uniform EAE development, all mice are the same age. Mice are acclimated for at least 2 weeks before immunization.

11.7. EAE Induction

Mouse stress induced any time after approximately 3 days before immunization (e.g., by excessive handling of mice or excessive noise strongly) reduces both EAE incidence and severity in SJL mice. To reduce stress effects induced by subcutaneous injection of $PLP_{139-151}$ in CFA and by subsequent therapeutic injections, sham dosing is performed 7 and 4 days before immunization of the mice. Unlike other EAE models, the stress of treatment and administration of therapeutics continues to affect the disease in SJL mice even after clinical signs of EAE appear.

In addition, a stress minimizing injection technique is applied including a) gripping the mouse tail with finger and thumb of the right hand, b) restraining the mouse against the cage with three remaining fingers of the right hand, c) restraining the mouse with two fingers of the left hand behind its head, and d) using the right hand for subcutaneous injection at 4 sites on the back of the mouse, with 0.05 mL of emulsion at each site: on the upper back, on the upper back, approximately 1 cm away from the initial injection, on the lower back, and on the lower back, approximately 1 cm away from the previous injection.

Using this technique, EAE is consistently induced in 90-100% of the mice, with onset of paralysis between 11 to 15 days after immunization.

All mice develop obvious bumps of emulsion at the injection sites 2 to 4 days after injection. In most mice, the emulsion remains at the site of injection for the duration of the experiment. Approximately 10% to 40% of the mice clear the emulsion by developing skin ulcers at injection sites. Most of the time, these ulcers do not require treatment. They usually heal in a few days with scar formation. In some mice, alopecia will develop at the site of injection 5 to 7 days after injection.

As soon as the first signs of paralysis occur, mice are provided with food pellets and wet food on the floor of the cage, and easily accessible water. HydroGel (CearH2O, Portland Me.) may be used as a source of water during the most severe paralysis. Even mice which develop very severe first wave EAE (score 4) show almost always some recovery within 2 or 3 days. If mice are unable to reach water due to temporary paralysis, Ringer's solution is administered subcutaneously.

The first wave of paralysis is associated with a loss of body weight which is mostly regained on recovery from the first wave. In each subsequent wave there is body weight loss at onset, but not as dramatic as in the first wave. Most of the body weight is regained again at recovery.

11.8. EAE Scoring

Mice are checked for signs of EAE daily, starting on day 7 after the immunization. Following scoring guidelines are used:

score 0 No obvious changes in motor functions of the mouse in comparison to non-immunized mice. When picked up by the tail, the tail has tension and is erect. Hind legs are usually spread apart. When the mouse is walking, there is no gait or head tilting.

score 1 Limp tail. When the mouse is picked up by the tail, instead of being erect, the whole tail drapes over your finger.

score 2 Limp tail and weakness of hind legs. When mouse is picked up by tail, legs are not spread apart, but held closer together. When the mouse is observed when walking, it has a clearly apparent wobbly walk.

Score 3 Limp tail and complete paralysis of hind legs (most common), or limp tail with paralysis of one front and one hind leg, or all of a) severe head tilting, b) walking only along the edges of the cage, c) pushing against the cage wall, and d) spinning when picked up by the tail.

Score 4 Limp tail, complete hind leg and partial front leg paralysis. Mouse is minimally moving around the cage but appears alert and feeding. Usually, euthanasia is recommended after the mouse scores level 4 for 2 days. When the mouse is euthanized because of severe paralysis, score of 5 is entered for that mouse for the rest of the experiment.

Score 5 Complete hind and complete front leg paralysis, no movement around the cage. Mouse is spontaneously rolling in the cage. Mouse is found dead due to paralysis. If mouse is alive, euthanize the mouse immediately if it scores 5. Once mouse is scored 5, the same score is entered for all the days for the rest of the experiment.

In-between scores (i.e. 0.5, 1.5, 2.5, 3.5) are used when the clinical picture lies between two defined scores.

The mean maximum score (MMS) of the first paralytic episode ranges usually between 2.5 and 3.5, and the MMS of the second paralytic episode between 1.5 and 2.5.

11.9. Immunotherapy

To evaluate the therapeutic efficacy of peptide immunotherapy, treatment is initiated in one set of SJL mice at the onset of clinical signs of EAE and in another set of SJL mice at the start of recovery from the first wave of EAE (late therapeutic approach). The day of EAE induction is designated as day 0.

Each set of mice is subjected to three different modalities of immunotherapy. Treatment of group 1 is based on conventional treatment with of alum-adsorbed $PLP_{139-151}$ peptide. For the treatment of group 2, hydrogel-embedded calcipotriol and hydrogel-embedded PS-liposomes containing encapsulated $PLP_{139-151}$ peptide is employed. For the treatment of group 3, non-loaded hydrogel (control) is used. Each group consists of 15 to 20 mice to ensure that enough mice relapse for a reliable statistical analysis.

Conventional immunotherapeutic treatment: subcutaneous administration of 0.3 ml PBS (150 µl at two different sites) containing 200 µg alum-adsorbed $PLP_{139-151}$ peptide, performed eight times at 5-day intervals.

Immunotherapeutic approach based on PS-liposomes and calcipotriol: subcutaneous administration of 0.3 ml of a 20% w/v hydrogel (150 µl at two different sites) containing 7.5 µg calcipotriol and 220 µg of PS-liposome-encapsulated $PLP_{139-151}$ peptide, performed eight times at 5-day intervals.

Control: subcutaneous administration of 0.3 ml of a 20% w/v non-loaded hydrogel (150 µl at two different sites), performed eight times at 5-day intervals.

11.10. Readouts of Immunotherapy

The most important readouts in this EAE model are a) incidence of relapse and b) MMS of the relapse period, calculated for all mice. The MMS of only those mice which relapse rarely shows significant differences between groups because only a fraction of mice relapse and relapse severity tends to be variable even within a single group. The MMS of the relapse period is more sensitive because it is based on all mice in the group and reflects both relapse severity and residual EAE severity in those mice which do not relapse.

Example 12: Immunotherapy of Adjuvant Arthritis in Lewis Rats with TNFR1-Specific Inhibitors and PS-Liposome-Encapsulated HSP65 Nona-Peptide 180-188

This example investigates the efficacy of peptide immunotherapy of adjuvant arthritis in rats induced by intradermal injection of a mycobacterial 65 kDa heat shock protein (hsp65) emulsified in incomplete Freund's adjuvans, with a) alum-adsorbed MT-Hsp65-derived nonpeptide 180-188 and b) with hydrogel-embedded PS-liposomes containing encapsulated MT-Hsp65-derived nonpeptide 180-188 and a combination of polymer-embedded TNFR1-specific inhibitors including salicylic acid and a TNFR1-specific 22mer pPT antisense ODN.

Adjuvant arthritis is an animal model for rheumatoid arthritis and is induced in Lewis rats by immunization with heat-killed *Mycobacterium tuberculosis* in Freund's incomplete adjuvant (Van Eden et al., 1988). Evidence for a role of Hsp65 in adjuvant arthritis was obtained by characterization of arthritogenic and protective T cell clones generated from arthritic rats (Cohen et al., 1985). The epitope recognized by the clones was first identified as a nine amino acid sequence (180-188) of mycobacterial Hsp65 (Van Eden et al., 1988) and later shortened to amino acid sequence 180-186 (Van der Zee et al., 1989). Vaccination with the nonapeptide 180-188 has been shown to induce protection against adjuvant arthritis (Yang et al., 1990). In separate experiments, 11 out of 16 Lewis rats immunized three times with 100 µg of the nonapeptide emulsified in Freund's incomplete adjuvant (FIA) prior to induction of adjuvant arthritis were completely protected against subsequently induced adjuvant arthritis.

Important for therapeutic purposes is the fact that the nonapeptide is not arthritogenic. As demonstrated in the study of Yang et al. (1990), none of the rats treated 35 days before the induction of adjuvant arthritis by i.p. injection of 100 µg of the nonapeptide emulsified in FIA, showed any clinical symptoms of adjuvant arthritis during the pretreatment period. Due to the non-arthritogenic nature of the nonapeptide, immunotherapy does not require the application of increasing doses of the nonapeptide. Instead, the immunotherapy is performed with repetitive doses of 100 µg alum-absorbed nonapeptide and 120 µg PS-liposome-encapsulated nonapeptide.

12.1. Animals

Inbred male Lewis rats (6-8 weeks of age) are obtained from Charles River Laboratories.

12.2. Materials

Imject Alum is obtained from Pierce/KMF. Salicylic acid (SA; solubility in water: 14 mM, in ethanol/water (10:90 vol) 21 mM, in ethanol/water (20:80 vol) 35 mM, in ethanol/water (30:70 vol) 81 mM, in ethanol/water (40:60 vol) 277 mM, in ethanol/water (50:50 vol) 526 mM) is obtained from Sigma.

12.3. Synthesis of TNFR1-Specific Antisense ODN

TNFR1-specific antisense ODN comprising partial phosphorothioate linkages (pPT) are synthesized and formulated with Cellfectin as described in Example 5.4.

12.4. Synthesis of the Nonapeptide 180-188

The nonapeptide Thr-Phe-Gly-Leu-Gln-Leu-Glu-Leu-Thr representing sequence 180-188 of Hsp65 from *Mycobacterium bovis* BCG (van Eden et al., 1988) is synthesized by solid-phase peptide synthesis according to standard procedures.

12.5. Cloning, Expression and Purification of Mycobacterial Hsp65

The 65 kDa heat shock protein of *Mycobacterium bovis* BCG (MB-hsp65) and control antigen from *E. coli* transfected without the MB-hsp65 gene are prepared as described (Thole et al., 1987; van Eden et al., 1988).

12.6. Preparation of Alum-Adsorbed Nonapeptide 180-188

Ten mg of nonapeptide 180-188 are solved in 3.0 ml of PBS, pH 7.4, and added to 7.0 ml Imject Alum (Pierce/KMF) giving a concentration of 100 µg nonapeptide 180-188 in 0.1 ml PBS/alum suspension. For immunotherapy with alum-adsorbed nonapeptide 180-188, a 3-fold diluted alum suspension in PBS, pH 7.4. is used containing 100 µg alum-adsorbed $PLP_{139-151}$ peptide in 0.3 ml.

12.7. Preparation of PS-Liposomes Containing Encapsulated Nonapeptide 180-188

This example describes the synthesis of unilamellar PS-liposomes containing encapsulated MT-Hsp65-derived nonpeptide 180-188 from a lipid mixture of phosphatidyldserine (PS), either 1-palmitoyl-2-oleoyl-sn-3-glycerophospho-L-serine (POP-L-S) or bovine brain phosphatidyldserin (Avanti Polar Lipids), phosphatidylcholine (PC), either 1-palmitoyl-2-oleoyl-sn-3-glycerophosphocholine (POPC) or egg phosphatidylcholine (Avanti Polar Lipids), and cholesterol (CH; Avanti Polar Lipids) at a ratio of 30:30:40 PS to PC to CH according to Hoffmann et al. (2005).

A chloroform/methanol (2:1, v/v) solution containing 30 µmol PS (approx. 24.4 mg), mol PC (approx. 22.8 mg) and 40 µmol CH (approx. 15.5 mg) is placed in a conical flask and dried by rotary evaporation to prepare a thin lipid film. Thereafter, the flask is placed in a desiccator for at least one hour to completely remove the solvent. Then, 1.5 ml of phosphate-buffered saline (PBS) containing 1.8 mg MT-Hsp65-derived nonpeptide 180-188 is added and multilamellar vesicles are generated by intense vortex dispersion. For the preparation of unilamellar vesicles, the multilamellar preparation is extruded 10 times through a 1 µm pore polycarbonate membrane (Nucleopore, USA). PS-liposomes with a particle size of approx. 1 m are suitable for efficient uptake by macrophages (Harel-Adar et al., 2011). The final liposomal suspension contains approx. 66.6 µmol (39.2 mg) of lipid/1.0 ml. Unilamellar PS-liposomes prepared by this procedure have been shown to disperse uniformly in physiological medium due to repulsion forces (Harel-Adar et al., 2011).

The degree of PS exposure on liposomes is assessed by binding of FITC-annexin V to surface-exposed PS and analysis by FACS. The quantity of liposome-encapsulated MT-Hsp65-derived nonpeptide 180-188 is determined by the micro BCA protein assay (Pierce) after dissolving the liposomes in 0.05 M NaOH/1% SDS.

12.8. Preparation of Hydrogel Solutions Containing Salicylic Acid and a TNFR1-Specific 22Mer pPT Antisense ODN, and PS-Liposome-Encapsulated Peptide 190-188

This example describes the synthesis of composites comprising hydrogel-embedded TNFR1-specific inhibitors including salicylic acid and a TNFR1-specific 22mer pPT antisense ODN, and unilamellar PS-liposomes containing encapsulated MT-Hsp65-derived nonpeptide 180-188.

First, the PLGA-PEG-PLGA triblock copolymer of Example 1.1., dried under vacuum at room temperature until constant weight, is dissolved in 150 µl PBS, pH 7.4, 20 µl of sodium salicylate (SA) in ethanol/water, 50/50 vol (350 mM; final concentration in 300 µl hydrogel composition 23.3 mM SA and 3.3% ethanol), and 30 µl of TNFR1-ODN/ Cellfectin complexes (comprising a mixture of 50 µl of 1.0 µM TNFR1-specific pPT antisense ODN in PBS, 7.4, and 5 µl of 1 mg/ml Cellfectin in PBS, pH 7.4), to a concentration of 30% w/v polymer. After cooling to 4° C., the hydrogel-TNFR1-inhibitor composite is mixed with 100 µl PS-liposomes of Example 12.7. (6.7 µmol lipid) containing approx. 120 µg MT-Hsp65-derived nonpeptide 180-188.

12.9. Arthritis Induction with *Mycobacterium tuberculosis* (MT)

Rats are immunized intradermally at the base of the tail with 100 μl of 10 mg/ml heat-killed MT H37Ra (Difco) in mineral oil (incomplete Freund's adjuvant; IFA) as described (Hogervorst et al., 1992).

Inducing arthritis as described above, clinical symptoms of adjuvant arthritis become evident at day 10, reach a peak at day 20 (highest arthritis score), and decline continuously thereafter until symptoms disappear around day 50 (Hogervorst et al., 1992).

12.10. Immunotherapy

Three sets of male Lewis rats are subjected to immunotherapy, the first 1 week after arthritis induction (approx. 3 days before clinical symptoms of adjuvant arthritis become evident), the second 2 weeks after arthritis induction (approx. 4 days after appearance of clinical symptoms of adjuvant arthritis), and the third 3 weeks after arthritis induction (approx. at the peak of clinical symptoms of adjuvant arthritis). The day of arthritis induction is designated as day 0.

Each set of mice is subjected to three different modalities of immunotherapy. Treatment of group 1 is based on conventional treatment with of alum-adsorbed MT-Hsp65-derived nonpeptide 180-188. For the treatment of group 2, hydrogel-embedded TNFR1-specific inhibitors and hydrogel-embedded PS-liposomes containing encapsulated MT-Hsp65-derived nonpeptide 180-188 is employed. For the treatment of group 3, non-loaded hydrogel (control) is used. Each group consists of 10 mice.

Conventional immunotherapeutic treatment: subcutaneous administration of 0.3 ml PBS (150 μl at two different sites) containing 100 μg alum-adsorbed MT-Hsp65-derived nonpeptide 180-188, performed eight times at 5-day intervals.

Immunotherapeutic approach based on PS-liposomes and TNFR1-specific inhibitors: subcutaneous administration of 0.3 ml of a 20% w/v hydrogel (150 μl at two different sites) containing 23.3 mM SA and 0.09 μM TNFR1-specific pPT antisense ODN (complexed with cellfectin), and approx. 120 μg of PS-liposome-encapsulated MT-Hsp65-derived nonpeptide 180-188, performed eight times at 5-day intervals.

Control: subcutaneous administration of 0.3 ml of a 20% w/v non-loaded hydrogel (150 μl at two different sites), performed eight times at 5-day intervals.

12.11. Evaluation of Clinical Signs of Arthritis

Rats are examined daily for clinical signs of arthritis (erythema, swelling and deformity) and an arthritis index is assigned as described (Taurog et al., 1988): 0, no evidence of disease; 1, inflammation of small digital joints; 2, inflammation of ankle and joints; 3 inflammation of foot-pad; and 4, inflammation of entire foot. Each paw is given a score between 0 and 4, the highest score being 16 per rat.

Arthritis can also be confirmed and evaluated by examination of radiographs (Taurog et al., 1988). Rats are anaesthetized with Evipan-sodium (100 mg/kg, Bayer) and radiographs are taken for fore and hind limbs of rats. Scores of 1-4 are assigned to each joint for peri-osteal reaction, bony erosions, joint space narrowing and joint space destruction.

12.12 Challenge with *Mycobacterium tuberculosis* (MT) after Immunotherapy 10 weeks after induction of adjuvant arthritis, rats are challenged intradermally at the base of the tail with 100 μl of 10 mg/ml heat-killed MT H37Ra (Difco) in incomplete Freund's adjuvant. The potential relapse of adjuvant arthritis is observed for another 5 weeks.

LITERATURE

Abbott, D. J., et al., BMC Immunol. 12: 72; 2011.

Abramson, M. J., et al. Cochrane Database Syst. Rev. CD001186; 2003.

Alexopoulou, L., et al., Eur. J. Immunol. 36: 2768-2780; 2006.

Alhalaweh, A., et al., Eur. J. Pharm. Sci. 38: 206-214; 2009.

Ames, R. S., et al., J. Immunol. 166: 6341-6348; 2001.

Andjelkovic, Z., et al., Clin. Exp. Rheumatol. 17: 453-456; 1999.

Amon, R., Immunol. Lett. 50: 1-125; 1996.

Amon, R., Aharoni R., Proc. Natl. Acad. Sci. USA 101, suppl. 2: 14593-14598; 2004.

Arntz, O. J., et al., Arthritis Res. Therapy 12: R61; 2010.

Arumugam, T. V., et al., Kidney Int. 63:134-142; 2003.

Arumugam, T. V., et al., J. Hepatol. 40: 934-941; 2004.

Arur, S., et al., Develop. Cell 4: 587-598; 2003.

Badawi, A. H., Siahaan T. J., Clin. Immunol. 144: 127-138; 2012.

Baelder, R., et al., J. Immunol. 174: 783-789; 2005.

Balasubramanian, K., Schroit, A. J., J. Biol. Chem. 273: 29272-29277; 1998.

Bao, L., et al., J. Immunol. 175: 1947-1955; 2005a.

Bao, L., et al., Eur. J. Immunol. 35: 2496-2506; 2005b.

Basomba, A., et al., J. Allergy Clin. Immunol. 109: 943-948; 2002.

Belogurov, Jr., A. A., et al., FASEB J. 27: 222-231; 2013.

Bluestone, J. A., et al., Nature 464: 1293-1300; 2010.

Branisteanu, D. D., et al., J. Neuroimmunol. 61: 151-160; 1995.

Brunner, R., et al., Immunol. Lett. 128: 29-35; 2010.

Cailleret, M., et al., Circulation 109: 406-411; 2004.

Cantorna, M. T., et al., J. Nutr. 128: 68-72; 1998.

Chaurio, R. A., et al., Molecules 14: 4892-4914; 2009.

Chemnitz, J. M., et al. J. Immunol. 173: 945-954; 2004.

Chen, X., Oppenheim J. J. In: TNF pathophysiology. Molecular and cellular mechanisms.

Curr. Dir. Autoimmun., pp. 119-134, Karger, Basel; 2010.

Choi, S., et al., Pharmaceut. Res. 20: 2008-2010; 2003.

Cianferoni, A., et al., Blood 97: 1742-1749; 2001.

Cohen, I. R., et al., Arthritis Rheum. 8: 841-845; 1985.

Cohen, S., et al., Biochim. Biophys. Acta 1063: 95-102; 1991.

Das, A., et al., J. Immunol. 192: 1120-1129; 2014.

Demedts, M., et al., N. Engl. J. Med. 353: 2229-2242; 2005.

Diamyd (2011)

a) Diamyd US phase III trial: http://clinicaltrials.gov/ct2/show/NCT00751842 b) Diamyd European phase III trial: http://clinicaltrials.gov/ct2/show/NCT00723411 c) Diabetes prevention—immune tolerance (DIAPREV-IT) http://clinicaltrials.gov/ct2/show/NCT01122446?term=daimyd&rank=6

Eagar, T. N., et al., Eur. J. Immunol. 32: 972-981; 2002.

Elias, D., et al., Proc. Natl. Acad. Sci. USA 87: 1576-1580; 1990.

Elias, D., et al., Proc. Natl. Acad. Sci. USA 88: 3088-3091; 1991.

Elliott, M. R., et al., Nature 461: 282-286; 2009.
Engel, A., et al., Pharmaceutical Res. 20: 51-57; 2003.
Eylar, E., et al., Int. Immunol. 1: 97-101; 1993.
Fadok, V. A., et al., J. Immunol. 148:2207-2216; 1992.
Fadok, V. A., et al., J. Biol. Chem. 276: 1071-1077; 2001.
Faria, A. M., Weiner, H. L., Immunol. Rev. 206: 232-259; 2005.
Fife, B. T., et al., J. Exp. Med. 203: 2737-2747; 2006.
Fletcher, J. M., et al., Recent Pat. Inflamm. Allergy Drug Discov. 6: 22-34; 2012.
Francois, C., et al., Patent WO2009046198.
Fukasawa, M., et al., FEBS Letters 441:353-366; 1998.
Furst, D. E., et al., J. Rheumatol. 14: 342-347; 1987.
Galvain, S., et al., Current Therap. Res. 60: 278-294; 1999.
Gao, X., et al., Clin. Immunol. 140: 236-243; 2011.
Gardai, S. J., et al., Cell 123: 321-334; 2005.
Garren, H., et al., Ann. Neurol. 63: 611-620; 2008.
Gaskins, H. M., et al., J. Clin. Invest. 90: 2220-2227; 1992.
Geelen, T., et al., J. Nanobiotechnology 10: 37-48; 2012.
Getts, D. R., et al., J. Immunol. 187: 2405-2417; 2011.
Ghoreishi, M., et al., J. Immunol. 182: 6071-6078; 2009.
Gilbert, J. C., et al., J. Control. Release 5: 113-118; 1987.
Gilbreath, M. J., et al., J. Immunol. 134: 3420-3425; 1985.
Giulietti, A., et al., Diabetologica 47: 451-462; 2004.
Gogishvili, T., et al., Int. Arch. Allergy Immunol. 142: 165-174; 2006.
Gong, C. Y., et al., Int. J. Pharm. 365: 89-99; 2009a.
Gong, C. Y., et al., BMC Biotechnol. 9: 8; 2009b.
Goulding, N. J., et al., Inflamm. Res. 3: S158-S165; 1998.
Grassetti, D. R., Murray, J. F., Arch. Biochem. Biophys. 119: 41-49; 1967.
Grunewald, S. M., et al., J. Immunl. 160: 404-4009; 1998.
Hagenaars, N., et al., J. Control. Release 144: 17-24; 2010.
Hanayama, R., et al., Nature 417: 182-187; 2002.
Harel-Adar, T., et al., Proc. Natl. Acad. Sci. USA 108: 1827-1832; 2011.
Harkin, D. W., et al., J. Vasc. Surg. 39: 196-205; 2004.
Harris, S. S., J. Nutr. 135: 323-325; 2005.
Hashimoto, M., et al., J. Exp. Med. 207: 1135-1143; 2010.
Higuchi, K., et al., J. Rheumatol. 27: 1038-1044; 2000.
Hochreiter-Hufford, A., Ravichandran, K. S., Cold Spring Harb. Perspect. Biol. 5: a008748; 2013.
Hoffmann, P. R., et al., J. Immunol. 174: 1393-1404; 2005.
Hogervorst, E. J. M., et al., Internatl. Immunol 4: 719-727; 1992.
Holgate, S T., Polosa, R., Nature Rev. Immunol 8: 218-230; 2008.
Huang, X. W., et al., Clin. Cancer Res. 12: 2849-2855; 2006.
Huber-Lang, M., et al., Am. J. Pathol. 161: 1849-1859; 2002.
Hyppönen, E., et al., Lancet 358: 1500-1503; 2001.
Hyun, H., et al., Biomacromolecules 8: 1093-1100; 2007.
Ichim, T. E., et al., Expert Opin. Biol. Ther. 8: 191-199; 2008.
Igarashi, M., et al., Clin. Exper. Immunol. 93: 19-25; 1993.
Ikehara, Y., et al., Cancer Res. 66: 8740-8748; 2006.
Ishii, M., et al., Intern. Immunopharmacol. 10: 1041-1046; 2010.
Iyer, R. P., et al., J. Org. Chem. 55: 4693-4699; 1990.
Jacobsen, L., et al., Allergy 62: 943-948; 2007.
Jeannin, P., et al., J. Exp. Med. 182: 1785-1792; 1995.
Jenkins, M. K., Schwartz, R. H., J. Exp. Med. 165: 202-319; 1987.
Jeong, B., et al., Nature 388: 860-862, 1997.
Jurynczyk, M., et al., Ann. Neurol. 68: 593-601; 2010.
Kamphuis, S., et al., Lancet 366: 50-56; 2005.
Kang, Y. M., et al., Biomaterials 31: 2453-2460; 2010.
Kassiotis, G., Kollias, G., J. Exp. Med. 1993: 427-434; 2001.
Kawakami, S., et al., Biochim. Biophys. Acta 1524: 258-265; 2000.
Kawakita, A., et al., Allergy 67: 371-379; 2012.
Kelly, G. S., Alt. Med. Rev. 3: 114-127; 1998.
Kim, A., et al., Biomaterials 25: 305-313; 2004.
Kim, S T., et al., J. Gene Med. 11: 26-37; 2009.
Kimball, S. M., et al., Am. J. Clin. Nutr. 86: 645-651; 2007.
Kissmeyer, A.-M., Binderup, L., Biochem. Pharmacol. 41: 1601-1606; 1991.
Kohl, J., Curr. Opin. Mol. Ther. 8: 529-538; 2006.
Kono, H., Rock, K. L., Nature Rev. Immunol. 8: 279-289; 2008.
Kornbluth, R. S., Immunol. Lett. 43: 125-132; 1994.
Kragballe K., Pharmacol. Toxicol. 77: 241-246; 1995.
Kukoc-Modun, L., Radic, N., Internatl. J. Analyt. Chem. 2011: article ID 140756; 2011.
Landewe, R. B. M., et al., Ann. Rheum. Dis. 69: 1655-1659; 2010.
Leadbetter, E. A., et al., J. Immunol. 161: 504-512; 1998.
Lee, Y. C., et al., Biochemistry 15:3956-3963; 1976.
Leroux-Roels, G., Vaccine 285: C25-C36; 2010.
Lin, M., et al., Diabetes 59: 2247-2252; 2010.
Liu, J., et al., J. Immunol. 180: 5882-5889; 2008.
Ludvigsson, J., et al., N. Engl. J. Med. 359: 676-781; 2008.
Lutterotti, A., et al., Sci. Translat. Med. 5: 1-19; 2013.
Macauley, M. S., et al., J. Clin. Invest. 123: 3074-3083; 2013.
Majak P., et al., J. Allergy Clin. Immunol. 127: 1294-1296; 2011.
Markiewski, M. M., et al., Nat. Immunol. 9: 1225-1235; 2008.
Mathieu, C., et al., Diabetologica 37: 552-558; 1994.
Meechan, P., et al., Int. Arch. Allergy Immunol. 61: 351-362; 2013.
Mizuochi, T., et al., J. Biol Chem. 264: 13834-13939; 1989.
Moller, C., et al., J. Allergy Clin. Immunol. 109: 251-256; 2002.
Monastra, G., Bruni, A., Lymphokine Cytokine Res. 11:39-43; 1992.
Monastra, G., et al., Neurology 43: 153-163; 1993.
Monk, P. N., et al., Brit. J. Pharmacol. 152: 429-448; 2007.
Nicholls, E. F., et al., Ann. N. Y. Acad. Sci. 1213: 46-61; 2010.
Nie, S., et al., Internatl. J. Nanomed. 6: 151-166; 2011.
Nomura, T., et al., J. Control. Release 149: 8-14; 2011.
Ojwang, J. O., Rando R. F. METHODS: A Companion to Methods in Enzymology 18: 244-251; 1999.
Østergaard, J. A., et al., Diabetes 60: e7-e8; 2011.
Pai, S. S., et al., Am. Assoc. Pharmac. Sci. J. 11: 88-98; 2009.
Peng, K.-T., et al., Biomaterials 31: 5227-5236; 2010.
Pfrengle, F., et al., J. Immunol. 191: 1724-1731; 2013.
Plum, L. A., DeLuca, H. F., Nat. Rev. Drug Discov. 9: 941-955; 2010.
Ponzin, D., et al., Immunopharmacol. 18: 167-176; 1989.
Proctor, L. M., et al., Brit. J. Pharmacol. 142: 756-764; 2004.
Qiao, M. et al., Int. J. Pharm. 294: 103-112; 2005.
Qu, H., et al., Mol. Immunol. 47: 185-195; 2009.
Ravichandran, K. S., J. Exp. Med. 207: 1807-1817; 2010.
Ravichandran, K. S., Immunity 35: 445-455; 2011.
Ricklin, D., Lambris, J. D., Adv. Exp. Med. Biol. 632: 273-292; 2008.
Rolland, J. M., et al., Pharmacol. Ther. 121: 273-284; 2009.
Ross, P. C., et al., J. Liposome Res. 8: 499-520; 1998.

Ruel-Gariepy, E., Leroux, J-C., Eur. J. Pharmaceutics Biopharmaceutics 58: 409-426; 2004.
Sahu, A., et al., J. Immunol. 157: 884-891; 1996.
Sahu, A., et al., Mol. Immunol. 39: 557-566; 2003.
Schmidt-Weber, C., Blaser, K. Inflamm. Allergy Drug Targets 5: 15-21; 2006.
Shephard, R. M., DeLuca, H. F., Arch. Biochem. Biophys. 202: 43-53; 1980.
Shibata, H., et al., J. Biol. Chem. 283: 998-1007; 2008.
Shibata, H., et al., Biomaterials 30: 6638-6647; 2009.
Silasi-Mansat, R., et al., Blood 116: 1002-1010; 2010.
Singh, S., et al., Int. J. Pharmaceutics 341: 68-77; 2007.
Sinha, V. R., et al., Int. J. Pharm. 278: 1-23; 2004.
Skyler, J. S., et al., Diabetes Care 28: 1068-1076; 2005.
Steed, P. M., et al., Science 301: 1895-1898; 2003.
Steinman, L., Zamvil, S. S., Ann. Neurol. 68: 567-569; 2010.
Strainic, M. G., et al., Immunity 28: 425-435; 2008.
Sun, Y. P., et al., J. Biol. Chem. 282: 9323-9334; 2007.
Suvannavejh, G. C., et al., Cell. Immunol. 205: 24-33; 2000.
Taher, Y. A., et al., J. Immunol. 180: 5211-5221; 2008.
Tan, L. J., et al., J. Immunol. 147: 1797-1802; 1991.
Taurog, J. D., et al., Methods Enzymol. 162: 339-355; 1988.
Thole, J. E. R., et al., Infect. Immun. 55:1466-1475; 1987.
Thommesen, L., Laegreid, A., J. Biochem. Mol. Biol. 38: 281-289; 2005.
Ting, E., et al., Br. J. Pharmacol. 153: 1043-1053; 2008.
Tirouvanziam R., et al., Proc. Natl. Acad. Sci. USA 103: 4628-4633; 2006.
Tony, H. P., et al., Eur. J. Biochem. 225: 659-665; 1994.
Torchilin, V. P., Nature Rev. 4: 145-160; 2005.
van der Aar, A. M. G., et al., J. Allergy Clin. Immunol. 127: 1532-1540; 2011.
van der Zee, R., et al., Eur. J. Immunol. 19: 43-47; 1989.
van Eden, W., et al., Nature 331: 171-173; 1988.
Van Hauwermeiren, F., et al., Cytokine Growth Factors Rev. 22: 311-319; 2011.
Voll, R. E., et al., Nature 390:350-351; 1997.
Wagner, E., Frank M. M., Nature Rev. 9:43-56; 2010.
Warren, K. G., et al., Eur. J. Neurol. 13: 887-895; 2006.
Wei, X, et al., Pharm Res. 23: 1251-1264. doi: 10.1007/s11095-006-0082-3; 2006.
Wenzel, S., et al., Lancet 370: 1422-1431; 2007.
Wingerchuk D. M., et al., J. Neurol. Neurosurg. Psychiatry 76: 1294-1296; 2005.
Wittke, A., et al., J. Immunol. 173: 3432-3436; 2004.
Woodruff, T. M., et al., Arthritis Rheum. 46: 2476-2485; 2002.
Woodruff, T. M., et al., J. Pharmacol. Exp. Ther. 314: 811-817; 2005.
Woodruff, T. M., et al., FASEB J. 20: 1407-1417; 2006.
Wu, Y., et al., Biomaterials 33: 2351-3260; 2012.
Xing, Y., et al., J. Liposome Res., early online 1-7; 2013.
Yalcindag, A., et al., J. Allergy Clin. Immunol. 117: 1455-1461; 2006.
Yang, X., et al., Clin. Exp. Immunol. 81: 189-194; 1990.
Zaharoff, D. A., et al., Vaccine 25: 2085-2094; 2007.
Zella, J. B., et al., Arch. Biochem. Biophys. 417: 77-80; 2003.
Zhang, J., et al., Biomacromolecules 7: 2492-2500; 2006.
Zhang, X, Kohl, J., Expert Rev. Clin. Immunol. 6: 269-277; 2010.

The invention claimed is:

1. A pharmaceutical composition for modulation of T cell and B cell responses by allergen-specific immunotherapy in combination with peripheral tolerance-inducing phagocytosis, wherein the pharmaceutical composition consists of one or more preparations, wherein the pharmaceutical composition comprises:
   a) at least one antigen or allergen,
   b) a matrix suitable for locally restricted sustained release of therapeutically effective doses of the at least one antigen or allergen consisting of a PLGA-PEG-PLGA, which is thermogelling, wherein the gelling temperature is between 20° C. and 40° C.,
   c) liposomes tailored for effective phagocytosis exposing on their surface phosphatidylserine, optionally containing OVA, said liposomes further containing said at least one antigen or allergen,
   d) one or more immune modulators of phagocytosis selected from 'find me' signals the selected from nucleotides ATP and UTP, the one or more immune modulators of phagocytosis being released at a rate of more than 50% in 24 hours and more than 70% in 48 hours, and
   e) one or more immune modulators suitable for enhancing the suppressive function of regulatory T cells at the site of antigen or allergen presentation, selected from vitamin D3 analogue Calcipotriol and IL-4/IL-13 antagonist Q, the one or more immune modulators suitable for enhancing the suppressive function of regulatory T cells being released at a rate of more than 80% in 48 hours.

2. The composition according to claim 1, wherein all components of the pharmaceutical composition are mixed as a single preparation, comprising (i) the matrix, (ii) at least one non-encapsulated or liposome-encapsulated allergen, and (iii) at least one immune modulator of phagocytosis.

3. The composition according to claim 1, wherein a first preparation comprises the matrix, the liposomes tailored for effective phagocytosis, at least one immune modulator of phagocytosis, and at least one immune modulator suitable for enhancing the suppressive function of regulatory T cells, wherein a second preparation comprises at least one antigen or allergen coated or adsorbed on or embedded in a second matrix, wherein the second matrix is an adjuvant providing a depot effect for antigen presentation, being selected from aluminum salts or CpG oligonucleotides, and wherein the first and the second matrices are provided in separate preparations.

4. The composition according to claim 1, wherein the composition is galenically prepared for administration by injection or by implantation, intradermally, subcutaneously, nasally, transbucally, transmucosally, sublingually, intraocularly, intramuscularly, or topically.

5. The composition according to claim 1 wherein the pharmaceutical composition comprises:
   a) at least one allergen,
   b) a matrix suitable for locally restricted sustained release of therapeutically effective doses of the at least one allergen comprising triblock copolymers consisting of PLGA-PEG-PLGA, which is reverse thermogelling, wherein the gelling temperature is between 20° C. and 40° C.,
   c) liposomes tailored for effective phagocytosis exposing on their surface phosphatidylserine, said liposomes further containing said at least one antigen or allergen,
   d) one immune modulators of phagocytosis, selected from ATP and UTP,
   e) calcipotriol.

6. A pharmaceutical composition for modulation of T cell and B cell responses by allergen-specific immunotherapy in combination with peripheral tolerance-inducing phagocytosis, wherein the pharmaceutical composition consists of two preparations, wherein the first preparation comprises:
   a) a first matrix suitable for locally restricted sustained release of therapeutically effective doses of at least one antigen or allergen consisting of a PLGA-PEG-PLGA, which thermogelling, wherein the gelling temperature is between 20° C. and 40° C., b) liposomes tailored for effective phagocytosis exposing on their surface phosphatidylserine, optionally containing OVA, said liposomes further containing said at least one antigen or allergen, c) one or more immune modulator of phagocytosis selected from 'find me' signals selected from the nucleotides ATP and UTP, the one or more immune modulators of phagocytosis being released at a rate of more than 50% in 24 hours and more than 70% in 48 hours, d) one or more immune modulator suitable for enhancing the suppressive function of regulatory T cells at the site of antigen or allergen presentation selected from vitamin D3 analogue Calcipotriol- and IL-4/IL-13 antagonist QY, the one or more immune modulators suitable for enhancing the suppressive function of regulatory T cells being released at a rate of more than 80% in 48 hours, and wherein the second preparation comprises e) at least one antigen or allergen wherein the at least one antigen or allergen is coated or adsorbed on or embedded in a second matrix, wherein the second matrix is an adjuvant providing a depot effect for antigen or allergen presentation, being selected from aluminum salts or CpG oligonucleotides, and wherein the first and the second matrices are provided in separate preparations.

* * * * *

SEQUENCE LISTING

```
<160> NUMBER OF SEQ ID NOS: 7

<210> SEQ ID NO 1
<211> LENGTH: 2258
<212> TYPE: DNA
<213> ORGANISM: Homo sapiens

<400> SEQUENCE: 1
ctcctccagc tcttcctgtc ccgctgttgc aacactgcct cactcttccc ctcccacctt      60
ctctcccctc ctctctgctt taattttctc agaattctct ggactgaggc tccagttctg     120
gcctttgggg ttcaagatca ctgggaccag gccgtgatct ctatgcccga gtctcaaccc     180
tcaactgtca ccccaaggca cttgggacgt cctggacaga ccgagtcccg ggaagcccca     240
gcactgccgc tgccacactg ccctgagccc aaatggggga gtgagaggcc atagctgtct     300
ggcatgggcc tctccaccgt gcctgacctg ctgctgccac tggtgctcct ggagctgttg     360
gtgggaatat acccctcagg ggttattgga ctggtccctc acctagggga cagggagaag     420
agagatagtg tgtgtcccca aggaaaatat atccaccctc aaaataattc gatttgctgt     480
accaagtgcc acaaaggaac ctacttgtac aatgactgtc caggcccggg caggatacg      540 gactgcaggg agtgtgagag cggctccttc accgcttcag aaaaccacct cagacactgc     600
ctcagctgct ccaaatgccg aaaggaaatg ggtcaggtgg agatctcttc ttgcacagtg     660
gaccgggaca ccgtgtgtgg ctgcaggaag aaccagtacc ggcattattg gagtgaaaac     720
cttttccagt gcttcaattg cagcctctgc ctcaatggga ccgtgcacct ctcctgccag     780
gagaaacaga acaccgtgtg cacctgccat gcaggttttc ttctaagaga aaacgagtgt     840
gtctcctgta gtaactgtaa gaaaagcctg gagtgcacga agttgtgcct accccagatt     900
```

```
gagaatgtta agggcactga ggactcaggc accacagtgc tgttgcccct ggtcattttc    960
tttggtcttt gccttttatc cctcctcttc attggtttaa tgtatcgcta ccaacggtgg   1020
aagtccaagc tctactccat tgtttgtggg aaatcgacac ctgaaaaaga gggggagctt   1080
gaaggaacta ctactaagcc cctggcccca aacccaagct tcagtcccac tccaggcttc   1140 accccaccc  tgggcttcag tcccgtgccc agttccacct tcacctccag ctccacctat   1200 accccggtg  actgtcccaa ctttgcggct cccgcagag  aggtggcacc acctatcag    1260 ggggctgacc ccatccttgc gacagccctc gcctccgacc ccatcccaa  ccccttcag    1320 aagtgggagg acagcgccca caagccacag agcctagaca ctgatgaccc cgcgacgctg   1380
tacgccgtgg tggagaacgt gccccgttg  cgctggaagg aattcgtgcg gcgcctaggg   1440
ctgagcgacc acgagatcga tcggctggag ctgcagaacg gcgctgcct  gcgcgaggcg   1500 caatacagca tgctggcgac ctggaggcgg cgcacgccgc ggcgcgaggc cacgctggag   1560
ctgctgggac gcgtgctccg cgacatggac ctgctgggct gcctggagga catcgaggag   1620
gcgctttgcg gccccgccgc cctcccgccc gcgcccagtc ttctcagatg aggctgcgcc   1680
cctgcgggca gctctaagga ccgtcctgcg agatcgcctt ccaaccccac ttttttctgg   1740
aaaggagggg tcctgcaggg gcaagcagga gctagcagcc gcctacttgg tgctaacccc   1800
tcgatgtaca tagcttttct cagctgcctg cgcgccgccg acagtcagcg ctgtgcgcgc   1860
ggagagaggt gcgccgtggg ctcaagagcc tgagtgggtg gtttgcgagg atgagggacg   1920
ctatgcctca tgcccgtttt gggtgtcctc accagcaagg ctgctcgggg gccctggtt   1980 cgtccctgag cctttttcac agtgcataag cagtttttt  tgtttttgtt ttgttttgtt   2040 ttgttttttaa atcaatcatg ttacactaat agaaacttgg cactcctgtg ccctctgcct   2100
ggacaagcac atagcaagct gaactgtcct aaggcagggg cgagcacgga acaatggggc   2160
cttcagctgg agctgtggac ttttgtacat acactaaaat tctgaagtta aagctctgct   2220
cttggaaaaa aaaaaaaaaa aaaaaaaaaa aaaaaaaa                           2258

<210> SEQ ID NO 2
<211> LENGTH: 363
<212> TYPE: DNA
<213> ORGANISM: Mus musculus

<400> SEQUENCE: 2
catatccacg gatgcgacaa aaatcacttg agagagatca tcggcatttt gaacgaggtc     60
acaggagaag ggacgccatg cacggagatg gatgtgccaa cgtcctcac  agcaacgaag    120 aacaccacag agagtgagct cgtctgtagg gcttccaagg tgcttcgcat attttattta    180
aaacatggga aaactccatg cttgaagaag aactctagtg ttctcatgga gctgcagaga    240
ctctttcggg cttttcgatg cctggattca tcgataagct gcaccatgaa tgagtccaag    300
tccacatcac tgaaagactt cctggaaagc ctaaagagca tcatgcaaat ggattactcg    360
tag                                                                  363

<210> SEQ ID NO 3
<211> LENGTH: 120
<212> TYPE: PRT
<213> ORGANISM: Mus musculus

<400> SEQUENCE: 3

His Ile His Gly Cys Asp Lys Asn His Leu Arg Glu Ile Ile Gly Ile
1               5                   10                  15
```

```
Leu Asn Glu Val Thr Gly Glu Gly Thr Pro Cys Thr Glu Met Asp Val
            20                  25                  30

Pro Asn Val Leu Thr Ala Thr Lys Asn Thr Thr Glu Ser Glu Leu Val
        35                  40                  45

Cys Arg Ala Ser Lys Val Leu Arg Ile Phe Tyr Leu Lys His Gly Lys
50                  55                  60

Thr Pro Cys Leu Lys Lys Asn Ser Ser Val Leu Met Glu Leu Gln Arg
65                  70                  75                  80

Leu Phe Arg Ala Phe Arg Cys Leu Asp Ser Ser Ile Ser Cys Thr Met
                85                  90                  95

Asn Glu Ser Lys Ser Thr Ser Leu Lys Asp Phe Leu Glu Ser Leu Lys
            100                 105                 110

Ser Ile Met Gln Met Asp Tyr Ser
            115                 120
```

```
<210> SEQ ID NO 4
<211> LENGTH: 429
<212> TYPE: DNA
<213> ORGANISM: Artificial
<220> FEATURE:
<223> OTHER INFORMATION: Murine IL4 mutant

<400> SEQUENCE: 4
```

```
atgggtagca gccatcatca tcatcatcac tccagcggtc tggttcctcg tggtagtcat      60
atgcacattc acgggtgtga caaaaatcat ctgcgcgaga ttatcggtat tctgaacgaa     120
gtgaccggag aaggcactcc ttgtacggaa atggatgtcc cgaacgtcct gacagcgacg     180
aaaaacacaa cggaatcgga actggttttgc cgtgccagca agtcctgcg catcttctat     240
ctgaaacatg gtaaaacgcc gtgtctgaaa aaaaacagca gcgttctgat ggaactgcaa     300
cgcctgtttc gtgctttccg ctgcctggat agcagtatca gctgtacgat gaacgagtcc     360
aaatcaaccct ccctgaaaga cttcctggaa tcactgaaat cgatcatgga tatggatgac    420
agctgataa                                                            429
```

```
<210> SEQ ID NO 5
<211> LENGTH: 141
<212> TYPE: PRT
<213> ORGANISM: Artificial
<220> FEATURE:
<223> OTHER INFORMATION: Murine IL4 mutant

<400> SEQUENCE: 5
```

```
Met Gly Ser Ser His His His His Ser Ser Gly Leu Val Pro
1               5                   10                  15

Arg Gly Ser His Met His Ile His Gly Cys Asp Lys Asn His Leu Arg
                20                  25                  30

Glu Ile Ile Gly Ile Leu Asn Glu Val Thr Gly Glu Gly Thr Pro Cys
            35                  40                  45

Thr Glu Met Asp Val Pro Asn Val Leu Thr Ala Thr Lys Asn Thr Thr
50                  55                  60

Glu Ser Glu Leu Val Cys Arg Ala Ser Lys Val Leu Arg Ile Phe Tyr
65                  70                  75                  80

Leu Lys His Gly Lys Thr Pro Cys Leu Lys Lys Asn Ser Ser Val Leu
                85                  90                  95

Met Glu Leu Gln Arg Leu Phe Arg Ala Phe Arg Cys Leu Asp Ser Ser
            100                 105                 110
```

-continued

```
Ile Ser Cys Thr Met Asn Glu Ser Lys Ser Thr Ser Leu Lys Asp Phe
        115                 120                 125

Leu Glu Ser Leu Lys Ser Ile Met Asp Met Asp Ser
        130                 135             140

<210> SEQ ID NO 6
<211> LENGTH: 24
<212> TYPE: PRT
<213> ORGANISM: Homo sapiens

<400> SEQUENCE: 6

Val Leu Gly Gly Gly Cys Ala Leu Leu Arg Cys Ile Pro Ala Leu Asp
1               5                   10                  15

Ser Leu Thr Pro Ala Asn Glu Asp
            20

<210> SEQ ID NO 7
<211> LENGTH: 13
<212> TYPE: PRT
<213> ORGANISM: Homo sapiens

<400> SEQUENCE: 7

His Ser Leu Gly Lys Trp Leu Gly His Pro Asp Lys Phe
1               5                   10
```